US011718879B2

(12) United States Patent
Firat et al.

(10) Patent No.: US 11,718,879 B2
(45) Date of Patent: Aug. 8, 2023

(54) NON-CODING RNAS (NCRNA) FOR THE DIAGNOSIS OF COGNITIVE DISORDERS

(71) Applicants: AMONETA DIAGNOSTICS, Huningue (FR); Hueseyin Firat, Huningue (FR); Saliha Moussaoui, Bartenheim (FR); Eric Schordan, Wentzwiller (FR)

(72) Inventors: Hueseyin Firat, Huningue (FR); Saliha Moussaoui, Bartenheim (FR); Eric Schordan, Wentzwiller (FR)

(73) Assignee: AMONETA DIAGNOSTICS, Huningue (FR)

( * ) Notice: Subject to any disclaimer, the term of this patent is extended or adjusted under 35 U.S.C. 154(b) by 42 days.

(21) Appl. No.: 16/644,812

(22) PCT Filed: Sep. 5, 2018

(86) PCT No.: PCT/EP2018/073905
§ 371 (c)(1),
(2) Date: Mar. 5, 2020

(87) PCT Pub. No.: WO2019/048500
PCT Pub. Date: Mar. 14, 2019

(65) Prior Publication Data
US 2021/0071252 A1 Mar. 11, 2021

Related U.S. Application Data

(60) Provisional application No. 62/554,427, filed on Sep. 5, 2017.

(51) Int. Cl.
*C12Q 1/6883* (2018.01)
(52) U.S. Cl.
CPC ..... *C12Q 1/6883* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

2018/0371548 A1   12/2018   Backes et al.

FOREIGN PATENT DOCUMENTS

| EP | 1 716 227 A2 | 11/2006 |
| EP | 3184646 A1 | 6/2017 |
| WO | WO 2013/024469 A1 | 2/2013 |
| WO | WO 2014/075911 A1 | 5/2014 |
| WO | WO 2015/031958 A1 | 3/2015 |
| WO | WO2015/179909 | 12/2015 |
| WO | WO 2020/049135 A1 | 12/2020 |

OTHER PUBLICATIONS

Tan (Mol Neurobiol 2013 47:382-393).*
Sarropoulos (Nature vol. 571 Jul. 25, 2019).*
Bolha (Disease Markers vol. 2017 Article ID 7243968, 14 pages pub May 29, 2017).*
Zhou (Briefings in Bioinformatics 20(2) 2019 598-608).*
Deng (Int J Clin Exp Pathol 2017;10(4) pp. 4694-4699).*
Hu et al., "Diagnostic Value of microRNA for Alzheimer's Disease: A Systematic Review and Meta-Analysis", Front Aging Neurosci., 8:1-9, (2016).
Luo et al., "Long noncoding RNAs and Alzheimer's disease", Clin. Interv. Aging, 11: 867-872, (2016).
Carlson et al., "Amyloid-related imaging abnormalities from trials of solanezumab for Alzheimer's disease," Alzheimer's Dement (Amst), vol. 2, pp. 75-85, (2016). DOI: http://dx.doi.org/10.1016/j.dadm.2016.02.004.
Chetelat et al., "Amyloid imaging in cognitively normal individuals, at-risk populations and preclinical Alzheimer's disease," NeuroImage: Clinical, vol. 2, pp. 356-365, (2013), DOE http://dx.doi.org/10.1016/j.nicl.2013.02.006.
Choi et al., "Preclinical Properties of 18F-AV-45: A PET Agent for Aβ Plagues in the Brain," Journal of Nuclear Medicine, vol. 50, No. 11, pp. 1887-1894, (2009). DOI: 10.2967/jnumed.109.065284.
Cummings et al., "Repackaging FDA-approved drugs for degenerative diseases: promises and challenges," Expert Review of Clinical Pharmacology, vol. 7, No. 2, pp. 161-165, (2014), DOI: 10.1186/s13195-016-0207-9.
Deng et al., "Plasma long noncoding RNA 51A as a stable biomarker of Alzheimer's disease," International Journal of Clinical and Experimental Pathology, vol. 10, No. 4, pp. 4694-4699, (2017).
Dubois et al., "Advancing research diagnostic criteria for Alzheimer's disease: the IWF-2 criteria," Lancet Neurology, vol. 13, No. 6, pp. 614-629, (2014).
Feng et al., "Plasma long non-coding RNA BACE1 as a novel biomarker for diagnosis of Alzheimer disease," BMC Neurology, vol. 18, No. 1, (2018). DOI: 10.1186/s12883-017-1008-x.
Frisoni et al., "The clinical use of structural MRI in Alzheimer disease," National Reviews Neuroscience, vol. 6, No. 2, pp. 67-77, (2010). DOI: 10.103 8/nfneurol.2009.215.
Geekiyanage et al., "Blood serum miRNA: Non-invasive biomarkers for Alzheimer's disease," Experimental Neurology, vol. 235, No. 2, pp. 491-496, (2012). DOI: 10.1016/j.expneurol.2011.11.026.
Gotz et al., "Tau-targeted treatment strategies in Alzheimer's disease," British Journal of Pharmacology and Chemotherapy, vol. 165, No. 5, pp. 1246-1259, (2012). DOI: 10.1111/j.1476-5381.2011.01713.x.
Gui et al., "Altered microRNA profiles in cerebrospinal fluid exosome in Parkinson disease and Alzheimer disease," Oncotarget, vol. 6, No. 35, p. 37043, 37047, (2015).
Marcus et al., "Targeting Post-translational Modifications on Tau as a Therapeutic Strategy for Alzheimer's Disease," Journal of Neurogenetics, vol. 25, No. 4, pp. 127-133, (2011), DOI: https://doi.org/10.310901677063.2011.626471. Abstract Only.
Prince et al., World Alzheimer's Report 2015, Alzheimer's Disease International, (2015).

(Continued)

Primary Examiner — Amanda Haney
(74) Attorney, Agent, or Firm — Hoxie & Associates LLC

(57) ABSTRACT

The present invention describes a method for the diagnosis of a cognitive disorder including but not limited to Alzheimer disease in a subject at risk of having or developing a cognitive disorder.

3 Claims, 12 Drawing Sheets
Specification includes a Sequence Listing.

(56) References Cited

OTHER PUBLICATIONS

Satoh, et al., "MicroRNA-Seq Data Analysis Pipeline to Identify Blood Biomarkers for Alzheimer's Disease from Public Data," *Biomarker Insights*, vol. 10, No. 15, pp. 22, 23, 27, 30, (2015), DOI: 10.4137/BMI.S25132.

Shankar et al., "Transcriptome analysis in different rice cultivars provides novel insights into desiccation and salinity stress responses," *Scientific Reports*, vol. 6, No. 1, (2016), DOI: 10.1038/srep23719.

Siemers et al., "Phase 3 solanezumab trials: Secondary outcomes in mild Alzheimer's disease patients," *Alzheimer's & Dementia Journal*, vol. 12, No. 2, pp. 110-120, (2016), DOI: http://dx.doi.org/10.1016/j.jalz.2015.06.1893.

Soreq et al., "Long Non-Coding RNA and Alternative Splicing Modulations in Parkinson's Leukocytes Identified by RNA Sequencing," *PLOS Computational Biology*, vol. 10, No. 3, p. 1003517, (2014).

Sunderland et al., "Decreased β-Amyloid 1-42 and Increased Tau Levels in Cerebrospinal Fluid of Patients With Alzheimer Disease," *JAMA*, vol. 289, No. 16, pp. 2094-2103, (2003).

Tahmasian et al., "Based on the Network Degeneration Hypothesis: Separating Individual Patients with Different Neurodegenerative Syndromes in a Preliminary Hybrid PET/MR Study," *Journal of Nuclear Medicine*, vol. 57, No. 3, pp. 410-415, (2016), DOI: 10.2967/jnumed.115.165464.

Wong et al., "In Vivo Imaging of Amyloid Deposition in Alzheimer's Disease using the Novel Radioligand [18F]AV-45 (Florbetapir F 18)," *Journal of Nuclear Medicine*, vol. 51, No. 6, pp. 913-920, (2010), DOI: 10.2967/jnumed.109.069088.

Written Opinion of the International Search Authority for International Application No. PCT/EP2018/073905, 12 pages, Date of mailing as indicated by PCT/ISA/210 (second sheet) Dec. 11, 2018.

HTG Molecular Diagnostics, Inc., "HTG EdgeSeq miRNA Whole Transcriptome Assay", [retrieved on May 10, 2017], XP055830822, Retrieved from the Internet: URL: https://www.htgmolecular.com/pubsearch/pdf/S1HTGEdgeSeqmiRNAWTA.pdf.

Wang H.Y., et al. "Quantamatrix Multiplexed Assay Platform system for direct detection of bacteria and antibiotic resistance determinants in positive blood culture bottles," *Clin Microbiol Infect.* May 2017; 23(5):333.e1-333.e7.

Cogswell, et al., "Identification of miRNA changes in Alzheimer's disease brain and CSF yields putative biomarkers and insights into disease pathways.", *Journal of Alzheimer's disease*, vol. 14, p. 27-41, (2008).

Yang, et al., "Distinct Hippocampal Expression Profiles of Long Non-coding RNAs in an Alzheimer's Disease Model", *Mol. Neurobiol.*, vol. 54, No. 7, pp. 4833-4846, (2016).

Yaohui, et al., "Investigation of Long Non-coding RNA Expression Profiles in the Substantia Nigra of Parkinson's Disease", *Cell Mol. Neurobiol.*, vol. 37, No. 2, pp. 329-338, (2016).

Zhang, et al., "Preparation and application of streptavidin magnetic particles", *Sci. China Ser. B-Chem.*, vol. 50, No. 1, pp. 127-134, (2007).

\* cited by examiner

NON-CODING RNAS (NCRNA) FOR THE DIAGNOSIS OF COGNITIVE DISORDERS

CROSS REFERENCE TO RELATED APPLICATIONS

This application is a U.S. national stage application filed under 35 U.S.C. § 371 of International Application No. PCT/EP2018/073905, filed on Sep. 5, 2018, which claims the benefit and priority of U.S. provisional application 62/554,427, filed on Sep. 5, 2017, the contents of each of which are incorporated herein by reference in their entireties.

FIELD OF THE INVENTION

The present invention relates to the field of human medicine and specifically to the diagnosis of cognitive disorder including Alzheimer disease. This invention relates to a biomarker for cognitive disorders, in particular Alzheimer's disease, consisting of circulating non-coding RNAs (ncRNA) such as microRNA (miRNA) and long non-coding RNAs (lncRNA), or their combination in a peripheral body fluid and representing a non-invasive method for diagnosing the cognitive disorder in particular Alzheimer's disease or for monitoring its development or progression using this biomarker. It further relates to associated kits, methods, protocols and transmittable forms of information for diagnosis purposes and/or for other human medicine applications including the patient stratification in clinical trials and/or monitoring the efficacy of therapeutic strategies using this biomarker and peripheral body fluids from patients. The present invention will thus have a strong impact on the quality of life of patients and a significant impact on the healthcare system and economy.

BACKGROUND ART

Alzheimer's disease (AD) is a chronic neurodegenerative disease characterized by progressive loss of cognitive function and pathologically by extracellular deposition of amyloid-beta peptide (Aβ) and intracellular deposition of hyperphosphorylated tau protein in neurofibrillary tangles in the brain, associated with progressive neuronal degeneration (Marcus et al. J Neurogenet. 2011; 25(4):127-33; Gotz et al, Br J Pharmacol. 2012; 165(5):1246-59).

AD is the most common form of dementia. Approximately 46.8 million people worldwide currently live with AD or other type of dementia. With an ageing population, this number is estimated to increase to 131.5 million by 2050 (World Alzheimer Report, 2015: http://www.alz.co.uk/research/WorldAlzheimerReport2015.pdf). As such, AD is becoming an increasingly important burden on the affected individuals and their families as well as economic and social costs on medical and healthcare resources in both developed and emerging countries.

Currently, there is no cure for AD. Symptomatic treatments exist for this disease all trying to counterbalance neurotransmitter's disturbance. Although a number of new potential disease-modifying therapeutic candidates are currently being studied in clinical trials, none has been approved yet. From 2002 to 2012, there was a failure of 99.6% of AD clinical trials that were 289 Phases 2 and 3 trials on symptomatic agents (36.6%), disease-modifying small molecules (35.1%) and disease-modifying immuno-therapies (18%) (Cummings et al., Expert Rev Clin Pharmacol. 2014; 7(2):161-5). Among the strategies proposed by worldwide experts in the AD field and by pharmaceutical industries to improve the success rate for AD drug development, are: a) intervening earlier in the disease process before neurodegeneration begins, b) identifying and developing accurate biomarkers for early diagnosis, non-invasive and suitable for stratification of subject populations and for longitudinal monitoring of drug efficacy in clinical trials.

The AD pathological features are defined in post-mortem histopathological analysis. The presence of amyloid plaques remains an absolutely required feature for the definitive diagnosis of AD, as accepted by the American Academy of Neurology, American Psychiatric Association (DSM-IV) and both the CERAD and NIA-Reagan Institute neuropathological criteria.

Current diagnosis of the disease remains uncertain (Dubois et al Lancet Neurol. 2014; 13(6):614-29) and it is based on combination of battery of clinical and neuropsychological tests and neuroimaging, such as structural imaging using Magnetic Resonance Imaging (MRI) and/or glucose metabolism using Positron emission tomography (PET) of fluorodeoxyglucose F18 ($^{18}$F-FDG), with an accuracy of less than 70%-85% depending on the method and the severity stage of the disease (Frisoni et al., Nat Rev Neurol. 2010; 6(2): 67-77; Tahmasian et al., J Nucl Med. 2016; 57(3):410-5).

Sometimes, detection of AD-associated biomarkers Aβ42 and tau or phosphorylated-tau in cerebrospinal fluid (CSF) is additionally performed (Sunderland et al., JAMA. 2003; 289(16):2094-2103), but CSF tests request a lumbar puncture, which is an invasive procedure and often requires hospitalization of subjects. In addition, the accuracy of these CSF tests remains insufficient as up to 30% of subjects can be misdiagnosed and the test cannot be longitudinally practiced to be followed up for confirmation of diagnostic purposes.

Longitudinal confirmatory diagnosis test is essential for applications to early detection of the preclinical stages of AD and mild cognitive impairment (MCI; defined as an early stage during which the first subtle symptoms manifest) and thus detecting early and calculating the risk of conversion of MCI into AD. Due to its limits (invasive), a CSF test is not rarely used as a biomarker for early diagnosis in preclinical AD stages before symptoms appear, nor it is suitable as a companion biomarker repeatedly practiced at several time points in same subjects recruited in longitudinal clinical trials.

Recently, specific neuroimaging methods relevant for AD pathology are being developed, notably with ligands for in vivo amyloid-beta (Aβ) ligands for Positron Emission Tomography (PET) neuroimaging including F-18 florbetapir and F-18 flutemetamol which have been approved by FDA and/or EMA (Choi et al., 2009 and Wong et al., 2010). However, their practice is costly and very limited (available only in some hospitals of large cities equipped with PET technology, still mainly for research purposes as not reimbursed by health insurances) and their diagnosis accuracy is still under studies for further understanding. Thus, the use of these Aβ PET neuroimaging methods remains very limited and the vast majority of patients do not profit from such tests even in rich countries.

There is a need for better definition of AD patient population to be included for the drug-development trials: PET imaging using Aβ ligands showed that up to 30% of subjects diagnosed with AD show a negative Aβ scan and that up to 35% of subjects with normal cognition status show a positive Aβ scan (Gaël Chételat et al, NeuroImage Clinical 2013; 2:356-65). Thus, PET Aβ scan is being used to guide for recruitment of subjects in the desired cohorts in some clinical trials by the large pharmaceutical companies. Anti-Aβ antibody e.g. Solanezumab tested in patients with mixed mild to moderate AD failed to show clear efficacy, however with some encouraging data in only mild AD patients subgroup. In mild AD patients selected based on CSF biomarker profile, the results showed a promising efficacy (Carlson et al., Alzheimers Dement (Amst). 2016; 2:75-85; Siemers et al., Alzheimers Dement. 2016; 12(2):110-20). However, the use of CSF biomarker is invasive, dramatically limiting its use as a biomarker for drug development. For example, it is not suitable for repeated use to monitor the stability and/or the progression of the disease, nor it is suitable to monitor in clinical longitudinal trials the efficacy of disease-modifying therapeutic drug candidates or preventive strategies.

Overall, the existing tests either lack an easy accessibility and simplicity for use for diagnosis of the large AD population and/or lack accuracy (sensitivity and specificity). This represents a major impediment and bottleneck to develop reliable and rapid diagnosis test for AD. Another impediment is the identification of a biomarker that does not require invasive sample collecting, such as a spinal tap. The lack of such an accessible, sensitive and specific biomarker that could be validated by cellular, animal model, pre-clinical models, and human testing impedes the development of therapies and drugs for AD or for the studies on pathological processes triggering AD or involved in the progression of AD.

Today, clearly there is an unmet need for an accurate and non-invasive peripheral biomarker test for diagnosis of AD including preclinical and early AD and for applications in drug development (patient stratification and monitoring drug efficacy in clinical trials).

ncRNAs include small microRNAs (miRNAs) and long non-coding RNAs (lncRNAs).

miRNAs are small non-coding RNA molecules (18-23 nucleotide) that modulate gene expression negatively at the post-transcriptional level. About 70% of the currently identified miRNAs are expressed in the brain. miRNAs play a major role in neural development, differentiation and synaptic plasticity. Some specific miRNAs are aberrantly expressed in AD brain, CSF and blood (for review: Hu et al., 2016, Front Aging Neurosci. 9(8):13), revealing their potential value in the diagnosis of AD.

lncRNAs are typically defined as transcripts longer than 200 nucleotides and expressed in a tissue-specific manner. In the brain, lncRNAs can regulate gene expression at epigenetic, transcriptional, and posttranscriptional levels of proteins with diverse functions including neuronal transmission and synaptic plasticity. Recent studies identified lncRNA candidates in AD postmortem brain tissue; some lncRNA candidates directly or indirectly regulate the formation of the neurotoxic Aβ, synaptic activity or the neuronal DNA repair (for review: Luo K and Chen Y, Clin Interv Aging 2016; 11: 867-872).

Expression levels of miRNAs may have potential as diagnostic biomarkers as they are known to circulate and tissue specific profiles can be identified in a number of body fluids such as plasma, CSF and urine. Recent developments in deep sequencing technology present a viable approach to develop biomarker pipelines in order to profile peripheral miRNA signatures specific to neurodegenerative diseases.

We previously showed that the lncRNAs expressed or highly enriched in tissues such as cardiac tissue or brain tissue, can be released into the peripheral circulation and be easily quantifiable by classical RT-PCR in different peripheral samples (PCT/EP2018/065492). In addition of the RT-PCR, we performed also total RNA sequencing on peripheral samples and quantified significant proportion of lncRNAs in the peripheral samples such as serum, plasma and Paxgene-RNA-tube collected whole blood (PCT/EP2018/065492).

According to the invention, new miRNA signatures and lncRNA signatures specific of neurodegenerative diseases, especially of AD, have been identified, using a method set up combining most recent technology and samples collected in non-invasively manner, including Paxgene whole blood tube, serum and plasma.

DESCRIPTION OF THE INVENTION

Figure 1:
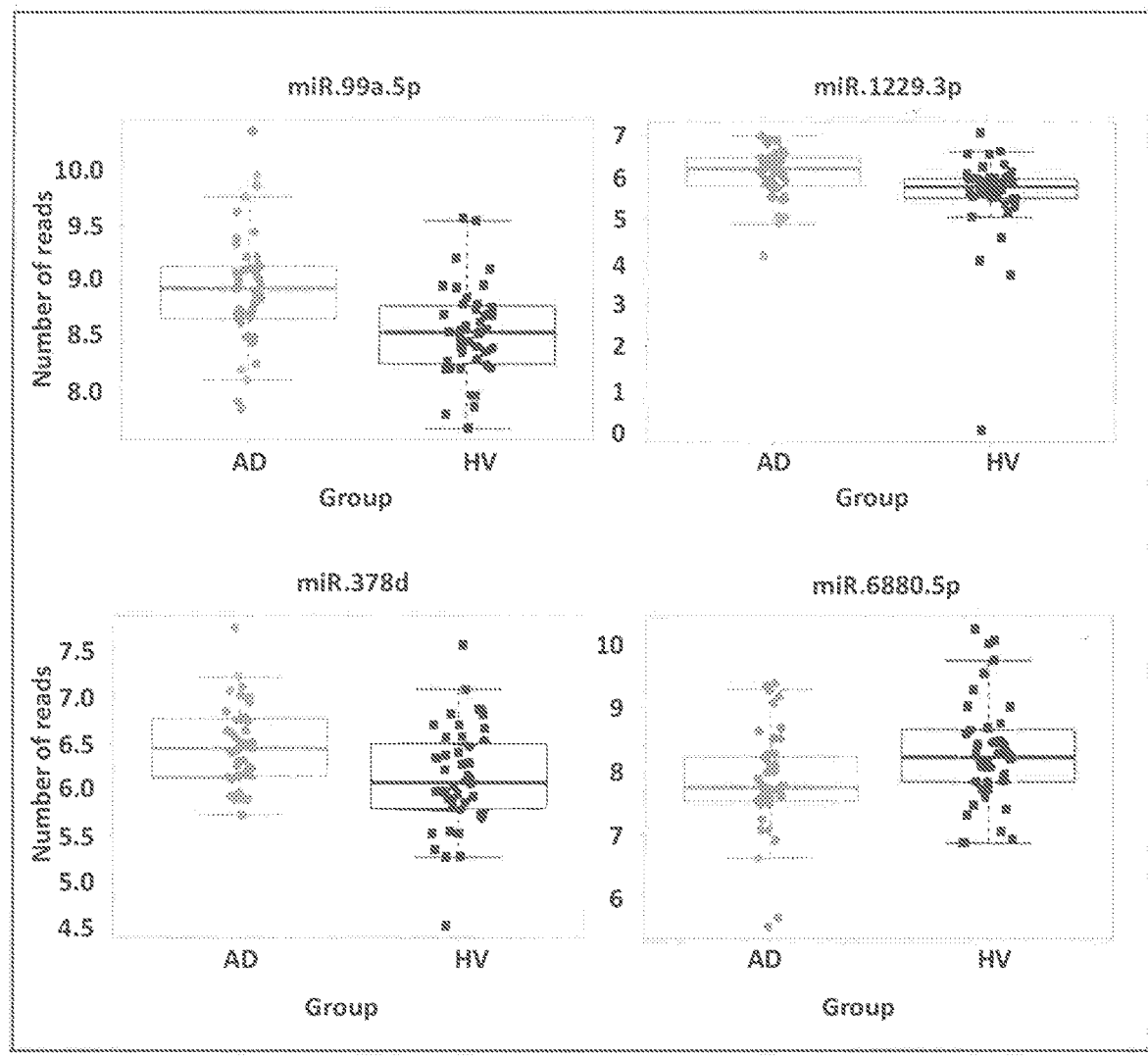
FIG. 1 shows the expression level of miR.99a.5p, MiR.1229.3p, miR.378d and miR.6880.5p on human plasma lithium heparin samples from patients with early to moderate Alzheimer (AD) and age-matched healthy controls. Y axis: mean+/−SD of the mean of concentration of the miRNAs in log 2 of the normalized number of reads. X axis: AD: Alzheimer patient group, HV: Healthy control group.

The invention relates to a method for the diagnosis of a cognitive disorder including but not limited to Alzheimer disease in a subject at risk of having or developing mild cognitive impairment or a cognitive disorder, comprising:
  (a) isolating a biological sample from the subject;
  (b) detecting a level of expression in a ncRNA (miRNA and/or lncRNA) signature, the ncRNA signature comprising or consisting of at least one ncRNA (miRNA and/or lncRNA) selected from 406 miRNAs listed in Table 1 and 1008 lncRNAs listed in Table 5 in the biological sample from said subject;
  (c) comparing the level of expression of miRNA and/or lncRNA in the sample to a level of expression in a reference, wherein an increased or decreased level of expression in the sample compared to the level in the reference identifies the subject having a cognitive disorder or being at risk of developing a cognitive disorder.

In some embodiments, the ncRNA signature comprises or consists of ncRNAs selected from the group consisting of:
  (i) miR.99a.5p;
  (ii) 7 miRNAs of miR.99a.5p, miR.378d, miR.100.5p, miR.193b.3p, miR.34a.5p, miR.1306.5p, and miR.1229.3p;
  (iii) 3 miRNAs of miR1220.3p, miR378d and miR99a.5p;
  (iv) 11 mRNAs of miR.99a.5p, miR.1229.3p, miR.100.5p, miR.378d, miR.193b.3p, miR.1306.5p, miR.195.5p, miR.532.3p, miR.125b.5p, miR.34a.5p, and miR.6880.5p;
  (v) 15 miRNAs of miR.23a.5p, miR.6880.5p, miR.7111.5p, miR.6812.5p, miR.6738.5p, miR.5196.5p, miR.6894.5p, miR.8085, miR.4463, miR.2392, miR.144.3p, miR.192.5p, miR.193b.3p, miR.194.5p, and miR.122.5p;
  (vi) 13 lncRNAs of lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20;
  (vii) 7 lncRNAs of LINCO2345:11, lnc-EBLN1-1:4, lnc-TPPP-1:2, lnc-TENM3-3:3, lnc-FAT1-7:2, lnc-DKK1-5:3, and lnc-TACSTD2-2:4;
  (viii) 12 lncRNAs of lnc-TPPP-1:2, ARRDC3-AS1:7, lnc-TENM3-3:5, lnc-TENM3-3:4, lnc-QRFP-5:1, lnc-CRYBB1-1:1, lnc-MGST3-1:3, lnc-FAM49B-8:1, HAND2-AS1:70, lnc-TMEM185B-12:7, lnc-CNDP1-7:1, and lnc-C21orf58-1:2;
  (ix) 3 lncRNAs of lnc-TENM3-3:3, lnc-MARCH4-2:7, and lnc-LRRC1-5:2;
  (x) 7 lncRNAs of lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46;
  (xi) 18 lncRNAs of lnc-TPPP-1:2, LINCO2345:11, lnc-ZNF273-4:4, lnc-TACC2-8:6, LINC01206:20, lnc-C5orf67-3:1, HAND2-AS1:58, lnc-PRDM9-20:1, lnc-CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, and lnc-AKR1E2-15:1;
  (xii) 28 miRNAs listed in Table 2;
  (xiii) 74 miRNAs listed in Table 3;
  (xiv) 33 lncRNAs listed in Table 6;
  (xv) 60 lncRNAs listed in Table 7;
  (xvi) 32 lncRNAs listed in Table 8;
  (xvii) 84 lncRNAs listed in Table 9; and
  (xviii) 94 lncRNAS listed in Table 10.

The invention also relates to a method for monitoring the development or progression of a cognitive disorder in a subject suffering from a loss or impairment of cognitive function or dementia, said method comprising the following steps:
  (a) isolating a biological sample from the subject;
  (b) detecting a level of expression in a ncRNA signature, the ncRNA signature comprising or consisting of at least one ncRNA (miRNA and/or lncRNA) selected from 406 miRNAs listed in Table 1 and 1008 lncRNAs listed in Table 5 in the biological sample;
  (c) comparing the level of expression of miRNA and/or lncRNA in the sample to a level of expression in a reference, wherein an increased or decreased level of expression in the sample compared to the level in the reference identifies the subject having a cognitive disorder or being at risk of developing a cognitive disorder, and
  (d) designing the therapeutic treatment according to the said identified cognitive disorder.

In some embodiments, the ncRNA signature comprises or consists of ncRNAs selected from the group consisting of:
  (i) miR.99a.5p;
  (ii) 7 miRNAs of miR.99a.5p, miR.378d, miR.100.5p, miR.193b.3p, miR.34a.5p, miR.1306.5p, and miR.1229.3p;
  (iii) 3 miRNAs of miR1220.3p, miR378d and miR99a.5p;
  (iv) 11 mRNAs of miR.99a.5p, miR.1229.3p, miR.100.5p, miR.378d, miR.193b.3p, miR.1306.5p, miR.195.5p, miR.532.3p, miR.125b.5p, miR.34a.5p, and miR.6880.5p;
  (v) 15 miRNAs of miR.23a.5p, miR.6880.5p, miR.7111.5p, miR.6812.5p, miR.6738.5p, miR.5196.5p, miR.6894.5p, miR.8085, miR.4463, miR.2392, miR.144.3p, miR.192.5p, miR.193b.3p, miR.194.5p, and miR.122.5p;
  (vi) 13 lncRNAs of lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20;
  (vii) 7 lncRNAs of LINCO2345:11, lnc-EBLN1-1:4, lnc-TPPP-1:2, lnc-TENM3-3:3, lnc-FAT1-7:2, lnc-DKK1-5:3, and lnc-TACSTD2-2:4;
  (viii) 12 lncRNAs of lnc-TPPP-1:2, ARRDC3-AS1:7, lnc-TENM3-3:5, lnc-TENM3-3:4, lnc-QRFP-5:1, lnc-CRYBB1-1:1, lnc-MGST3-1:3, lnc-FAM49B-8:1, HAND2-AS1:70, lnc-TMEM185B-12:7, lnc-CNDP1-7:1, and lnc-C21orf58-1:2;

(ix) 3 lncRNAs of lnc-TENM3-3:3, lnc-MARCH4-2:7, and lnc-LRRC1-5:2;
(x) 7 lncRNAs of lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46;
(xi) 18 lncRNAs of lnc-TPPP-1:2, LINCO2345:11, lnc-ZNF273-4:4, lnc-TACC2-8:6, LINC01206:20, lnc-C5orf67-3:1, HAND2-AS1:58, lnc-PRDM9-20:1, lnc-CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, and lnc-AKR1E2-15:1;
(xii) 28 miRNAs listed in Table 2;
(xiii) 74 miRNAs listed in Table 3;
(xiv) 33 lncRNAs listed in Table 6;
(xv) 60 lncRNAs listed in Table 7;
(xvi) 32 lncRNAs listed in Table 8;
(xvii) 84 lncRNAs listed in Table 9; and
(xviii) 94 lncRNAS listed in Table 10.

A biological sample may be a small part of a subject obtained from a body fluid, e.g. blood, plasma, serum, urine or cerebrospinal fluid. Suitably the biological sample are plasma or serum or Paxgene-RNA-tube.

By cognitive disorder is meant e.g. progressive impairment or progressive loss of a cognitive function, for example AD.

For Diagnosis of Cognitive Impairment or Dementia:

The "reference" may be suitable control sample such as for example a sample from a normal, healthy subject having no cognitive impairment symptoms and no abnormal neuroimaging findings and being age-matched to the patient to be diagnosed with the method of the present invention. The reference may be a sample from the same subject prior to demonstration of disorder or disease symptoms or prior to diagnosis of the impairment or loss of cognitive function or dementia. The reference may be a standardized sample, e.g. a sample comprising material or data from several samples of healthy subjects who have no cognitive impairment symptoms and no abnormal neuroimaging findings.

For Differential Diagnosis of a Specific Dementia Type or its Mild Cognitive Impairment (MCI) Versus Other Dementia Types and their MCI:

Dementia types and subtypes are numerous and include e.g.

Alzheimer (AD) and MCI of AD type
Frontotemporal dementia (FTD) and MCI of FTD type
Dementia with Lewy body (DLB) and MCI of DLB type
Parkinson's disease dementia (PDD) and MCI of PDD type
Vascular dementia
Progressive supranuclear palsy (PSP),
Corticobasal degeneration (CBD)

For differential diagnosis of one dementia subtype, the reference sample may be sample(s) from patient(s) suffering dementia of other type(s). For example, for differential diagnosis of AD or MCI of AD type, the sample(s) shall be from patient(s) with MCI/dementia of non-AD type (i.e. sample(s) from subject(s) with FTD and/or DLB and/or PDD and/or vascular dementia and/or PSP and/or CBD and/or other dementia), or from subject(s) who may suffer another disease but have no cognitive impairment or dementia.

The invention also relates to a method of diagnosing a cognitive disorder including but not limited to Alzheimer disease and monitoring its development or progression in a subject suffering from progressive impairment or loss of cognitive function or dementia, comprising:

(a) determining the presence of a cognitive disorder using a biological sample of the said subject using a method according to the invention, and (b) adapting a therapeutic treatment in function of the results of step (a).

The invention also relates to a method of diagnosing a cognitive disorder including but not limited to early MCI and very mild Alzheimer disease in a subject with no apparent and/or no measurable symptoms when using the available methods such as MMSE, MoCA and other neurocognitive tests, but with abnormal changes of biomarkers of the present invention preceding the symptoms, comprising:

(a) determining the risk of developing a cognitive disorder using a biological sample of the said subject using a method according to the invention, and (b) adapting a therapeutic treatment in function of the results of step (a).

The invention further relates to a method of predictive diagnosing a cognitive disorder including but not limited to early MCI and very mild Alzheimer disease in a subject with no apparent and/or no measurable abnormality by neuroimaging methods as MRI and/or CT scans, comprising:

(a) determining the risk of developing a cognitive disorder using a biological sample of the said subject using a method according to the invention, and (b) adapting a therapeutic treatment in function of the results of step (a).

The invention also relates to a method for treating a subject suffering from a progressive impairment or loss of cognitive function or dementia, said method comprising:

(a) diagnosing the cognitive disorder associated to the progressive impairment or loss of cognitive function or dementia in said patient using the method according to the invention, and (b) adapting the therapeutic treatment to the results obtained in step (a).

Examples of therapeutic treatment of cognitive disorders may comprise the administration of:

a drug already approved for treatment of cognitive disorders in particular Alzheimer's disease, e.g. cholinesterase inhibitors, for example donenepezil, rivastigmine or galantamine, or a NMDA receptor antagonist, e.g. memantine, or a combination of drugs, for example donepezil and memantine, and/or a novel therapeutic candidate or combination under clinical development, for example as currently tested in the anti-amyloid field, e.g. beta-secretase inhibitors and anti-beta-amyloid monoclonal antibodies, and anti-tau approaches, for example as currently tested in the anti-tau field, e.g. modulators of kinases or phosphatases that regulate tau phosphorylation status and anti-tau antibodies; and drug candidates modulating the molecular pathways such as neurodegeneration, synaptic plasticity, oxidative stress, autophagy, mitochondrial dysfunction and immuno-inflammation pathways where ncRNAs of the present invention are implicated.

Furthermore, the invention comprises a kit for diagnosing and/or monitoring a cognitive disorder including but not limited to AD, comprising at least one reagent for the determination of a ncRNA expression profile comprising or consisting of at least one ncRNA (miRNA and/or lncRNA) selected from 406 miRNAs listed in Table 1 and 1008 lncRNAs listed in Table 5 in the biological sample.

In some embodiments, the ncRNA expression profile comprises or consists of ncRNAs selected from the group consisting of:
(i) miR.99a.5p;
(ii) 7 miRNAs of miR.99a.5p, miR.378d, miR.100.5p, miR.193b.3p, miR.34a.5p, miR.1306.5p, and miR.1229.3p;
(iii) 3 miRNAs of miR1220.3p, miR378d and miR99a.5p;
(iv) 11 mRNAs of miR.99a.5p, miR.1229.3p, miR.100.5p, miR.378d, miR.193b.3p, miR.1306.5p, miR.195.5p, miR.532.3p, miR.125b.5p, miR.34a.5p, and miR.6880.5p;
(v) 15 miRNAs of miR.23a.5p, miR.6880.5p, miR.7111.5p, miR.6812.5p, miR.6738.5p, miR.5196.5p, miR.6894.5p, miR.8085, miR.4463, miR.2392, miR.144.3p, miR.192.5p, miR.193b.3p, miR.194.5p, and miR.122.5p;
(vi) 13 lncRNAs of lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20;
(vii) 7 lncRNAs of LINCO2345:11, lnc-EBLN1-1:4, lnc-TPPP-1:2, lnc-TENM3-3:3, lnc-FAT1-7:2, lnc-DKK1-5:3, and lnc-TACSTD2-2:4;
(viii) 12 lncRNAs of lnc-TPPP-1:2, ARRDC3-AS1:7, lnc-TENM3-3:5, lnc-TENM3-3:4, lnc-QRFP-5:1, lnc-CRYBB1-1:1, lnc-MGST3-1:3, lnc-FAM49B-8:1, HAND2-AS1:70, lnc-TMEM185B-12:7, lnc-CNDP1-7:1, and lnc-C21orf58-1:2;
(ix) 3 lncRNAs of lnc-TENM3-3:3, lnc-MARCH4-2:7, and lnc-LRRC1-5:2;
(x) 7 lncRNAs of lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46;
(xi) 18 lncRNAs of lnc-TPPP-1:2, LINCO2345:11, lnc-ZNF273-4:4, lnc-TACC2-8:6, LINC01206:20, lnc-C5orf67-3:1, HAND2-AS1:58, lnc-PRDM9-20:1, lnc-CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, and lnc-AKR1E2-15:1;
(xii) 28 miRNAs listed in Table 2;
(xiii) 74 miRNAs listed in Table 3;
(xiv) 33 lncRNAs listed in Table 6;
(xv) 60 lncRNAs listed in Table 7;
(xvi) 32 lncRNAs listed in Table 8;
(xvii) 84 lncRNAs listed in Table 9; and
(xviii) 94 lncRNAS listed in Table 10.

The kit of the invention allows performing the measurement of the miRNA signature and/or the lncRNA signature of the invention, wherein the kit comprises at least one reagent for measuring at least one ncRNA (miRNA and/or lncRNA) as indicated above.

By "reagent" is meant a reagent which specifically allows the determination of the miRNA/gene expression profile, i.e. a reagent specifically intended for the specific determination of the expression level of the miRNA/gene present in the miRNA/gene expression profile. Examples include e.g. amplification primer pairs (forward and reward) and/or probes specific for the miRNA/gene present in the miRNA/gene expression profile. This definition excludes generic reagents useful for the determination of the expression level of any other miRNA/gene.

By "reagent" is also meant a reagent which specifically allows the determination of the lncRNA expression profile, i.e. a reagent specifically intended for the specific determination of the expression level of the lncRNA present in the lncRNA expression profile. Examples include e.g. amplification primer pairs (forward and reward) and/or probes specific for the lncRNA present in the lncRNA expression profile. This definition excludes generic reagents useful for the determination of the expression level of any other lncRNA.

In some embodiments, the kit for diagnosing and/or monitoring a cognitive disorder comprises one or more oligonucleotide probes specific for ncRNAs of interest and a reagent for purifying the probe-target nucleic acid complexes. The oligonucleotide probes comprise a sequence complementary to a region of the ncRNAs of interest. The oligonucleotide probes may be DNA or RNA. The oligonucleotide probes are preferably DNA. In a preferred embodiment, the oligonucleotide probes are biotinylated and the reagent for purifying the probe-target complexes is a streptavidin-coated substrate, e.g., a streptavidin-coated magnetic particle, e.g., T1 streptavidin coated magnetic bead. In a preferred embodiment, the ncRNAs of interest is lncRNAs. The length of oligonucleotide probes specific for lncRNAs may be from 30 to 80 nucleotides, e.g., from 40 to 70, from 40 to 60, or about 50 nucleotides.

A further embodiment of the invention relates to a targeted sequencing panel for next generation sequencing, comprising nucleic acids specific for at least one ncRNA (miRNA and/or lncRNA) selected from 406 miRNAs listed in Table 1 and 1008 lncRNAs listed in Table 5 in the biological sample.

In some embodiments, the at least one ncRNA (miRNA and/or lncRNA) comprises or consists of ncRNAs selected from the group consisting of:
(i) miR.99a.5p;
(ii) 7 miRNAs of miR.99a.5p, miR.378d, miR.100.5p, miR.193b.3p, miR.34a.5p, miR.1306.5p, and miR.1229.3p;
(iii) 3 miRNAs of miR1220.3p, miR378d and miR99a.5p;
(iv) 11 mRNAs of miR.99a.5p, miR.1229.3p, miR.100.5p, miR.378d, miR.193b.3p, miR.1306.5p, miR.195.5p, miR.532.3p, miR.125b.5p, miR.34a.5p, and miR.6880.5p;
(v) 15 miRNAs of miR.23a.5p, miR.6880.5p, miR.7111.5p, miR.6812.5p, miR.6738.5p, miR.5196.5p, miR.6894.5p, miR.8085, miR.4463, miR.2392, miR.144.3p, miR.192.5p, miR.193b.3p, miR.194.5p, and miR.122.5p;
(vi) 13 lncRNAs of lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20;
(vii) 7 lncRNAs of LINCO2345:11, lnc-EBLN1-1:4, lnc-TPPP-1:2, lnc-TENM3-3:3, lnc-FAT1-7:2, lnc-DKK1-5:3, and lnc-TACSTD2-2:4;
(viii) 12 lncRNAs of lnc-TPPP-1:2, ARRDC3-AS1:7, lnc-TENM3-3:5, lnc-TENM3-3:4, lnc-RFP-5:1, lnc-CRYBB1-1:1, lnc-MGST3-1:3, lnc-FAM49B-8:1, HAND2-AS1:70, lnc-TMEM185B-12:7, lnc-CNDP1-7:1, and lnc-C21orf58-1:2;
(ix) 3 lncRNAs of lnc-TENM3-3:3, lnc-MARCH4-2:7, and lnc-LRRC1-5:2;
(x) 7 lncRNAs of lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46;
(xi) 18 lncRNAs of lnc-TPPP-1:2, LINCO2345:11, lnc-ZNF273-4:4, lnc-TACC2-8:6, LINC01206:20, lnc-C5orf67-3:1, HAND2-AS1:58, lnc-PRDM9-20:1, lnc- CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, and lnc-AKR1E2-15:1;
(xii) 28 miRNAs listed in Table 2;
(xiii) 74 miRNAs listed in Table 3;
(xiv) 33 lncRNAs listed in Table 6;
(xv) 60 lncRNAs listed in Table 7;
(xvi) 32 lncRNAs listed in Table 8;
(xvii) 84 lncRNAs listed in Table 9; and
(xviii) 94 lncRNAS listed in Table 10.

The invention also relates to the applications of the method for development of new therapeutic strategies (drug candidates) tested in clinical trials for the treatment of a cognitive disorder including but not limited to Alzheimer disease, wherein the method can be used (a) before starting the treatment for the selection of patients who would then be recruited in clinical trial; thus the test will enhance the likelihood for treating patient population that benefits from the tested therapeutic strategy(ies) while avoiding recruitment of patient subpopulation patients who do not benefit from this tested new drug candidate(s) and/or (b) for monitoring the response(s) including efficacy of the tested therapeutic strategy(ies) once treatment with the new tested drug candidate starts.

In a further aspect, the invention also relates to methods of detection. For example, the invention contemplates a method for the detection of at least one ncRNA (miRNA and/or lncRNA). In one aspect, the method comprises:
(a) isolating a biological sample from the subject;
(b) detecting a level of expression in a ncRNA signature, the ncRNA signature comprising or consisting of at least one ncRNA selected from 406 miRNAs listed in Table 1 and 1008 lncRNAs listed in Table 5 in the biological sample from said subject.

In some embodiments, the ncRNA signature comprises or consists of ncRNAs selected from the group consisting of:
(i) miR.99a.5p;
(ii) 7 miRNAs of miR.99a.5p, miR.378d, miR.100.5p, miR.193b.3p, miR.34a.5p, miR.1306.5p, and miR.1229.3p;
(iii) 3 miRNAs of miR1220.3p, miR378d and miR99a.5p;
(iv) 11 mRNAs of miR.99a.5p, miR.1229.3p, miR.100.5p, miR.378d, miR.193b.3p, miR.1306.5p, miR.195.5p, miR.532.3p, miR.125b.5p, miR.34a.5p, and miR.6880.5p;
(v) 15 miRNAs of miR.23a.5p, miR.6880.5p, miR.7111.5p, miR.6812.5p, miR.6738.5p, miR.5196.5p, miR.6894.5p, miR.8085, miR.4463, miR.2392, miR.144.3p, miR.192.5p, miR.193b.3p, miR.194.5p, and miR.122.5p;
(vi) 13 lncRNAs of lnc-DLG5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20;
(vii) 7 lncRNAs of LINCO2345:11, lnc-EBLN1-1:4, lnc-TPPP-1:2, lnc-TENM3-3:3, lnc-FAT1-7:2, lnc-DKK1-5:3, and lnc-TACSTD2-2:4;
(viii) 12 lncRNAs of lnc-TPPP-1:2, ARRDC3-AS1:7, lnc-TENM3-3:5, lnc-TENM3-3:4, lnc-QRFP-5:1, lnc-CRYBB1-1:1, lnc-MGST3-1:3, lnc-FAM49B-8:1, HAND2-AS1:70, lnc-TMEM185B-12:7, lnc-CNDP1-7:1, and lnc-C21orf58-1:2;
(ix) 3 lncRNAs of lnc-TENM3-3:3, lnc-MARCH4-2:7, and lnc-LRRC1-5:2;
(x) 7 lncRNAs of lnc-TPPP-1:2, lnc-TENM3-3:3, lnc-TMEM185B-12:7, lnc-NAXD-6:5, lnc-HECA-6:1, lnc-COMMD6-10:1, and MIR29B2CHG:46;
(xi) 18 lncRNAs of lnc-TPPP-1:2, LINCO2345:11, lnc-ZNF273-4:4, lnc-TACC2-8:6, LINC01206:20, lnc-C5orf67-3:1, HAND2-AS1:58, lnc-PRDM9-20:1, lnc-CLK1-1:7, lnc-DNALI1-5:4, RORB-AS1:6, lnc-TPPP-1:3, lnc-BMS1-2:1, lnc-ADRB1-4:1, lnc-XXYLT1-5:1, MIR99AHG:104, LINC01748:17, and lnc-AKR1E2-15:1;
(xii) 28 miRNAs listed in Table 2;
(xiii) 74 miRNAs listed in Table 3;
(xiv) 33 lncRNAs listed in Table 6;
(xv) 60 lncRNAs listed in Table 7;
(xvi) 32 lncRNAs listed in Table 8;
(xvii) 84 lncRNAs listed in Table 9; and
(xviii) 94 lncRNAS listed in Table 10.

The expression level of miRNAs and/or lncRNAs may be determined by any technology known by a man skilled in the art. In particular, the expression level of miRNAs and/or lncRNAs is determined by measuring the amount of nucleic acid transcripts of each miRNA or lncRNAs. The amount of nucleic acid transcripts can be measured by any technology known by a man skilled in the art. The measure may be carried out directly on an extracted RNA sample or on retrotranscribed complementary DNA (cDNA) prepared from extracted RNA by technologies well-known in the art. From the RNA or cDNA sample, the amount of nucleic acid transcripts may be measured using any technology known by a man skilled in the art, including nucleic acid microarrays, quantitative PCR, sequencing (e.g., next generation sequencing), FIMAP quantification, and hybridization with a labeled probe.

In some embodiments, the expression level of miRNAs and/or lncRNAs is determined using sequencing, e.g., next generation sequencing. Sequencing may be carried out after converting extracted RNA to cDNA using reverse transcriptase or RNA molecules may be directly sequenced. In a particular embodiment, which should not be considered as limiting the scope of the invention, the measurement of the expression level using next generation sequencing may be performed as follows. Briefly, RNA is extracted from a sample (e.g., blood sample). After removing rRNA, RNA samples are then reverse transcribed into cDNA. To ensure strand specificity, single stranded cDNA is first synthetized using Super-Script II reverse transcriptase and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3'end adenylation step, adaptor is attached to cDNA. So obtained cDNA (sequencing library) may be amplified by PCR. The sequencing libraries can be sequenced by any next generation sequencing technology known by a man skilled in the art.

In some embodiments, the measurement of the expression level of ncRNAs, e.g., by sequencing (e.g., next generation sequencing), is facilitated by capturing and enriching nucleic acids (RNA or cDNA) corresponding to ncRNAs of interest prior to the measurement. As used herein, enrichment refers to increasing the percentage of the nucleic acids of interest in the sample relative to the initial sample by selectively purifying the nucleic acids of interest. The enrichment of nucleic acids corresponding to ncRNAs of interest can be carried out on extracted RNA sample or cDNA sample prepared from extracted RNA. In some embodiments, nucleic acids corresponding to ncRNAs of interest are captured and enriched by hybridizing RNA or cDNA sample to oligonucleotide probes specific for ncRNAs of interest (e.g. oligonucleotide probes comprising a sequence complementary to a region of ncRNAs of interest) under conditions allowing for hybridization of the probes and target nucleic acids to form probe-target nucleic acid complexes. Probes may be DNA or RNA, preferably DNA. The probe-target nucleic acid complexes can be purified by any technology known by a man skilled in the art. In a preferred embodiment, probes are biotinylated. The biotinylated probe-target nucleic acid complexes can be purified by using a streptavidin-coated substrate, e.g., a streptavidin-coated magnetic particle, e.g., T1 streptavidin coated magnetic bead. In a preferred embodiment, the ncRNAs measured by this method are lncRNAs. The length of probes specific for lncRNAs may be from 30 to 80 nucleotides, e.g., from 40 to 70, from 40 to 60, or about 50 nucleotides.

In some embodiments, the expression level of miRNAs and/or lncRNAs may be determined using quantitative PCR. Quantitative, or real-time, PCR is a well-known and easily available technology for those skilled in the art and does not need a precise description. In a particular embodiment, which should not be considered as limiting the scope of the invention, the determination of the expression profile using quantitative PCR may be performed as follows. Briefly, the real-time PCR reactions are carried out using the TaqMan Universal PCR Master Mix (Applied Biosystems). 6 µl cDNA is added to a 9 µl PCR mixture containing 7.5 µl TaqMan Universal PCR Master Mix, 0.75 µl of a 20× mixture of probe and primers and 0.75 µl water. The reaction consists of one initiating step of 2 min at 50 deg. C., followed by 10 min at 95 deg. C., and 40 cycles of amplification including 15 sec at 95 deg. C. and 1 min at 60 deg. C. The reaction and data acquisition can be performed using the ABI 7900HT Fast Real-Time PCR System (Applied Biosystems). The number of template transcript molecules in a sample is determined by recording the amplification cycle in the exponential phase (cycle threshold or $C_Q$ or $C_T$), at which time the fluorescence signal can be detected above background fluorescence. Thus, the starting number of template transcript molecules is inversely related to $C_T$.

In some embodiments, the expression level of miRNAs and/or lncRNAs may be determined by the use of a nucleic acid microarray. A nucleic acid microarray consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"). To determine the expression profile of a target nucleic acid sample, said sample is labelled, contacted with the microarray in hybridization conditions, leading to the formation of complexes between target nucleic acids that are complementary to probe sequences attached to the microarray surface. The presence of labelled hybridized complexes is then detected. Many variants of the microarray hybridization technology are available to the man skilled in the art.

In some embodiments, the expression level of miRNAs and/or lncRNAs may be determined by FIMAP quantification. Briefly, lncRNAs and miRNAs are amplified by PCR using primers with the same sequences as for qPCR that are chemically modified. Forward primers are phosphorylated in 5' and Reverse primers biotinylated in 5'. PCR products are digested with exonuclease to eliminate the phosphorylated strand and keep only the biotinylated ones. Biotinylated PCR products are incubated with coded silica microdisks coated with oligos complementary to the RNAs of interest (one code per target oligo), and hybridized products are revealed by addition of a fluorescent streptavidin conjugate. The expression level of miRNAs and/or lncRNAs is determined by measuring fluorescence signal.

In a still further aspect, the method of detection contemplates the use of a reagent to measure or detect the one or more miRNAs and/or one or more lncRNA. By "reagent" is meant a reagent that specifically allows the determination of the miRNA/gene or the lncRNA expression profile, i.e. a reagent specifically intended for the specific determination of the expression level of the miRNA/gene present in the miRNA/gene expression profile or the lncRNA present in the lncRNA expression profile. Examples include e.g. amplification primer pairs (forward and reward) and/or probes specific for the miRNA/gene present in the miRNA/gene expression profile and/or or the lncRNA present in the lncRNA expression profile. This definition excludes generic reagents useful for the determination of the expression level of any other miRNA/gene and generic reagents useful for the determination of the expression level of any other lncRNA.

In yet a further aspect, the method of detection comprises detecting one or more miRNAs and/or lncRNA from a biological sample, wherein the biological sample is selected from blood, plasma, serum, urine, cerebrospinal fluid, tear, saliva. In some embodiments, the biological sample is blood.

By "treating" or "treatment" of a subject being at risk to develop or having a cognitive disorder, particularly a progressive impairment or loss of cognitive function or dementia, e.g. AD, is meant administering or administration of a regimen to the subject in need thereof such that at least one symptom of the disorder or disease is cured, alleviated, remedied or improved. According to the present invention, depending on the diagnosing results, the subject is submitted to an adapted therapeutic treatment and is further monitored. The monitoring of the subject based on the miRNA signature and/or lncRNA signature of the invention allows to further adapt or modify the therapeutic treatment, e.g. increasing the drug amount, administering a combination of drugs to obtain a synergy effect, or replacing the drug by an effective amount of another drug.

The invention also relates to the modification of a therapeutic strategy in subjects suffering from cognitive disorder who have been diagnosed and/or monitored using a method for (in vitro) diagnosis or monitoring of a progressive impairment or loss of cognitive function or dementia according to the invention.

According to the invention, the miRNAs and/or the lncRNAs of the invention may be used in combination with one or more biomarkers currently used for diagnosing a cognitive disorder including but not limited to AD. Examples of such biomarkers include without any limitation the biomarkers as disclosed in U.S. Pat. Nos. 9,377,472, 7,897,786 and in U.S. Pat. No. 6,703,212, the contents thereof being included herein by reference. The method of the invention combining the miRNAs and/or the lncRNAs of the invention with one or more known biomarkers may allow enhanced accuracy of diagnosis; or differential diagnosis; and a more efficient and successful drug development, e.g. enhanced accuracy for patient stratification before recruitment in clinical trials and monitoring of the efficacy of approved therapies or novel drugs under development.

According to the invention, the miRNAs and/or the lncRNAs of the invention may be used in combination with one or more tests currently used for diagnosing a cognitive disorder including but not limited to AD and/or for differential diagnostic purposes. Examples of such tests include without any limitation the neuropsychological tests, such as MMSE, MoCA, and the neuroimaging methods, in particular volumetric MRI. The method of the invention combining the miRNAs and/or the lncRNAs of the invention with one or more known biomarkers may allow enhanced accuracy of diagnosis; or differential diagnosis; and a more efficient and successful drug development, e.g. enhanced accuracy for patient stratification before recruitment in clinical trials and monitoring of the efficacy of approved therapies or novel drugs under development.

To identify miRNA signatures involved specifically in the pathogenesis of AD and mild cognitive impairment (MCI) of AD type, a total of 2083 miRNAs in samples from different groups, including a group of patients with AD or MCI of AD type and group of cognitively intact healthy controls with no brain imaging abnormalities, have been screened. Subsequently miRNA profiling in all samples, 406 miRNAs have been detected above the threshold. By comparison of miRNA-expression levels measured in the samples of the different groups, the miRNA differentially expressed in the samples of the control group as compared to the expression level in the samples of patient group diagnosed as having AD or cognitive impairment of AD type (at the Neurology department of clinical site, based on neurocognitive and neuropsychological tests and neuroimaging tests and on cerebrospinal fluid biomarkers: beta-amyloid peptide 1-42 (Aβ42) and tau (total and/or phosphorylated) were identified as miRNA biomarker candidates.

To identify lncRNA signatures involved specifically in the pathogenesis of AD and mild cognitive impairment (MCI) of AD type, a total of 127802 lncRNAs in samples from different groups, including a group of patients with AD or MCI of AD type and group of cognitively intact healthy controls with no brain imaging abnormalities, have been screened. Subsequently lncRNA profiling in all samples, 19867 lncRNAs have been detected above the threshold. By comparison of lncRNA-expression levels measured in the samples of the different groups, the lncRNA differentially expressed in the samples of the control group as compared to the expression level in the samples of patient group diagnosed as having AD or cognitive impairment of AD type (at the Neurology department of clinical sites, based on neurocognitive and neuropsychological tests and neuroimaging tests and on cerebrospinal fluid biomarkers: beta-amyloid peptide 1-42 (Aβ42) and tau (total and/or phosphorylated) were identified as lncRNA biomarker candidates.

Expression levels were analyzed using a two-tailed Welch t test and/or Wilcoxon Mann-Whitney test between two groups. Significant differential expression was identified as p<0.05. Fold change and AUC (Area Under the Curve) are calculated for each miRNA and lncRNA and for each tested condition.

miRNA candidates were also selected when differential expression was determined based on fold-changes ≥1.49-fold or ≤0.75-fold changes and/or AUC>0.6 or <0.4, are indicated in Tables 2, 3 and 4.

lncRNA candidates were also selected when differential expression was determined based on fold-changes ≥1.6 (or ≤0.6) and/or an AUC≥0.80 (or <0.20), are indicated in Tables 6 and 7.

Random Forest algorithm (Breimann 2001, Breiman and Cutler 2001) was used to build the model and also used to select the top miRNAs and/or the top lncRNAs. A predictive model based on the combination of the top 2-20 miRNAs and/or lncRNAs enables to predict the disease with an accuracy of ≥80%.

Out of the 2083 miRNA measured, 406 miRNA showed expression levels above threshold. Sequences of the 406 miRNAs are shown in Table 1. These 406 miRNAs are also listed in the sequence listing included in this application.

TABLE 1

Sequences of 406 miRNAs

| miRNA | SEQ ID | Sequence |
| --- | --- | --- |
| let.7a.5p | SEQ 1009 | UGAGGUAGUAGGUUGUAUAGUU |
| let.7b.5p | SEQ 1010 | UGAGGUAGUAGGUUGUGUGGUU |
| let.7c.5p | SEQ 1011 | UGAGGUAGUAGGUUGUAUGGUU |
| let.7d.3p | SEQ 1012 | CUAUACGACCUGCUGCCUUUCU |
| let.7d.5p | SEQ 1013 | AGAGGUAGUAGGUUGCAUAGUU |
| let.7e.5p | SEQ 1014 | UGAGGUAGGAGGUUGUAUAGUU |
| let.7f.5p | SEQ 1015 | UGAGGUAGUAGAUUGUAUAGUU |
| let.7g.5p | SEQ 1016 | UGAGGUAGUAGUUUGUACAGUU |
| let.7i.5p | SEQ 1017 | UGAGGUAGUAGUUUGUGCUGUU |
| miR.100.5p | SEQ 1018 | AACCCGUAGAUCCGAACUUGUG |
| miR.101.3p | SEQ 1019 | UACAGUACUGUGAUAACUGAA |
| miR.103a.2.5p | SEQ 1020 | AGCUUCUUUACAGUGCUGCCUUG |
| miR.103a.3p | SEQ 1021 | AGCAGCAUUGUACAGGGCUAUGA |
| miR.106a.5p | SEQ 1022 | AAAAGUGCUUACAGUGCAGGUAG |
| miR.106b.3p | SEQ 1023 | CCGCACUGUGGGUACUUGCUGC |
| miR.106b.5p | SEQ 1024 | UAAAGUGCUGACAGUGCAGAU |
| miR.107 | SEQ 1025 | AGCAGCAUUGUACAGGGCUAUCA |
| miR.10a.5p | SEQ 1026 | UACCCUGUAGAUCCGAAUUUGUG |
| miR.10b.5p | SEQ 1027 | UACCCUGUAGAACCGAAUUUGUG |
| miR.1202 | SEQ 1028 | GUGCCAGCUGCAGUGGGGGAG |
| miR.1207.5p | SEQ 1029 | UGGCAGGGAGGCUGGGAGGGG |
| miR.122.5p | SEQ 1030 | UGAGCCCCUGUGCCGCCCCCAG |
| miR.1225.3p | SEQ 1031 | GUGGGUACGGCCCAGUGGGGGG |
| miR.1225.5p | SEQ 1032 | UGGAGUGUGACAAUGGUGUUUG |
| miR.1228.3p | SEQ 1033 | UCACACCUGCCUCGCCCCCC |
| miR.1229.3p | SEQ 1034 | CUCUCACCACUGCCCUCCCACAG |
| miR.1233.3p | SEQ 1035 | UGAGCCCUGUCCUCCCGCAG |
| miR.1234.3p | SEQ 1036 | UCGGCCUGACCACCCACCCCAC |
| miR.1237.5p | SEQ 1037 | CGGGGGCGGGGCCGAAGCGCG |
| miR.1244 | SEQ 1038 | AAGUAGUUGGUUUGUAUGAGAUGGUU |
| miR.1247.3p | SEQ 1039 | CCCCGGGAACGUCGAGACUGGAGC |
| miR.1249 | SEQ 1040 | AGGAGGGAGGAGAUGGGCCAAGUU |
| miR.1254 | SEQ 1041 | AGCCUGGAAGCUGGAGCCUGCAGU |

TABLE 1-continued

Sequences of 406 miRNAs

| miRNA | SEQ ID | Sequence |
|---|---|---|
| miR.1255b.2.3p | SEQ 1042 | AACCACUUUCUUUGCUCAUCCA |
| miR.125a.5p | SEQ 1043 | UCCCUGAGACCCUUUAACCUGUGA |
| miR.125b.5p | SEQ 1044 | UCCCUGAGACCCUAACUUGUGA |
| miR.126.3p | SEQ 1045 | UCGUACCGUGAGUAAUAAUGCG |
| miR.126.5p | SEQ 1046 | CAUUAUUACUUUUGGUACGCG |
| miR.1273a | SEQ 1047 | GGGCGACAAAGCAAGACUCUUUCUU |
| miR.1273c | SEQ 1048 | GGCGACAAAACGAGACCCUGUC |
| miR.1273d | SEQ 1049 | GAACCCAUGAGGUUGAGGCUGCAGU |
| miR.1273e | SEQ 1050 | UUGCUUGAACCCAGGAAGUGGA |
| miR.1273g.5p | SEQ 1051 | GGUGGUUGAGGCUGCAGUAAGU |
| miR.1273h.5p | SEQ 1052 | CUGGGAGGUCAAGGCUGCAGU |
| miR.1275 | SEQ 1053 | GUGGGGGAGAGGCUGUC |
| miR.128.3p | SEQ 1054 | UCACAGUGAACCGGUCUCUUU |
| miR.1285.5p | SEQ 1055 | GAUCUCACUUUGUUGCCCAGG |
| miR.1287.5p | SEQ 1056 | UGCUGGAUCAGUGGUUCGAGUC |
| miR.1290 | SEQ 1057 | UGGAUUUUUGGAUCAGGGA |
| miR.1291 | SEQ 1058 | UGGCCCUGACUGAAGACCAGCAGU |
| miR.1299 | SEQ 1059 | UUCUGGAAUUCUGUGUGAGGGA |
| miR.1301.3p | SEQ 1060 | UUGCAGCUGCCUGGGAGUGACUUC |
| miR.1303 | SEQ 1061 | UUUAGAGACGGGGUCUUGCUCU |
| miR.1304.3p | SEQ 1062 | UCUCACUGUAGCCUCGAACCCC |
| miR.1306.5p | SEQ 1063 | CCACCUCCCCUGCAAACGUCCA |
| miR.1307.3p | SEQ 1064 | ACUCGGCGUGGCGUCGGUCGUG |
| miR.1307.5p | SEQ 1065 | UCGACCGGACCUCGACCGGCU |
| miR.130a.3p | SEQ 1066 | CAGUGCAAUGUUAAAAGGGCAU |
| miR.130b.3p | SEQ 1067 | CAGUGCAAUGAUGAAAGGGCAU |
| miR.130b.5p | SEQ 1068 | ACUCUUUCCCUGUUGCACUAC |
| miR.134.5p | SEQ 1069 | UGUGACUGGUUGACCAGAGGGG |
| miR.136.5p | SEQ 1070 | ACUCCAUUUGUUUUGAUGAUGGA |
| miR.138.1.3p | SEQ 1071 | GCUACUUCACAACACCAGGGCC |
| miR.139.5p | SEQ 1072 | UCUACAGUGCACGUGUCUCCAGU |
| miR.140.5p | SEQ 1073 | CAGUGGUUUUACCCUAUGGUAG |
| miR.141.3p | SEQ 1074 | UAACACUGUCUGGUAAAGAUGG |
| miR.142.5p | SEQ 1075 | CAUAAAGUAGAAAGCACUACU |
| miR.143.3p | SEQ 1076 | UGAGAUGAAGCACUGUAGCUC |
| miR.144.3p | SEQ 1077 | UACAGUAUAGAUGAUGUACU |
| miR.144.5p | SEQ 1078 | GGAUAUCAUCAUAUACUGUAAG |
| miR.145.5p | SEQ 1079 | GUCCAGUUUUCCCAGGAAUCCCU |
| miR.146a.5p | SEQ 1080 | UGAGAACUGAAUUCCAUGGGUU |
| miR.146b.5p | SEQ 1081 | UGAGAACUGAAUUCCAUAGGCU |
| miR.148a.3p | SEQ 1082 | UCAGUGCACUACAGAACUUUGU |
| miR.148b.3p | SEQ 1083 | UCAGUGCAUCACAGAACUUUGU |
| miR.149.3p | SEQ 1084 | AGGGAGGGACGGGGGCUGUGC |
| miR.150.5p | SEQ 1085 | UCUCCCAACCCUUGUACCAGUG |
| miR.151a.3p | SEQ 1086 | CUAGACUGAAGCUCCUUGAGG |
| miR.152.3p | SEQ 1087 | UCAGUGCAUGACAGAACUUGG |
| miR.154.5p | SEQ 1088 | UAGGUUAUCCGUGUUGCCUUCG |
| miR.155.5p | SEQ 1089 | UUAAUGCUAAUCGUGAUAGGGGU |
| miR.15a.5p | SEQ 1090 | UAGCAGCACAUAAUGGUUUGUG |
| miR.15b.5p | SEQ 1091 | UAGCAGCACAUCAUGGUUUACA |
| miR.16.5p | SEQ 1092 | UAGCAGCACGUAAAUAUUGGCG |
| miR.17.3p | SEQ 1093 | ACUGCAGUGAAGGCACUUGUAG |
| miR.17.5p | SEQ 1094 | CAAAGUGCUUACAGUGCAGGUAG |
| miR.181a.5p | SEQ 1095 | AACAUUCAACGCUGUCGGUGAGU |
| miR.181b.5p | SEQ 1096 | AACAUUCAUUGCUGUCGGUGGGU |
| miR.181c.5p | SEQ 1097 | AACAUUCAACCUGUCGGUGAGU |
| miR.181d.5p | SEQ 1098 | AACAUUCAUUGUUGUCGGUGGGU |
| miR.185.3p | SEQ 1099 | AGGGGCUGGCUUUCCUCUGGUC |
| miR.185.5p | SEQ 1100 | UGGAGAGAAAGGCAGUUCCUGA |
| miR.186.3p | SEQ 1101 | GCCCAAAGGUGAAUUUUUUGGG |
| miR.186.5p | SEQ 1102 | CAAAGAAUUCUCCUUUUGGGCU |
| miR.187.3p | SEQ 1103 | UCGUGUCUUGUGUUGCAGCCGG |
| miR.187.5p | SEQ 1104 | GGCUACAACACAGGACCCGGGC |
| miR.18a.5p | SEQ 1105 | UAAGGUGCAUCUAGUGCAGAUAG |
| miR.18b.5p | SEQ 1106 | UAAGGUGCAUCUAGUGCAGUUAG |
| miR.1908.5p | SEQ 1107 | CGGCGGGGACGGCGAUUGGUC |
| miR.191.5p | SEQ 1108 | UCUGCCCCUCCGCUGCUGCCA |
| miR.1913 | SEQ 1109 | GGAGGGGUCCCGCACUGGGAGG |
| miR.1914.3p | SEQ 1110 | CCCUGUGCCCGGCCACUUCUG |
| miR.1914.5p | SEQ 1111 | CCCCAGGGCGACGCGGCGGG |
| miR.1915.3p | SEQ 1112 | CAACGGAAUCCCAAAAGCAGCUG |
| miR.192.5p | SEQ 1113 | CUGACCUAUGAAUUGACAGCC |
| miR.193a.3p | SEQ 1114 | AACUGGCCUACAAAGUCCCAGU |
| miR.193a.5p | SEQ 1115 | UGGGUCUUUGCGGGCGAGAUGA |
| miR.193b.3p | SEQ 1116 | AACUGGCCCUCAAAGUCCCGCU |
| miR.194.5p | SEQ 1117 | UGUAACAGCAACUCCAUGUGGA |

TABLE 1-continued

Sequences of 406 miRNAs

| miRNA | SEQ ID | Sequence |
|---|---|---|
| miR.195.5p | SEQ 1118 | UAGCAGCACAGAAAUAUUGGC |
| miR.197.3p | SEQ 1119 | UUCACCACCUUCUCCACCCAGC |
| miR.197.5p | SEQ 1120 | CGGGUAGAGAGGGCAGUGGGAGG |
| miR.1976 | SEQ 1121 | CCUCCUGCCCUCCUUGCUGU |
| miR.199a.3p | SEQ 1122 | ACAGUAGUCUGCACAUUGGUUA |
| miR.199a.5p | SEQ 1123 | CCCAGUGUUCAGACUACCUGUUC |
| miR.19a.3p | SEQ 1124 | UGUGCAAAUCUAUGCAAAACUGA |
| miR.19b.3p | SEQ 1125 | UGUGCAAAUCCAUGCAAAACUGA |
| miR.204.3p | SEQ 1126 | GCUGGGAAGGCAAAGGGACGU |
| miR.205.5p | SEQ 1127 | UCCUUCAUUCCACCGGAGUCUG |
| miR.20a.5p | SEQ 1128 | UAAAGUGCUUAUAGUGCAGGUAG |
| miR.20b.5p | SEQ 1129 | CAAAGUGCUCAUAGUGCAGGUAG |
| miR.21.3p | SEQ 1130 | CUGUGCGUGUGACAGCGGCUGA |
| miR.21.5p | SEQ 1131 | AGCCCCUGCCCACCGCACACUG |
| miR.210.3p | SEQ 1132 | UUGGGGAAACGGCCGCUGAGUG |
| miR.210.5p | SEQ 1133 | CAUCAGAAUUCAUGGAGGCUAG |
| miR.2110 | SEQ 1134 | AGCUUCCAUGACUCCUGAUGGA |
| miR.2115.3p | SEQ 1135 | CAACACCAGUCGAUGGGCUGU |
| miR.2115.5p | SEQ 1136 | UAGCUUAUCAGACUGAUGUUGA |
| miR.22.3p | SEQ 1137 | AGCUACAUUGUCUGCUGGGUUUC |
| miR.22.5p | SEQ 1138 | AGCUACAUCUGGCUACUGGGU |
| miR.221.3p | SEQ 1139 | UGUCAGUUUGUCAAAUACCCCA |
| miR.222.3p | SEQ 1140 | CGUGUAUUUGACAAGCUGAGUU |
| miR.223.3p | SEQ 1141 | AAGCUGCCAGUUGAAGAACUGU |
| miR.223.5p | SEQ 1142 | CAAGUCACUAGUGGUUCCGUU |
| miR.224.5p | SEQ 1143 | AGUCUUCAGUGGCAAGCUUUA |
| miR.2392 | SEQ 1144 | UAGGAUGGGGGUGAGAGGUG |
| miR.23a.3p | SEQ 1145 | AUCACAUUGCCAGGGAUUUCC |
| miR.23a.5p | SEQ 1146 | GGGGUUCCUGGGGAUGGGAUUU |
| miR.23b.3p | SEQ 1147 | AUCACAUUGCCAGGGAUUACC |
| miR.24.2.5p | SEQ 1148 | UGCCUACUGAGCUGAAACACAG |
| miR.24.3p | SEQ 1149 | UGGCUCAGUUCAGCAGGAACAG |
| miR.25.3p | SEQ 1150 | CAUUGCACUUGUCUCGGUCUGA |
| miR.26a.5p | SEQ 1151 | UUCAAGUAAUCCAGGAUAGGCU |
| miR.26b.3p | SEQ 1152 | CCUGUUCUCCAUUACUUGGCUC |
| miR.26b.5p | SEQ 1153 | UUCAAGUAAUUCAGGAUAGGU |
| miR.27a.3p | SEQ 1154 | UUCACAGUGGCUAAGUUCCGC |
| miR.27a.5p | SEQ 1155 | AGGGCUUAGCUGCUUGUGAGCA |
| miR.27b.3p | SEQ 1156 | UUCACAGUGGCUAAGUUCUGC |
| miR.28.5p | SEQ 1157 | AAGGAGCUCACAGUCUAUUGAG |
| miR.2861 | SEQ 1158 | GGGGCCUGGCGGUGGGCGG |
| miR.29a.3p | SEQ 1159 | UAGCACCAUCUGAAAUCGGUUA |
| miR.29b.3p | SEQ 1160 | UAGCACCAUUUGAAAUCAGUGUU |
| miR.29c.3p | SEQ 1161 | UAGCACCAUUUGAAAUCGGUUA |
| miR.29c.5p | SEQ 1162 | UGACCGAUUUCUCCUGGUGUUC |
| miR.301a.3p | SEQ 1163 | CAGUGCAAUAGUAUUGUCAAAGC |
| miR.30a.5p | SEQ 1164 | UGUAAACAUCCUCGACUGGAAG |
| miR.30b.5p | SEQ 1165 | UGUAAACAUCCUACACUCAGCU |
| miR.30c.5p | SEQ 1166 | UGUAAACAUCCUACACUCUCAGC |
| miR.30d.5p | SEQ 1167 | UGUAAACAUCCCCGACUGGAAG |
| miR.30e.3p | SEQ 1168 | CUUUCAGUCGGAUGUUUACAGC |
| miR.30e.5p | SEQ 1169 | UGUAAACAUCCUUGACUGGAAG |
| miR.3135a | SEQ 1170 | UGCCUAGGCUGAGACUGCAGUG |
| miR.3140.3p | SEQ 1171 | AGCUUUUGGGAAUUCAGGUAGU |
| miR.3140.5p | SEQ 1172 | ACCUGAAUUACCAAAAGCUUU |
| miR.3141 | SEQ 1173 | GAGGGCGGGUGGAGGAGGA |
| miR.3157.5p | SEQ 1174 | UUCAGCCAGGCUAGUGCAGUCU |
| miR.3162.5p | SEQ 1175 | UUAGGGAGUAGAAGGGUGGGGAG |
| miR.3180.3p | SEQ 1176 | UGGGGCGGAGCUUCCGGAGGCC |
| miR.3197 | SEQ 1177 | GGAGGCGCAGGCUCGGAAAGGCG |
| miR.320a | SEQ 1178 | AAAAGCUGGGUUGAGAGGGCGA |
| miR.320b | SEQ 1179 | AAAAGCUGGGUUGAGAGGGCAA |
| miR.320c | SEQ 1180 | AAAAGCUGGGUUGAGAGGGU |
| miR.320d | SEQ 1181 | AAAAGCUGGGUUGAGAGGA |
| miR.320e | SEQ 1182 | AAAGCUGGGUUGAGAAGG |
| miR.324.3p | SEQ 1183 | ACUGCCCCAGGUGCUGCUGG |
| miR.324.5p | SEQ 1184 | CGCAUCCCCUAGGGCAUUGGUGU |
| miR.326 | SEQ 1185 | CCUCUGGGCCCUUCCUCCAG |
| miR.328.3p | SEQ 1186 | CUGGCCCUCUCUGCCCUUCCGU |
| miR.329.3p | SEQ 1187 | AACACACCUGGUUAACCUCUUU |
| miR.331.3p | SEQ 1188 | GCCCCUGGGCCUAUCCUAGAA |
| miR.335.5p | SEQ 1189 | UCAAGAGCAAUAACGAAAAAUGU |
| miR.337.5p | SEQ 1190 | GAACGGCUUCAUACAGGAGUU |
| miR.338.3p | SEQ 1191 | UCCAGCAUCAGUGAUUUUGUUG |
| miR.339.3p | SEQ 1192 | UGAGCGCCUCGACGACAGAGCCG |
| miR.339.5p | SEQ 1193 | UCCCUGUCCUCCAGGAGCUCACG |

TABLE 1-continued

Sequences of 406 miRNAs

| miRNA | SEQ ID | Sequence |
|---|---|---|
| miR.33a.5p | SEQ 1194 | GUGCAUUGUAGUUGCAUUGCA |
| miR.33b.5p | SEQ 1195 | GUGCAUUGCUGUUGCAUUGC |
| miR.342.3p | SEQ 1196 | UCUCACACAGAAAUCGCACCCGU |
| miR.345.5p | SEQ 1197 | GCUGACUCCUAGUCCAGGGCUC |
| miR.34a.5p | SEQ 1198 | UGGCAGUGUCUUAGCUGGUUGU |
| miR.34b.3p | SEQ 1199 | CAAUCACUAACUCCACUGCCAU |
| miR.361.3p | SEQ 1200 | UCCCCCAGGUGUGAUUCUGAUUU |
| miR.361.5p | SEQ 1201 | UUAUCAGAAUCUCCAGGGGUAC |
| miR.362.5p | SEQ 1202 | AAUCCUUGGAACCUAGGUGUGAG |
| miR.363.3p | SEQ 1203 | AAUUGCACGGUAUCCAUCUGUAU |
| miR.3648 | SEQ 1204 | AGCCGCGGGGAUCGCCGAGGG |
| miR.3652 | SEQ 1205 | CGGCUGGAGGUGUGAGGA |
| miR.3663.5p | SEQ 1206 | GCUGGUCUGCGUGGUGCUCGG |
| miR.3674 | SEQ 1207 | AUUGUAGAACCUAAGAUUGGCC |
| miR.3687 | SEQ 1208 | CCCGGACAGGCGUUCGUGCGACGU |
| miR.370.3p | SEQ 1209 | GCCUGCUGGGGUGGAACCUGGU |
| miR.374b.5p | SEQ 1210 | AUAUAAUACAACCUGCUAAGUG |
| miR.375 | SEQ 1211 | UUUGUUCGUUCGGCUCGCGUGA |
| miR.376a.3p | SEQ 1212 | AUCAUAGAGGAAAAUCCACGU |
| miR.376c.3p | SEQ 1213 | AACAUAGAGGAAAUUCCACGU |
| miR.377.3p | SEQ 1214 | AUCACACAAAGGCAACUUUUGU |
| miR.378a.3p | SEQ 1215 | ACUGGACUUGGAGUCAGAAGGC |
| miR.378d | SEQ 1216 | ACUGGACUUGGAGUCAGAAA |
| miR.378f | SEQ 1217 | ACUGGACUUGGAGCCAGAAG |
| miR.378g | SEQ 1218 | ACUGGGCUUGGAGUCAGAAG |
| miR.378i | SEQ 1219 | ACUGGACUAGGAGUCAGAAGG |
| miR.381.3p | SEQ 1220 | UAUACAAGGGCAAGCUCUCUGU |
| miR.382.5p | SEQ 1221 | GAAGUUGUUCGUGGUGGAUUCG |
| miR.3912.3p | SEQ 1222 | UAACGCAUAAUAUGGACAUGU |
| miR.3912.5p | SEQ 1223 | AUGUCCAUAUUAUGGGUUAGU |
| miR.3937 | SEQ 1224 | ACAGGCGGCUGUAGCAAUGGGG |
| miR.3940.5p | SEQ 1225 | GUGGGUUGGGGCGGGCUCUG |
| miR.409.3p | SEQ 1226 | GAAUGUUGCUCGGUGAACCCCU |
| miR.410.3p | SEQ 1227 | AAUAUAACACAGAUGGCCUGU |
| miR.424.3p | SEQ 1228 | CAAAACGUGAGGCGCUGCUAU |
| miR.425.3p | SEQ 1229 | AUCGGGAAUGUCGUGUCCGCCC |
| miR.425.5p | SEQ 1230 | AAUGACACGAUCACUCCCGUUGA |
| miR.4257 | SEQ 1231 | CCAGAGGUGGGGACUGAG |
| miR.4270 | SEQ 1232 | UCAGGGAGUCAGGGGAGGGC |
| miR.4274 | SEQ 1233 | CAGCAGUCCCUCCCCCUG |
| miR.4279 | SEQ 1234 | CUCUCCUCCCGGCUUC |
| miR.4291 | SEQ 1235 | UUCAGCAGGAACAGCU |
| miR.4292 | SEQ 1236 | CCCCUGGGCCGGCCUUGG |
| miR.4306 | SEQ 1237 | UGGAGAGAAAGGCAGUA |
| miR.431.5p | SEQ 1238 | UGUCUUGCAGGCCGUCAUGCA |
| miR.432.5p | SEQ 1239 | UCUUGGAGUAGGUCAUUGGGUGG |
| miR.4417 | SEQ 1240 | GGUGGGCUUCCCGGAGGG |
| miR.4429 | SEQ 1241 | AAAAGCUGGGCUGAGAGGCG |
| miR.4430 | SEQ 1242 | AGGCUGGAGUGAGCGGAG |
| miR.4433b.5p | SEQ 1243 | AUGUCCACCCCCACUCCUGU |
| miR.4442 | SEQ 1244 | GCCGGACAAGAGGGAGG |
| miR.4449 | SEQ 1245 | CGUCCCGGGGCUGCGCGAGGCA |
| miR.4459 | SEQ 1246 | CCAGGAGGCGGAGGAGGUGGAG |
| miR.4461 | SEQ 1247 | GAUUGAGACUAGUAGGGCUAGGC |
| miR.4463 | SEQ 1248 | GAGACUGGGGUGGGGCC |
| miR.4478 | SEQ 1249 | GAGGCUGAGCUGAGGAG |
| miR.4481 | SEQ 1250 | GGAGUGGGCUGGUGGUU |
| miR.4484 | SEQ 1251 | AAAAGGCGGGAGAAGCCCCA |
| miR.4486 | SEQ 1252 | GCUGGGCGAGGCUGGCA |
| miR.4496 | SEQ 1253 | GAGGAAACUGAAGCUGAGAGGG |
| miR.4505 | SEQ 1254 | AGGCUGGGCUGGGACGGA |
| miR.4507 | SEQ 1255 | CUGGGUUGGGCUGGGCUGGG |
| miR.451a | SEQ 1256 | AAACCGUUACCAUUACUGAGUU |
| miR.4530 | SEQ 1257 | CCCAGCAGGACGGGAGCG |
| miR.4534 | SEQ 1258 | GGAUGGAGGAGGGGUCU |
| miR.4539 | SEQ 1259 | GCUGAACUGGGCUGAGCUGGGC |
| miR.454.3p | SEQ 1260 | UAGUGCAAUAUUGCUUAUAGGGU |
| miR.4632.5p | SEQ 1261 | GAGGGCAGCGUGGGUGUGGCGGA |
| miR.4646.5p | SEQ 1262 | ACUGGGAAGAGGAGCUGAGGGA |
| miR.4655.3p | SEQ 1263 | ACCCUCGUCAGGUCCCCGGG |
| miR.4655.5p | SEQ 1264 | CACCGGGGAUGGCAGAGGGUCG |
| miR.4656 | SEQ 1265 | UGGGCUGAGGGCAGGAGGCCUGU |
| miR.4667.5p | SEQ 1266 | ACUGGGGAGCAGAAGGAGAACC |
| miR.4690.5p | SEQ 1267 | GAGCAGGCGAGGCUGGGCUGAA |
| miR.4695.5p | SEQ 1268 | CAGGAGGCAGUGGGCGAGCAGG |
| miR.4706 | SEQ 1269 | AGCGGGGAGGAAGUGGGCGCUGCUU |

TABLE 1-continued

Sequences of 406 miRNAs

| miRNA | SEQ ID | Sequence |
|---|---|---|
| miR.4707.3p | SEQ 1270 | AGCCCGCCCCAGCCGAGGUUCU |
| miR.4726.5p | SEQ 1271 | AGGGCCAGAGGAGCCUGGAGUGG |
| miR.4728.5p | SEQ 1272 | UGGGAGGGGAGAGGCAGCAAGCA |
| miR.4734 | SEQ 1273 | GCUGCGGGCUGCGGUCAGGGCG |
| miR.4758.5p | SEQ 1274 | GUGAGUGGGAGCCGGUGGGGCUG |
| miR.4763.3 | SEQ 1275 | AGGCAGGGGCUGGUGCUGGGCGGG |
| miR.4784 | SEQ 1276 | UGAGGAGAUGCUGGGACUGA |
| miR.4793.5 | SEQ 1277 | ACAUCCUGCUCCACAGGGCAGAGG |
| miR.4800.3p | SEQ 1278 | CAUCCGUCCGUCUGUCCAC |
| miR.4800.5p | SEQ 1279 | AGUGGACCGAGGAAGGAAGGA |
| miR.484 | SEQ 1280 | UCAGGCUCAGUCCCCUCCCGAU |
| miR.485.3p | SEQ 1281 | GUCAUACACGGCUCUCCUCUCU |
| miR.486.5p | SEQ 1282 | UCCUGUACUGAGCUGCCCCGAG |
| miR.487b.3p | SEQ 1283 | AAUCGUACAGGGUCAUCCACUU |
| miR.491.5p | SEQ 1284 | AGUGGGGAACCCUUCCAUGAGG |
| miR.494.3p | SEQ 1285 | UGAAACAUACACGGGAAACCUC |
| miR.495.3p | SEQ 1286 | AAACAAACAUGGUGCACUUCUU |
| miR.5001.5p | SEQ 1287 | AGGGCUGGACUCAGCGGCGGAGCU |
| miR.5006.5p | SEQ 1288 | UUGCCAGGGCAGGAGGUGGAA |
| miR.502.3p | SEQ 1289 | AAUGCACCUGGGCAAGGAUUCA |
| miR.504.3p | SEQ 1290 | GGGAGUGCAGGGCAGGGUUUC |
| miR.505.3p | SEQ 1291 | CGUCAACACUUGCUGGUUUCCU |
| miR.5196.5p | SEQ 1292 | AGGGAAGGGGACGAGGGUUGGG |
| miR.532.3p | SEQ 1293 | CCUCCCACACCCAAGGCUUGCA |
| miR.532.5p | SEQ 1294 | CAUGCCUUGAGUGUAGGACCGU |
| miR.541.3p | SEQ 1295 | UGGUGGGCACAGAAUCUGGACU |
| miR.543 | SEQ 1296 | AAACAUUCGCGGUGCACUUCUU |
| miR.548ak | SEQ 1297 | AAAAGUAACUGCGGUUUUUGA |
| miR.548d.5p | SEQ 1298 | AAAAGUAAUUGUGGUUUUUGCC |
| miR.551b.3p | SEQ 1299 | GCGACCCAUACUUGGUUUCAG |
| miR.5585.3p | SEQ 1300 | CUGAAUAGCUGGGACUACAGGU |
| miR.5587.3p | SEQ 1301 | GCCCCGGGCAGUGUGAUCAUC |
| miR.561.3p | SEQ 1302 | CAAAGUUUAAGAUCCUUGAAGU |
| miR.566 | SEQ 1303 | GGGCGCCUGUGAUCCCAAC |
| miR.5694 | SEQ 1304 | CAGAUCAUGGGACUGUCUCAG |
| miR.5703 | SEQ 1305 | AGGAGAAGUCGGGAAGGU |
| miR.5739 | SEQ 1306 | GCGGAGAGAGAAUGGGAGC |
| miR.574.3p | SEQ 1307 | CACGCUCAUGCACACACCCACA |
| miR.574.5p | SEQ 1308 | UGAGUGUGUGUGUGUGAGUGU |
| miR.584.5p | SEQ 1309 | UUAUGGUUUGCCUGGGACUGAG |
| miR.590.5p | SEQ 1310 | GAGCUUAUUCAUAAAAGUGCAG |
| miR.6069 | SEQ 1311 | GGGCUAGGGCCUGCUGCCCCC |
| miR.6085 | SEQ 1312 | AAGGGGCUGGGGGAGCACA |
| miR.6086 | SEQ 1313 | GGAGGUUGGGAAGGGCAGAG |
| miR.6088 | SEQ 1314 | AGAGAUGAAGCGGGGGGGCG |
| miR.612 | SEQ 1315 | GCUGGGCAGGGCUUCUGAGCUCCUU |
| miR.6124 | SEQ 1316 | GGGAAAAGGAAGGGGGAGGA |
| miR.6126 | SEQ 1317 | GUGAAGGCCCGGCGGAGA |
| miR.6127 | SEQ 1318 | UGAGGGAGUGGGUGGGAGG |
| miR.6131 | SEQ 1319 | GGCUGGUCAGAUGGGAGUG |
| miR.6165 | SEQ 1320 | CAGCAGGAGGUGAGGGGAG |
| miR.625.5p | SEQ 1321 | AGGGGGAAAGUUCUAUAGUCC |
| miR.629.5p | SEQ 1322 | UGGGUUUACGUUGGGAGAACU |
| miR.6511b.3p | SEQ 1323 | CCUCACCACCCCUUCUGCCUGCA |
| miR.652.3p | SEQ 1324 | AAUGGCGCCACUAGGGUUGUG |
| miR.654.5p | SEQ 1325 | UGGUGGGCCGCAGAACAUGUGC |
| miR.658 | SEQ 1326 | GGCGGAGGGAAGUAGGUCCGUUGGU |
| miR.660.5p | SEQ 1327 | UACCCAUUGCAUAUCGGAGUUG |
| miR.663b | SEQ 1328 | GGUGGCCCGGCCGUGCCUGAGG |
| miR.664a.3p | SEQ 1329 | UAUUCAUUUAUCCCCAGCCUACA |
| miR.664b.5p | SEQ 1330 | UGGGCUAAGGGAGAUGAUUGGGUA |
| miR.671.5p | SEQ 1331 | AGGAAGCCCUGGAGGGGCUGGAG |
| miR.6716.5p | SEQ 1332 | UGGGAAUGGGGGUAAGGGCC |
| miR.6723.5p | SEQ 1333 | AUAGUCCGAGUAACGUCGGGC |
| miR.6726.5p | SEQ 1334 | CGGGAGCUGGGGUCUGCAGGU |
| miR.6727.5p | SEQ 1335 | CUCGGGGCAGGCGGCUGGGAGCG |
| miR.6729.3p | SEQ 1336 | UCAUCCCCCUCGCCCUCUCAG |
| miR.6738.5p | SEQ 1337 | CGAGGGGUAGAAGAGCACAGGGG |
| miR.6741.3p | SEQ 1338 | UCGGCUCUCUCCCUCACCCUAG |
| miR.6741.5p | SEQ 1339 | GUGGGUGCUGGUGGGAGCCGUG |
| miR.6742.5p | SEQ 1340 | AGUGGGUGGGACCCAGCUGUU |
| miR.6746.5p | SEQ 1341 | CCGGGAGAAGGAGGUGGCCUGG |
| miR.6756.5p | SEQ 1342 | AGGGUGGGGCUGGAGGUGGGCU |
| miR.6765.5p | SEQ 1343 | GUGAGGCGGGGCCAGGAGGGUGUGU |
| miR.6769a.5p | SEQ 1344 | AGGUGGGUAUGGAGGAGCCCU |
| miR.6769b.3p | SEQ 1345 | CCCUCUCUGUCCCACCCAUAG |

TABLE 1-continued

Sequences of 406 miRNAs

| miRNA | SEQ ID | Sequence |
|---|---|---|
| miR.6771.3p | SEQ 1346 | CAAACCCCUGUCUACCCGCAG |
| miR.6771.5p | SEQ 1347 | CUCGGGAGGGCAUGGGCCAGGC |
| miR.6775.3p | SEQ 1348 | AGGCCCUGUCCUCUGCCCAG |
| miR.6775.5p | SEQ 1349 | UCGGGGCAUGGGGAGGGAGGCUGG |
| miR.6778.5p | SEQ 1350 | AGUGGGAGGACAGGAGGCAGGU |
| miR.6780b.5p | SEQ 1351 | UGGGGAAGGCUUGGCAGGGAAGA |
| miR.6781.5p | SEQ 1352 | CGGGCCGGAGGUCAAGGGCGU |
| miR.6782.5p | SEQ 1353 | UAGGGGUGGGGGAAUUCAGGGGUGU |
| miR.6785.3p | SEQ 1354 | ACAUCGCCCCACCUUCCCCAG |
| miR.6789.5p | SEQ 1355 | GUAGGGGCGUCCCGGGCGCGCGGG |
| miR.6791.5p | SEQ 1356 | CCCCUGGGGCUGGGCAGGCGGA |
| miR.6794.5p | SEQ 1357 | CAGGGGGACUGGGGGUGAGC |
| miR.6795.3p | SEQ 1358 | ACCCCUCGUUUCUUCCCCCAG |
| miR.6796.3p | SEQ 1359 | GAAGCUCUCCCCUCCCCGCAG |
| miR.6797.5p | SEQ 1360 | AGGAGGGAAGGGGCUGAGAACAGGA |
| miR.6798.5p | SEQ 1361 | CCAGGGGAUGGGCGAGCUUGGG |
| miR.6799.5p | SEQ 1362 | GGGGAGGUGUGCAGGGCUGG |
| miR.6802.5p | SEQ 1363 | CUAGGUGGGGGGCUUGAAGC |
| miR.6803.3p | SEQ 1364 | UCCCUCGCCUUCUCACCCUCAG |
| miR.6803.5p | SEQ 1365 | CUGGGGGUGGGGGGCUGGGCGU |
| miR.6809.5p | SEQ 1366 | UGGCAAGGAAAGAAGAGGAUCA |
| miR.6810.3p | SEQ 1367 | UCCCCUGCUCCCUUGUUCCCCAG |
| miR.6812.5p | SEQ 1368 | AUGGGGUGAGAUGGGGAGGAGCAGC |
| miR.6813.3p | SEQ 1369 | AACCUUGGCCCCUCUCCCCAG |
| miR.6819.3p | SEQ 1370 | AAGCCUCUGUCCCCACCCCAG |
| miR.6821.5p | SEQ 1371 | GUGCGUGGUGGCUCGAGGCGGGG |
| miR.6824.5p | SEQ 1372 | GUAGGGGAGGUUGGGCAGGGA |
| miR.6829.5p | SEQ 1373 | UGGGCUGCUGAGAAGGGGCA |
| miR.6845.5p | SEQ 1374 | CGGGGCCAGAGCAGAGAGC |
| miR.6852.3p | SEQ 1375 | UGUCCUCUGUUCCUCAG |
| miR.6852.5p | SEQ 1376 | CCCUGGGGUUCUGAGGACAUG |
| miR.6869.5p | SEQ 1377 | GUGAGUAGUGGCGCGCGGCGGC |
| miR.6870.3p | SEQ 1378 | GCUCAUCCCCAUCUCCUUUCAG |
| miR.6870.5p | SEQ 1379 | UGGGGGAGAUGGGGGUUGA |
| miR.6873.3p | SEQ 1380 | UUCUCUCUGUCUUUCUCUCAG |
| miR.6875.5p | SEQ 1381 | UGAGGGACCCAGGACAGGAGA |
| miR.6877.5p | SEQ 1382 | AGGGCCGAAGGGUGGAAGCUGC |
| miR.6880.5p | SEQ 1383 | UGGUGGAGGAAGAGGGCAGCUC |
| miR.6892.3p | SEQ 1384 | UCCCUCUCCCACCCCUUGCAG |
| miR.6894.5p | SEQ 1385 | AGGAGGAUGGAGAGCUGGGCCAGA |
| miR.7106.5p | SEQ 1386 | UGGGAGGAGGGGAUCUUGGG |
| miR.7107.5p | SEQ 1387 | UCGGCCUGGGGAGGAGGAAGGG |
| miR.7108.5p | SEQ 1388 | GUGUGGCCGGCAGGCGGGUGG |
| miR.7111.5p | SEQ 1389 | UGGGGGAGGAAGGACAGGCCAU |
| miR.7114.3p | SEQ 1390 | UGACCCACCCCUCUCCACCAG |
| miR.7150 | SEQ 1391 | CUGGCAGGGGAGAGGUA |
| miR.744.5p | SEQ 1392 | UGCGGGGCUAGGGCUAACAGCA |
| miR.764 | SEQ 1393 | GCAGGUGCUCACUUGUCCUCCU |
| miR.765 | SEQ 1394 | UGGAGGAGAAGGAAGGUGAUG |
| miR.766.3p | SEQ 1395 | ACUCCAGCCCCACAGCCUCAGC |
| miR.766.5p | SEQ 1396 | AGGAGGAAUUGGUGCUGGUCUU |
| miR.769.5p | SEQ 1397 | UGAGACCUCUGGGUUCUGAGCU |
| miR.7845.5p | SEQ 1398 | AAGGGACAGGGAGGGUCGUGG |
| miR.7851.3p | SEQ 1399 | UACCUGGGAGACUGAGGUUGGA |
| miR.8069 | SEQ 1400 | GGAUGGUUGGGGCGGUCGGCGU |
| miR.8071 | SEQ 1401 | CGGUGGACUGGAGUGGGUGG |
| miR.8078 | SEQ 1402 | GGUCUAGGCCCGGUGAGAGACUC |
| miR.8085 | SEQ 1403 | UGGGAGAGAGGACUGUGAGGC |
| miR.8089 | SEQ 1404 | CCUGGGGACAGGGGAUUGGGCAG |
| miR.874.3p | SEQ 1405 | CUGCCCUGGCCCGAGGGACCGA |
| miR.877.3p | SEQ 1406 | UCCUCUUCUCCCUCCUCCCAG |
| miR.877.5p | SEQ 1407 | GUAGAGGAGAUGGCGCAGGG |
| miR.920 | SEQ 1408 | GGGGAGCUGUGGAAGCAGUA |
| miR.92a.3p | SEQ 1409 | UAUUGCACUUGUCCCGGCCUGU |
| miR.92b.3p | SEQ 1410 | UAUUGCACUCGUCCCGGCCUCC |
| miR.93.3p | SEQ 1411 | ACUGCUGAGCUAGCACUUCCCG |
| miR.93.5p | SEQ 1412 | CAAAGUGCUGUUCGUGCAGGUAG |
| miR.99a.5p | SEQ 1413 | AACCCGUAGAUCCGAUCUUGUG |
| miR.99b.5p | SEQ 1414 | CACCCGUAGAACCGACCUUGCG |

Out of the 406 detectable miRNAs analyzed, 28 miRNAs showed a statistically significant difference (Welch T-test p value <0.05), and among these candidates, 7 candidates showed a p value <0.01. The 28 miRNAs are shown in Table 2.

TABLE 2

List of 28 miRNAs useful based on their p value < 0.05. SD: standard deviation

| miRNA candidate | p value | Mean Log2 AD | SD log2 AD | Mean Log2 HC | SD log2 HC | Fold change | AUC |
|---|---|---|---|---|---|---|---|
| miR.99a.5p | 0.00025 | 8.92 | 0.53 | 8.52 | 0.42 | 1.348 | 0.268 |
| miR.378d | 0.00114 | 6.49 | 0.44 | 6.13 | 0.55 | 1.252 | 0.303 |
| miR.100.5p | 0.00147 | 7.51 | 0.54 | 7.18 | 0.38 | 1.304 | 0.301 |
| miR.193b.3p | 0.00242 | 6.75 | 1.01 | 6.14 | 0.80 | 1.716 | 0.307 |
| miR.34a.5p | 0.00602 | 6.84 | 0.89 | 6.32 | 0.81 | 1.479 | 0.342 |
| miR.1306.5p | 0.00865 | 7.13 | 0.44 | 6.90 | 0.39 | 1.190 | 0.328 |
| miR.1229.3p | 0.00909 | 6.08 | 0.59 | 5.60 | 1.05 | 1.306 | 0.301 |
| miR.195.5p | 0.01062 | 6.40 | 0.78 | 5.98 | 0.74 | 1.360 | 0.333 |
| miR.6880.5p | 0.01316 | 7.83 | 0.81 | 8.27 | 0.82 | 0.717 | 0.655 |
| miR.192.5p | 0.01449 | 7.96 | 1.04 | 7.48 | 0.70 | 1.666 | 0.378 |
| miR.532.5p | 0.01485 | 7.27 | 0.53 | 7.01 | 0.43 | 1.225 | 0.354 |
| miR.125b.5p | 0.01546 | 8.52 | 0.52 | 8.26 | 0.46 | 1.212 | 0.341 |
| miR.375 | 0.01644 | 7.19 | 1.03 | 6.66 | 0.99 | 1.468 | 0.363 |
| miR.378a.3p | 0.01800 | 7.93 | 0.46 | 7.70 | 0.43 | 1.184 | 0.381 |
| miR.532.3p | 0.01880 | 7.02 | 0.71 | 6.67 | 0.63 | 1.300 | 0.334 |
| miR.378i | 0.01888 | 7.64 | 0.43 | 7.43 | 0.40 | 1.165 | 0.351 |
| miR.194.5p | 0.01913 | 7.32 | 1.24 | 6.77 | 0.89 | 1.823 | 0.369 |
| miR.122.5p | 0.02053 | 10.72 | 1.49 | 10.04 | 1.17 | 2.225 | 0.380 |
| miR.141.3p | 0.02126 | 6.30 | 0.51 | 6.05 | 0.51 | 1.195 | 0.370 |
| miR.660.5p | 0.02134 | 7.54 | 0.92 | 7.10 | 0.84 | 1.415 | 0.363 |
| miR.5196.5p | 0.03121 | 9.19 | 0.84 | 9.59 | 0.86 | 0.741 | 0.649 |
| miR.6769a.5p | 0.03130 | 6.66 | 0.82 | 7.04 | 0.79 | 0.764 | 0.647 |
| miR.378f | 0.03183 | 7.02 | 0.46 | 6.80 | 0.50 | 1.160 | 0.375 |
| miR.144.3p | 0.03740 | 6.78 | 2.07 | 5.74 | 2.49 | 1.606 | 0.372 |
| miR.7111.5p | 0.03968 | 9.63 | 0.78 | 10.02 | 0.92 | 0.733 | 0.622 |
| miR.4270 | 0.04181 | 6.93 | 0.77 | 7.25 | 0.64 | 0.831 | 0.636 |
| miR.664a.3p | 0.04186 | 6.24 | 1.10 | 5.59 | 1.76 | 1.280 | 0.396 |
| miR.502.3p | 0.04801 | 6.14 | 0.75 | 5.83 | 0.70 | 1.262 | 0.378 |

Among the 406 detected miRNA, a total of 74 miRNA candidates also showed an AUC value ≥0.6 or ≤0.4; of which a total of 11 candidates showed a good AUC value of ≥0.65 or ≤0.35; and 1 candidates showed a very good AUC value of ≥0.7 or ≤0.30. The 74 candidate miRNAs are shown in Table 3.

TABLE 3

List of 74 candidates also showed an AUC value of ≥0.6 or ≤0.40

| miRNA | AUC |
|---|---|
| miR.99a.5p | 0.268 |
| miR.1229.3p | 0.301 |
| miR.100.5p | 0.301 |
| miR.378d | 0.303 |
| miR.193b.3p | 0.307 |
| miR.1306.5p | 0.328 |
| miR.195.5p | 0.333 |
| miR.532.3p | 0.334 |
| miR.125b.5p | 0.341 |
| miR.34a.5p | 0.342 |
| miR.378i | 0.351 |
| miR.532.5p | 0.354 |
| miR.375 | 0.363 |
| miR.660.5p | 0.363 |
| miR.194.5p | 0.369 |
| miR.141.3p | 0.370 |
| miR.144.3p | 0.372 |
| miR.1234.3p | 0.373 |
| miR.378f | 0.375 |
| miR.181b.5p | 0.376 |
| miR.502.3p | 0.378 |
| miR.192.5p | 0.378 |
| miR.766.3p | 0.378 |
| miR.122.5p | 0.380 |
| miR.378a.3p | 0.381 |
| miR.145.5p | 0.383 |
| miR.139.5p | 0.384 |
| miR.150.5p | 0.386 |
| miR.193a.3p | 0.390 |
| miR.342.3p | 0.391 |
| miR.210.3p | 0.392 |
| miR.144.5p | 0.392 |
| miR.27b.3p | 0.394 |
| miR.664a.3p | 0.396 |
| miR.16.5p | 0.396 |
| miR.877.3p | 0.397 |
| miR.29a.3p | 0.400 |
| miR.130a.3p | 0.400 |
| miR.6794.5p | 0.601 |
| miR.1908.5p | 0.601 |
| miR.6799.5p | 0.602 |
| miR.3141 | 0.604 |
| miR.6738.5p | 0.604 |
| miR.6894.5p | 0.604 |
| miR.7851.3p | 0.605 |
| miR.4695.5p | 0.608 |
| miR.23a.5p | 0.609 |
| miR.4463 | 0.610 |
| miR.382.5p | 0.611 |
| miR.4655.5p | 0.611 |
| miR.4800.5p | 0.612 |
| miR.6746.5p | 0.613 |
| miR.4667.5p | 0.614 |
| miR.4656 | 0.614 |
| miR.1914.3p | 0.616 |
| miR.1275 | 0.618 |
| miR.8089 | 0.619 |
| miR.5703 | 0.619 |
| miR.6124 | 0.621 |
| miR.2392 | 0.621 |
| miR.7111.5p | 0.622 |
| miR.8085 | 0.622 |
| miR.6716.5p | 0.624 |
| miR.6778.5p | 0.625 |
| miR.6797.5p | 0.625 |
| miR.4534 | 0.633 |
| miR.6775.5p | 0.635 |
| miR.4270 | 0.636 |
| miR.6812.5p | 0.638 |
| miR.6086 | 0.645 |
| miR.765 | 0.645 |
| miR.6769a.5p | 0.647 |
| miR.5196.5p | 0.649 |
| miR.6880.5p | 0.655 |

Among the 406 detected miRNAs, a total of 15 candidates showed both an AUC value of ≥0.6 or ≤0.4 and a fold change value of ≥1.49 or ≤0.75. The list of the 15 miRNAs are shown in Table 4.

TABLE 4

List of 15 candidates showing both an AUC value of ≥0.6 or ≤0.4 and a fold change value of ≥1.49 or ≤0.75

| miRNA | p value | Fold change | AUC |
|---|---|---|---|
| miR.23a.5p | 0.06528 | 0.630 | 0.609 |
| miR.6880.5p | 0.01316 | 0.717 | 0.655 |
| miR.7111.5p | 0.03968 | 0.733 | 0.622 |
| miR.6812.5p | 0.05632 | 0.735 | 0.638 |
| miR.6738.5p | 0.07930 | 0.741 | 0.604 |
| miR.5196.5p | 0.03121 | 0.741 | 0.649 |
| miR.6894.5p | 0.10422 | 0.746 | 0.604 |
| miR.8085 | 0.27457 | 0.747 | 0.622 |
| miR.4463 | 0.08930 | 0.748 | 0.610 |
| miR.2392 | 0.10513 | 0.748 | 0.621 |
| miR.144.3p | 0.03740 | 1.606 | 0.372 |
| miR.192.5p | 0.01449 | 1.666 | 0.378 |
| miR.193b.3p | 0.00242 | 1.716 | 0.307 |

TABLE 4-continued

List of 15 candidates showing both an AUC value of ≥0.6 or ≤0.4 and a fold change value of ≥1.49 or ≤0.75

| miRNA | p value | Fold change | AUC |
|---|---|---|---|
| miR.194.5p | 0.01913 | 1.823 | 0.369 |
| miR.122.5p | 0.02053 | 2.225 | 0.380 |

Out of the 127802 lncRNAs sequenced, 19867 lncRNAs were selected based on their threshold expression level for statistical analysis. The comparison of the AD patient with healthy control populations showed that 1008 lncRNAs are differentially expressed with a statistical significance (p value <0.05, Wilcoxon test) (Table 5). The sequences of these 1008 lncRNAs are shown in the sequence listing included in this application.

TABLE 5

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| ADAMTS9-AS2:12 | SEQ0397 | 0.02049 | 0.852 | 0.778 |
| ADNP-AS1:12 | SEQ0340 | 0.01727 | 0.809 | 0.785 |
| ADPGK-AS1:7 | SEQ0858 | 0.0449 | 1.225 | 0.257 |
| APTR:17 | SEQ0260 | 0.01209 | 1.147 | 0.201 |
| ARF4-AS1:8 | SEQ0859 | 0.0449 | 1.143 | 0.257 |
| ARRDC3-AS1:7 | SEQ0050 | 0.00232 | 0.441 | 0.854 |
| BISPR:24 | SEQ0566 | 0.02842 | 0.579 | 0.764 |
| BLACAT1:3 | SEQ0300 | 0.01449 | 1.717 | 0.208 |
| BLACAT1:5 | SEQ0341 | 0.01727 | 0.424 | 0.785 |
| CALML3-AS1:9 | SEQ0136 | 0.00681 | 1.567 | 0.181 |
| CASC15:51 | SEQ0567 | 0.02842 | 1.273 | 0.236 |
| CASC20:2 | SEQ0860 | 0.0449 | 0.765 | 0.743 |
| CERS3-AS1:5 | SEQ0301 | 0.01449 | 1.251 | 0.208 |
| CFAP58-AS1:4 | SEQ0109 | 0.00556 | 1.464 | 0.174 |
| CLRN1-AS1:1 | SEQ0475 | 0.02418 | 0.793 | 0.771 |
| CPB2-AS1:18 | SEQ0476 | 0.02418 | 0.682 | 0.771 |
| CYTOR:18 | SEQ0062 | 0.00291 | 1.278 | 0.153 |
| DARS-AS1:47 | SEQ0178 | 0.00829 | 2.015 | 0.188 |
| DDX11-AS1:5 | SEQ0861 | 0.0449 | 1.256 | 0.257 |
| DLEU2:26 | SEQ0862 | 0.0449 | 1.076 | 0.257 |
| DLEU2:45 | SEQ0863 | 0.0449 | 0.882 | 0.743 |
| DLGAP2-AS1:18 | SEQ0656 | 0.03324 | 0.789 | 0.757 |
| DPH6-AS1:3 | SEQ0342 | 0.01727 | 2.004 | 0.215 |
| EGFR-AS1:4 | SEQ0093 | 0.00451 | 0.81 | 0.833 |
| EGOT:11 | SEQ0110 | 0.00556 | 1.195 | 0.174 |
| EIF3J-AS1:21 | SEQ0261 | 0.01209 | 0.87 | 0.799 |
| ERICH3-AS1:4 | SEQ0864 | 0.0449 | 0.888 | 0.743 |
| EXTL3-AS1:16 | SEQ0568 | 0.02842 | 0.739 | 0.764 |
| FAM66B:14 | SEQ0063 | 0.00291 | 0.604 | 0.847 |
| FLG-AS1:14 | SEQ0752 | 0.03872 | 1.18 | 0.25 |
| FLVCR1-AS1:13 | SEQ0137 | 0.00681 | 0.413 | 0.819 |
| FRG1-DT:6 | SEQ0865 | 0.0449 | 0.873 | 0.743 |
| GAS1RR:11 | SEQ0302 | 0.01449 | 0.848 | 0.792 |
| GAS6-AS2:9 | SEQ0303 | 0.01449 | 0.787 | 0.792 |
| GPC5-AS1:7 | SEQ0753 | 0.03872 | 0.623 | 0.75 |
| GPR158-AS1:1 | SEQ0398 | 0.02049 | 0.775 | 0.778 |
| GRM5-AS1:1 | SEQ0138 | 0.00681 | 0.83 | 0.819 |
| HAND2-AS1:58 | SEQ0094 | 0.00451 | 0.587 | 0.833 |
| HAND2-AS1:59 | SEQ0111 | 0.00556 | 0.592 | 0.826 |
| HAND2-AS1:70 | SEQ0039 | 0.00183 | 0.543 | 0.861 |
| HAND2-AS1:71 | SEQ0076 | 0.00364 | 0.565 | 0.84 |
| HCG23:5 | SEQ0754 | 0.03872 | 0.813 | 0.75 |
| KAZN-AS1:4 | SEQ0399 | 0.02049 | 0.732 | 0.778 |
| KCNQ1-AS1:3 | SEQ0569 | 0.02842 | 0.848 | 0.764 |
| KCNQ1OT1:8 | SEQ0139 | 0.00681 | 0.908 | 0.819 |
| LACTB2-AS1:1 | SEQ0755 | 0.03872 | 1.206 | 0.25 |
| LINC00158:5 | SEQ0570 | 0.02842 | 0.748 | 0.764 |
| LINC00200:6 | SEQ0064 | 0.00291 | 1.29 | 0.153 |
| LINC00276:2 | SEQ0866 | 0.0449 | 0.846 | 0.743 |
| LINC00354:4 | SEQ0867 | 0.0449 | 1.284 | 0.257 |
| LINC00458:19 | SEQ0571 | 0.02842 | 0.789 | 0.764 |
| LINC00460:13 | SEQ0868 | 0.0449 | 0.752 | 0.743 |
| LINC00472:21 | SEQ0140 | 0.00681 | 1.389 | 0.181 |
| LINC00554:2 | SEQ0756 | 0.03872 | 0.766 | 0.75 |
| LINC00554:4 | SEQ0757 | 0.03872 | 0.766 | 0.75 |
| LINC00574:13 | SEQ0112 | 0.00556 | 0.771 | 0.826 |
| LINC00589:3 | SEQ0869 | 0.0449 | 0.781 | 0.743 |
| LINC00649:23 | SEQ0077 | 0.00364 | 0.619 | 0.84 |
| LINC00698:2 | SEQ0657 | 0.03324 | 0.85 | 0.757 |
| LINC00707:9 | SEQ0572 | 0.02842 | 1.304 | 0.236 |
| LINC00839:18 | SEQ0113 | 0.00556 | 0.874 | 0.826 |
| LINC00882:70 | SEQ0028 | 0.00111 | 0.867 | 0.875 |
| LINC00882:71 | SEQ0029 | 0.00111 | 0.867 | 0.875 |
| LINC00887:15 | SEQ0870 | 0.0449 | 0.925 | 0.743 |
| LINC00895:3 | SEQ0179 | 0.00829 | 1.491 | 0.188 |
| LINC00927:21 | SEQ0658 | 0.03324 | 0.619 | 0.757 |
| LINC00927:22 | SEQ0659 | 0.03324 | 0.619 | 0.757 |
| LINC00927:24 | SEQ0343 | 0.01727 | 0.772 | 0.785 |
| LINC00938:6 | SEQ0262 | 0.01209 | 0.811 | 0.799 |
| LINC00963:67 | SEQ0573 | 0.02842 | 1.379 | 0.236 |
| LINC01050:6 | SEQ0114 | 0.00556 | 0.82 | 0.826 |
| LINC01058:3 | SEQ0871 | 0.0449 | 1.225 | 0.257 |
| LINC01087:1 | SEQ0141 | 0.00681 | 0.764 | 0.819 |
| LINC01088:18 | SEQ0660 | 0.03324 | 0.757 | 0.757 |
| LINC01107:1 | SEQ0304 | 0.01449 | 0.768 | 0.792 |
| LINC01122:27 | SEQ0574 | 0.02842 | 1.263 | 0.236 |
| LINC01146:14 | SEQ0758 | 0.03872 | 0.774 | 0.75 |
| LINC01153:1 | SEQ0661 | 0.03324 | 1.169 | 0.243 |
| LINC01185:7 | SEQ0575 | 0.02842 | 0.793 | 0.764 |
| LINC02252:3 | SEQ0765 | 0.03872 | 0.881 | 0.75 |
| LINC02323:8 | SEQ0307 | 0.01449 | 0.622 | 0.792 |
| LINC02334:6 | SEQ0581 | 0.02842 | 0.737 | 0.764 |
| LINC02345:11 | SEQ0013 | 0.00066 | 1.181 | 0.111 |
| LINC02432:9 | SEQ0180 | 0.00829 | 0.776 | 0.813 |
| LINC02473:3 | SEQ0065 | 0.00291 | 0.786 | 0.847 |
| LINC02519:7 | SEQ0875 | 0.0449 | 0.682 | 0.743 |
| LINC02554:5 | SEQ0404 | 0.02049 | 0.744 | 0.778 |
| LINC02580:5 | SEQ0484 | 0.02418 | 0.767 | 0.771 |
| lnc-AASDHPPT-3:1 | SEQ0409 | 0.02049 | 0.715 | 0.778 |
| lnc-ABCA1-8:9 | SEQ0589 | 0.02842 | 0.592 | 0.764 |
| lnc-ABCA5-14:2 | SEQ0881 | 0.0449 | 1.164 | 0.257 |
| lnc-ABCA5-7:1 | SEQ0014 | 0.00066 | 1.309 | 0.111 |
| lnc-ABCG2-3:5 | SEQ0667 | 0.03324 | 0.758 | 0.757 |
| lnc-ACO1-1:1 | SEQ0590 | 0.02842 | 0.759 | 0.764 |
| lnc-ACOT12-9:1 | SEQ0053 | 0.00232 | 0.727 | 0.854 |
| lnc-ACTL7B-8:1 | SEQ0493 | 0.02418 | 0.697 | 0.771 |
| lnc-ADAD1-3:1 | SEQ0774 | 0.03872 | 0.828 | 0.75 |
| lnc-ADAMTS20-3:1 | SEQ0494 | 0.02418 | 1.219 | 0.229 |
| lnc-ADAMTS5-1:1 | SEQ0882 | 0.0449 | 0.851 | 0.743 |
| lnc-ADAT1-1:1 | SEQ0495 | 0.02418 | 0.877 | 0.771 |
| lnc-ADRA2A-4:1 | SEQ0883 | 0.0449 | 0.729 | 0.743 |
| lnc-ADRB1-4:1 | SEQ0118 | 0.00556 | 0.858 | 0.826 |
| lnc-AFG1L-5:1 | SEQ0263 | 0.01209 | 1.407 | 0.201 |
| lnc-AGO2-2:2 | SEQ0119 | 0.00556 | 0.511 | 0.826 |
| lnc-AGO2-2:3 | SEQ0668 | 0.03324 | 1.442 | 0.243 |
| lnc-AGR3-6:1 | SEQ0884 | 0.0449 | 1.156 | 0.257 |
| lnc-AHR-5:1 | SEQ0264 | 0.01209 | 0.792 | 0.799 |
| lnc-AIG1-5:1 | SEQ0496 | 0.02418 | 0.862 | 0.771 |
| lnc-AKAP9-1:2 | SEQ0775 | 0.03872 | 0.704 | 0.75 |
| lnc-AKIRIN1-1:11 | SEQ0591 | 0.02842 | 0.553 | 0.764 |
| lnc-AKR1C2-3:17 | SEQ0097 | 0.00451 | 0.768 | 0.833 |
| lnc-AKR1D1-5:2 | SEQ0098 | 0.00451 | 0.891 | 0.833 |
| lnc-AKR1D1-8:3 | SEQ0885 | 0.0449 | 0.797 | 0.743 |
| lnc-AKR1E2-15:1 | SEQ0410 | 0.02049 | 1.303 | 0.222 |
| lnc-AKR7A2-2:1 | SEQ0145 | 0.00681 | 1.339 | 0.181 |
| lnc-AKT1-1:15 | SEQ0411 | 0.02049 | 0.825 | 0.778 |
| lnc-ALB-1:12 | SEQ0146 | 0.00681 | 1.448 | 0.181 |
| lnc-ALB-1:6 | SEQ0886 | 0.0449 | 0.881 | 0.743 |
| lnc-ALDH3B2-3:4 | SEQ0412 | 0.02049 | 0.89 | 0.778 |
| lnc-ALG14-5:2 | SEQ0350 | 0.01727 | 0.697 | 0.785 |
| lnc-ALS2CR12-1:2 | SEQ0351 | 0.01727 | 0.729 | 0.785 |
| lnc-ANAPC11-2:6 | SEQ0887 | 0.0449 | 1.836 | 0.257 |
| lnc-ANKRD1-1:6 | SEQ0888 | 0.0449 | 0.77 | 0.743 |
| lnc-ANKRD26-1:3 | SEQ0497 | 0.02418 | 0.852 | 0.771 |
| lnc-ANKRD30BL-2:2 | SEQ0413 | 0.02049 | 0.747 | 0.778 |
| lnc-ANKRD46-1:3 | SEQ0669 | 0.03324 | 0.687 | 0.757 |

TABLE 5-continued

The Sequence number, p value, mean +/− SD, fold change
and AUC of the 1008 lncRNAs with differential expression in
AD group versus healthy control group (p value < 0.05, Wilcoxon test)

| lncRNA | SEQ | p value | Fold change | AUC |
|---|---|---|---|---|
| lnc-ANXA3-8:1 | SEQ0670 | 0.03324 | 0.838 | 0.757 |
| lnc-APBA1-5:1 | SEQ0592 | 0.02842 | 0.781 | 0.764 |
| lnc-APIP-1:13 | SEQ0776 | 0.03872 | 0.807 | 0.75 |
| lnc-APLP2-4:1 | SEQ0054 | 0.00232 | 0.786 | 0.854 |
| lnc-APOB-1:2 | SEQ0777 | 0.03872 | 0.583 | 0.75 |
| lnc-APPL2-1:2 | SEQ0498 | 0.02418 | 1.133 | 0.229 |
| lnc-AQP8-2:7 | SEQ0352 | 0.01727 | 1.254 | 0.215 |
| lnc-ARAP2-9:1 | SEQ0147 | 0.00681 | 0.795 | 0.819 |
| lnc-ARHGAP15-17:1 | SEQ0353 | 0.01727 | 0.857 | 0.785 |
| lnc-ARHGAP15-22:1 | SEQ0593 | 0.02842 | 0.846 | 0.764 |
| lnc-ARHGAP21-1:2 | SEQ0309 | 0.01449 | 0.723 | 0.792 |
| lnc-ARHGAP26-4:11 | SEQ0189 | 0.00829 | 0.923 | 0.813 |
| lnc-ARHGAP26-4:33 | SEQ0778 | 0.03872 | 0.71 | 0.75 |
| lnc-ARHGAP26-4:39 | SEQ0889 | 0.0449 | 1.383 | 0.257 |
| lnc-ARHGEF26-2:1 | SEQ0067 | 0.00291 | 1.399 | 0.153 |
| lnc-ARHGEF5-5:1 | SEQ0354 | 0.01727 | 0.712 | 0.785 |
| lnc-ARID2-7:1 | SEQ0671 | 0.03324 | 0.924 | 0.757 |
| lnc-ARNTL-2:1 | SEQ0265 | 0.01209 | 0.61 | 0.799 |
| lnc-ARRDC4-7:1 | SEQ0779 | 0.03872 | 0.876 | 0.75 |
| lnc-ART5-2:1 | SEQ0414 | 0.02049 | 0.787 | 0.778 |
| lnc-ATAD1-5:2 | SEQ0148 | 0.00681 | 0.738 | 0.819 |
| lnc-ATIC-2:8 | SEQ0780 | 0.03872 | 0.554 | 0.75 |
| lnc-ATP12A-3:1 | SEQ0499 | 0.02418 | 0.763 | 0.771 |
| lnc-ATP13A4-2:4 | SEQ0672 | 0.03324 | 1.64 | 0.243 |
| lnc-ATP5O-3:1 | SEQ0224 | 0.01004 | 1.358 | 0.194 |
| lnc-ATP6V0E2-7:1 | SEQ0500 | 0.02418 | 1.361 | 0.229 |
| lnc-ATP6V1B2-2:6 | SEQ0594 | 0.02842 | 1.132 | 0.236 |
| lnc-ATP6V1B2-2:7 | SEQ0595 | 0.02842 | 1.132 | 0.236 |
| lnc-ATP8A2-1:1 | SEQ0355 | 0.01727 | 1.477 | 0.215 |
| lnc-ATXN2-1:1 | SEQ0099 | 0.00451 | 0.792 | 0.833 |
| lnc-ATXN7-11:1 | SEQ0501 | 0.02418 | 1.319 | 0.229 |
| lnc-ATXN7L1-1:1 | SEQ0890 | 0.0449 | 1.32 | 0.257 |
| lnc-AUH-2:7 | SEQ0190 | 0.00829 | 0.584 | 0.813 |
| lnc-AUH-2:9 | SEQ0673 | 0.03324 | 1.35 | 0.243 |
| lnc-AUH-4:1 | SEQ0596 | 0.02842 | 0.79 | 0.764 |
| lnc-BAG3-4:4 | SEQ0891 | 0.0449 | 1.314 | 0.257 |
| lnc-BARHL2-4:4 | SEQ0100 | 0.00451 | 0.736 | 0.833 |
| lnc-BCHE-1:1 | SEQ0674 | 0.03324 | 0.741 | 0.757 |
| lnc-BCL6-9:1 | SEQ0310 | 0.01449 | 0.885 | 0.792 |
| lnc-BIRC2-5:5 | SEQ0225 | 0.01004 | 0.831 | 0.806 |
| lnc-BIRC6-1:4 | SEQ0892 | 0.0449 | 0.829 | 0.743 |
| lnc-BMS1-2:1 | SEQ0675 | 0.03324 | 1.124 | 0.243 |
| lnc-BNC2-5:1 | SEQ0191 | 0.00829 | 1.299 | 0.188 |
| lnc-BORA-3:1 | SEQ0192 | 0.00829 | 0.67 | 0.813 |
| lnc-BRD1-17:1 | SEQ0311 | 0.01449 | 0.669 | 0.792 |
| lnc-BRINP1-3:1 | SEQ0893 | 0.0449 | 0.894 | 0.743 |
| lnc-BRINP2-3:1 | SEQ0597 | 0.02842 | 0.878 | 0.764 |
| lnc-C10orf90-2:2 | SEQ0415 | 0.02049 | 1.687 | 0.222 |
| lnc-C12orf40-3:3 | SEQ0894 | 0.0449 | 1.434 | 0.257 |
| lnc-C12orf42-3:6 | SEQ0598 | 0.02842 | 1.303 | 0.236 |
| lnc-C15orf41-18:5 | SEQ0676 | 0.03324 | 1.649 | 0.243 |
| lnc-C15orf41-18:6 | SEQ0895 | 0.0449 | 1.561 | 0.257 |
| lnc-C19orf57-1:1 | SEQ0896 | 0.0449 | 1.361 | 0.257 |
| lnc-C1QTNF9-4:1 | SEQ0781 | 0.03872 | 1.282 | 0.25 |
| lnc-C21orf58-1:2 | SEQ0033 | 0.00143 | 2.231 | 0.132 |
| lnc-C2CD4B-6:4 | SEQ0193 | 0.00829 | 1.39 | 0.188 |
| lnc-C2orf42-10:1 | SEQ0502 | 0.02418 | 1.28 | 0.229 |
| lnc-C3orf58-7:1 | SEQ0599 | 0.02842 | 0.725 | 0.764 |
| lnc-C5orf30-10:1 | SEQ0266 | 0.01209 | 0.708 | 0.799 |
| lnc-C5orf30-10:2 | SEQ0600 | 0.02842 | 0.891 | 0.764 |
| lnc-C5orf67-3:1 | SEQ0149 | 0.00681 | 0.876 | 0.819 |
| lnc-C7orf57-4:1 | SEQ0356 | 0.01727 | 1.461 | 0.215 |
| lnc-C9orf3-5:1 | SEQ0120 | 0.00556 | 0.782 | 0.826 |
| lnc-CA7-2:2 | SEQ0677 | 0.03324 | 0.817 | 0.757 |
| lnc-CAB39L-1:4 | SEQ0267 | 0.01209 | 0.769 | 0.799 |
| lnc-CAB39L-4:2 | SEQ0601 | 0.02842 | 1.181 | 0.236 |
| lnc-CACNA1I-1:1 | SEQ0503 | 0.02418 | 0.813 | 0.771 |
| lnc-CACNA2D1-1:1 | SEQ0897 | 0.0449 | 0.82 | 0.743 |
| lnc-CACNG1-1:1 | SEQ0602 | 0.02842 | 0.652 | 0.764 |
| lnc-CALML6-1:10 | SEQ0898 | 0.0449 | 0.577 | 0.743 |
| lnc-CAPS2-1:1 | SEQ0357 | 0.01727 | 0.708 | 0.785 |
| lnc-CASC10-3:1 | SEQ0899 | 0.0449 | 0.744 | 0.743 |
| lnc-CASP9-1:1 | SEQ0782 | 0.03872 | 1.246 | 0.25 |
| lnc-CAVIN2-2:1 | SEQ0416 | 0.02049 | 1.425 | 0.222 |
| lnc-CBLB-9:1 | SEQ0900 | 0.0449 | 0.788 | 0.743 |
| lnc-CCDC102B-7:1 | SEQ0901 | 0.0449 | 0.816 | 0.743 |
| lnc-CCDC167-5:1 | SEQ0417 | 0.02049 | 1.25 | 0.222 |
| lnc-CCDC177-6:1 | SEQ0783 | 0.03872 | 1.157 | 0.25 |
| lnc-CCDC192-3:1 | SEQ0902 | 0.0449 | 0.8 | 0.743 |
| lnc-CCDC197-2:1 | SEQ0068 | 0.00291 | 0.672 | 0.847 |
| lnc-CCDC61-4:1 | SEQ0194 | 0.00829 | 0.561 | 0.813 |
| lnc-CCDC7-17:1 | SEQ0226 | 0.01004 | 1.341 | 0.194 |
| lnc-CCDC93-10:2 | SEQ0603 | 0.02842 | 0.87 | 0.764 |
| lnc-CCL1-10:1 | SEQ0227 | 0.01004 | 1.307 | 0.194 |
| lnc-CCNB1IP1-1:2 | SEQ0903 | 0.0449 | 0.512 | 0.743 |
| lnc-CCR8-2:1 | SEQ0904 | 0.0449 | 1.409 | 0.257 |
| lnc-CCSER1-2:1 | SEQ0678 | 0.03324 | 0.791 | 0.757 |
| lnc-CCT8L2-28:1 | SEQ0418 | 0.02049 | 0.812 | 0.778 |
| lnc-CD47-11:2 | SEQ0905 | 0.0449 | 1.317 | 0.257 |
| lnc-CD47-11:4 | SEQ0906 | 0.0449 | 1.139 | 0.257 |
| lnc-CDADC1-1:1 | SEQ0907 | 0.0449 | 1.18 | 0.257 |
| lnc-CDH23-2:1 | SEQ0908 | 0.0449 | 0.757 | 0.743 |
| lnc-CDK20-14:1 | SEQ0358 | 0.01727 | 1.274 | 0.215 |
| lnc-CDK2AP1-1:8 | SEQ0909 | 0.0449 | 0.84 | 0.743 |
| lnc-CEACAM16-2:1 | SEQ0195 | 0.00829 | 0.708 | 0.813 |
| lnc-CEBPD-11:2 | SEQ0784 | 0.03872 | 0.763 | 0.75 |
| lnc-CELF4-15:1 | SEQ0785 | 0.03872 | 0.89 | 0.75 |
| lnc-CELSR1-2:3 | SEQ0268 | 0.01209 | 0.762 | 0.799 |
| lnc-CEP170-9:2 | SEQ0042 | 0.00183 | 0.828 | 0.861 |
| lnc-CFAP36-3:2 | SEQ0786 | 0.03872 | 0.69 | 0.75 |
| lnc-CHD1L-5:13 | SEQ0312 | 0.01449 | 0.37 | 0.792 |
| lnc-CHMP2B-1:11 | SEQ0679 | 0.03324 | 0.858 | 0.757 |
| lnc-CHN1-5:11 | SEQ0419 | 0.02049 | 0.739 | 0.778 |
| lnc-CHRAC1-1:1 | SEQ0680 | 0.03324 | 0.747 | 0.757 |
| lnc-CHRAC1-6:1 | SEQ0420 | 0.02049 | 1.247 | 0.222 |
| lnc-CHRM2-1:1 | SEQ0121 | 0.00556 | 0.833 | 0.826 |
| lnc-CHRM3-1:5 | SEQ0681 | 0.03324 | 0.714 | 0.757 |
| lnc-CHST2-6:2 | SEQ0196 | 0.00829 | 0.763 | 0.813 |
| lnc-CLDN10-5:1 | SEQ0313 | 0.01449 | 0.717 | 0.792 |
| lnc-CLEC19A-3:1 | SEQ0787 | 0.03872 | 1.284 | 0.25 |
| lnc-CLK1-1:7 | SEQ0197 | 0.00829 | 0.602 | 0.813 |
| lnc-CLVS2-2:5 | SEQ0359 | 0.01727 | 0.818 | 0.785 |
| lnc-CMPK2-34:4 | SEQ0101 | 0.00451 | 0.651 | 0.833 |
| lnc-CMTM7-2:2 | SEQ0269 | 0.01209 | 0.838 | 0.799 |
| lnc-CMTR1-10:1 | SEQ0788 | 0.03872 | 0.868 | 0.75 |
| lnc-CNBD1-4:13 | SEQ0682 | 0.03324 | 0.568 | 0.757 |
| lnc-CNDP1-7:1 | SEQ0024 | 0.00086 | 0.534 | 0.882 |
| lnc-CNOT6-10:1 | SEQ0270 | 0.01209 | 1.19 | 0.201 |
| lnc-COL6A6-2:1 | SEQ0910 | 0.0449 | 0.717 | 0.743 |
| lnc-COMMD6-10:1 | SEQ0079 | 0.00364 | 1.58 | 0.16 |
| lnc-COX10-9:2 | SEQ0911 | 0.0449 | 0.849 | 0.743 |
| lnc-CPEB3-2:1 | SEQ0789 | 0.03872 | 0.78 | 0.75 |
| lnc-CPM-2:11 | SEQ0912 | 0.0449 | 0.424 | 0.743 |
| lnc-CPM-3:1 | SEQ0228 | 0.01004 | 0.831 | 0.806 |
| lnc-CRIPT-1:3 | SEQ0790 | 0.03872 | 0.802 | 0.75 |
| lnc-CRISP1-1:2 | SEQ0271 | 0.01209 | 0.685 | 0.799 |
| lnc-CRYBA1-4:1 | SEQ0421 | 0.02049 | 0.693 | 0.778 |
| lnc-CRYBB1-1:1 | SEQ0055 | 0.00232 | 0.487 | 0.854 |
| lnc-CSGALNACT2-2:3 | SEQ0791 | 0.03872 | 0.781 | 0.75 |
| lnc-CSNK1A1-6:1 | SEQ0030 | 0.00111 | 0.696 | 0.875 |
| lnc-CTIF-9:2 | SEQ0504 | 0.02418 | 1.28 | 0.229 |
| lnc-CTNNA2-3:11 | SEQ0198 | 0.00829 | 0.812 | 0.813 |
| lnc-CTNNA3-1:2 | SEQ0683 | 0.03324 | 0.82 | 0.757 |
| lnc-CTNND2-3:1 | SEQ0913 | 0.0449 | 0.797 | 0.743 |
| lnc-CTR9-7:1 | SEQ0914 | 0.0449 | 0.763 | 0.743 |
| lnc-CYB5R2-3:13 | SEQ0199 | 0.00829 | 0.749 | 0.813 |
| lnc-CYBA-4:3 | SEQ0150 | 0.00681 | 0.784 | 0.819 |
| lnc-CYP2E1-1:1 | SEQ0684 | 0.03324 | 1.733 | 0.243 |
| lnc-CYTIP-2:1 | SEQ0200 | 0.00829 | 0.727 | 0.813 |
| lnc-DAO-3:1 | SEQ0685 | 0.03324 | 1.109 | 0.243 |
| lnc-DAPP1-2:11 | SEQ0505 | 0.02418 | 0.822 | 0.771 |
| lnc-DAZAP2-3:1 | SEQ0056 | 0.00232 | 0.797 | 0.854 |
| lnc-DDX1-3:1 | SEQ0915 | 0.0449 | 1.251 | 0.257 |
| lnc-DDX18-1:1 | SEQ0506 | 0.02418 | 0.721 | 0.771 |
| lnc-DDX18-1:7 | SEQ0314 | 0.01449 | 0.755 | 0.792 |
| lnc-DEFB112-3:4 | SEQ0422 | 0.02049 | 0.565 | 0.778 |
| lnc-DEK-4:1 | SEQ0507 | 0.02418 | 0.715 | 0.771 |
| lnc-DEPTOR-5:3 | SEQ0360 | 0.01727 | 0.846 | 0.785 |

TABLE 5-continued

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| lnc-DGCR2-5:1 | SEQ0423 | 0.02049 | 0.872 | 0.778 |
| lnc-DGCR6-7:26 | SEQ0792 | 0.03872 | 0.736 | 0.75 |
| lnc-DHX37-18:1 | SEQ0229 | 0.01004 | 0.751 | 0.806 |
| lnc-DHX38-25:1 | SEQ0230 | 0.01004 | 0.894 | 0.806 |
| lnc-DKK1-5:3 | SEQ0005 | 0.00027 | 0.739 | 0.91 |
| lnc-DKK1-5:4 | SEQ0793 | 0.03872 | 0.893 | 0.75 |
| lnc-DLG5-1:1 | SEQ0034 | 0.00143 | 0.773 | 0.868 |
| lnc-DLX2-12:1 | SEQ0151 | 0.00681 | 0.747 | 0.819 |
| lnc-DMRTA1-17:1 | SEQ0201 | 0.00829 | 0.79 | 0.813 |
| lnc-DNAH9-1:1 | SEQ0508 | 0.02418 | 0.812 | 0.771 |
| lnc-DNALI1-5:4 | SEQ0102 | 0.00451 | 0.776 | 0.833 |
| lnc-DOCK7-7:1 | SEQ0015 | 0.00066 | 0.843 | 0.889 |
| lnc-DTWD2-14:1 | SEQ0361 | 0.01727 | 0.811 | 0.785 |
| lnc-DUSP10-6:1 | SEQ0057 | 0.00232 | 0.675 | 0.854 |
| lnc-DUSP26-3:2 | SEQ0031 | 0.00111 | 0.796 | 0.875 |
| lnc-DYNAP-1:1 | SEQ0604 | 0.02842 | 0.761 | 0.764 |
| lnc-EAF1-2:1 | SEQ0509 | 0.02418 | 0.737 | 0.771 |
| lnc-EBF3-1:6 | SEQ0686 | 0.03324 | 1.241 | 0.243 |
| lnc-EBLN1-1:4 | SEQ0016 | 0.00066 | 0.725 | 0.889 |
| lnc-EDDM13-5:11 | SEQ0231 | 0.01004 | 0.372 | 0.806 |
| lnc-EDDM13-5:3 | SEQ0035 | 0.00143 | 1.505 | 0.132 |
| lnc-EDEM3-7:3 | SEQ0272 | 0.01209 | 0.86 | 0.799 |
| lnc-EDRF1-1:5 | SEQ0916 | 0.0449 | 0.728 | 0.743 |
| lnc-EEF1AKMT1-3:6 | SEQ0202 | 0.00829 | 0.423 | 0.813 |
| lnc-EEF2-3:1 | SEQ0687 | 0.03324 | 1.301 | 0.243 |
| lnc-EFR3B-7:2 | SEQ0362 | 0.01727 | 0.821 | 0.785 |
| lnc-EGFR-7:1 | SEQ0917 | 0.0449 | 1.181 | 0.257 |
| lnc-EIF2AK3-31:7 | SEQ0918 | 0.0449 | 0.848 | 0.743 |
| lnc-EIF2AK3-4:81 | SEQ0688 | 0.03324 | 1.466 | 0.243 |
| lnc-ELF1-5:1 | SEQ0510 | 0.02418 | 0.799 | 0.771 |
| lnc-ELFN2-1:3 | SEQ0080 | 0.00364 | 0.764 | 0.84 |
| lnc-EPB42-1:3 | SEQ0689 | 0.03324 | 0.917 | 0.757 |
| lnc-EPHA7-3:1 | SEQ0081 | 0.00364 | 0.763 | 0.84 |
| lnc-ERCC6L2-10:2 | SEQ0605 | 0.02842 | 0.927 | 0.764 |
| lnc-ERCC6L2-6:1 | SEQ0363 | 0.01727 | 1.784 | 0.215 |
| lnc-ERFE-1:1 | SEQ0919 | 0.0449 | 0.489 | 0.743 |
| lnc-ERGIC2-2:2 | SEQ0364 | 0.01727 | 0.799 | 0.785 |
| lnc-ERH-1:1 | SEQ0424 | 0.02049 | 0.708 | 0.778 |
| lnc-ERICH1-9:1 | SEQ0920 | 0.0449 | 0.85 | 0.743 |
| lnc-ERV3-1-9:1 | SEQ0203 | 0.00829 | 1.32 | 0.188 |
| lnc-ESRP1-2:4 | SEQ0315 | 0.01449 | 0.542 | 0.792 |
| lnc-ETS1-2:2 | SEQ0082 | 0.00364 | 1.436 | 0.16 |
| lnc-EXOC2-21:6 | SEQ0204 | 0.00829 | 1.528 | 0.188 |
| lnc-EZH2-3:1 | SEQ0273 | 0.01209 | 0.79 | 0.799 |
| lnc-F11-8:1 | SEQ0690 | 0.03324 | 0.876 | 0.757 |
| lnc-F13A1-2:7 | SEQ0691 | 0.03324 | 1.485 | 0.243 |
| lnc-FAM133B-2:1 | SEQ0036 | 0.00143 | 0.767 | 0.868 |
| lnc-FAM171B-1:6 | SEQ0205 | 0.00829 | 0.851 | 0.813 |
| lnc-FAM19A3-6:3 | SEQ0274 | 0.01209 | 0.75 | 0.799 |
| lnc-FAM217A-1:2 | SEQ0032 | 0.00111 | 0.854 | 0.875 |
| lnc-FAM231B-2:1 | SEQ0511 | 0.02418 | 1.252 | 0.229 |
| lnc-FAM231B-2:2 | SEQ0512 | 0.02418 | 1.252 | 0.229 |
| lnc-FAM236D-2:1 | SEQ0692 | 0.03324 | 0.601 | 0.757 |
| lnc-FAM46C-3:1 | SEQ0794 | 0.03872 | 0.755 | 0.75 |
| lnc-FAM49B-8:1 | SEQ0010 | 0.0005 | 1.758 | 0.104 |
| lnc-FAM71F2-5:1 | SEQ0425 | 0.02049 | 0.642 | 0.778 |
| lnc-FAM72B-6:3 | SEQ0606 | 0.02842 | 1.327 | 0.236 |
| lnc-FAM84A-5:1 | SEQ0607 | 0.02842 | 0.697 | 0.764 |
| lnc-FAM84B-17:4 | SEQ0608 | 0.02842 | 0.741 | 0.764 |
| lnc-FAM84B-4:3 | SEQ0083 | 0.00364 | 0.803 | 0.84 |
| lnc-FAP-3:1 | SEQ0206 | 0.00829 | 0.749 | 0.813 |
| lnc-FARSB-6:1 | SEQ0232 | 0.01004 | 1.292 | 0.194 |
| lnc-FAT1-7:2 | SEQ0017 | 0.00066 | 1.383 | 0.111 |
| lnc-FAT4-6:1 | SEQ0609 | 0.02842 | 0.751 | 0.764 |
| lnc-FBRSL1-3:3 | SEQ0610 | 0.02842 | 1.645 | 0.236 |
| lnc-FCGR3B-4:11 | SEQ0513 | 0.02418 | 0.848 | 0.771 |
| lnc-FCGR3B-4:12 | SEQ0514 | 0.02418 | 0.848 | 0.771 |
| lnc-FER1L6-2:1 | SEQ0515 | 0.02418 | 0.779 | 0.771 |
| lnc-FGD4-8:1 | SEQ0233 | 0.01004 | 0.688 | 0.806 |
| lnc-FGD4-9:1 | SEQ0084 | 0.00364 | 0.711 | 0.84 |
| lnc-FILIP1L-3:1 | SEQ0058 | 0.00232 | 0.867 | 0.854 |
| lnc-FNBP1L-1:11 | SEQ0006 | 0.00027 | 0.743 | 0.91 |
| lnc-FOXC1-6:2 | SEQ0516 | 0.02418 | 0.736 | 0.771 |
| lnc-FOXD4L5-35:1 | SEQ0152 | 0.00681 | 1.878 | 0.181 |
| lnc-FOXO1-2:8 | SEQ0611 | 0.02842 | 1.402 | 0.236 |
| lnc-FRG2-13:3 | SEQ0275 | 0.01209 | 0.908 | 0.799 |
| lnc-FSIP1-6:4 | SEQ0795 | 0.03872 | 1.401 | 0.25 |
| lnc-FSIP2-2:1 | SEQ0921 | 0.0449 | 0.76 | 0.743 |
| lnc-FTCD-5:1 | SEQ0796 | 0.03872 | 0.722 | 0.75 |
| lnc-FTMT-2:14 | SEQ0517 | 0.02418 | 0.792 | 0.771 |
| lnc-GALC-9:8 | SEQ0234 | 0.01004 | 0.557 | 0.806 |
| lnc-GALNT2-1:1 | SEQ0426 | 0.02049 | 0.729 | 0.778 |
| lnc-GALNTL5-3:1 | SEQ0693 | 0.03324 | 0.759 | 0.757 |
| lnc-GCLC-1:13 | SEQ0922 | 0.0449 | 0.597 | 0.743 |
| lnc-GDPD5-6:1 | SEQ0153 | 0.00681 | 0.799 | 0.819 |
| lnc-GFI1B-2:3 | SEQ0797 | 0.03872 | 0.681 | 0.75 |
| lnc-GGH-3:1 | SEQ0798 | 0.03872 | 0.782 | 0.75 |
| lnc-GHR-1:1 | SEQ0003 | 0.0002 | 0.787 | 0.917 |
| lnc-GJC1-2:2 | SEQ0799 | 0.03872 | 0.832 | 0.75 |
| lnc-GJC1-2:3 | SEQ0800 | 0.03872 | 0.832 | 0.75 |
| lnc-GLIPR1-3:2 | SEQ0923 | 0.0449 | 0.923 | 0.743 |
| lnc-GLIPR1L1-2:3 | SEQ0427 | 0.02049 | 1.26 | 0.222 |
| lnc-GMDS-6:8 | SEQ0694 | 0.03324 | 0.721 | 0.757 |
| lnc-GNG5-8:1 | SEQ0695 | 0.03324 | 0.771 | 0.757 |
| lnc-GOLGA4-4:7 | SEQ0365 | 0.01727 | 0.855 | 0.785 |
| lnc-GOLGA6L6-9:1 | SEQ0069 | 0.00291 | 0.711 | 0.847 |
| lnc-GOLGA8F-2:1 | SEQ0235 | 0.01004 | 0.756 | 0.806 |
| lnc-GOLGA8O-5:6 | SEQ0428 | 0.02049 | 0.715 | 0.778 |
| lnc-GPAT4-1:3 | SEQ0316 | 0.01449 | 1.56 | 0.208 |
| lnc-GPATCH11-1:1 | SEQ0612 | 0.02842 | 0.703 | 0.764 |
| lnc-GPATCH2L-2:1 | SEQ0317 | 0.01449 | 0.85 | 0.792 |
| lnc-GPC2-2:5 | SEQ0518 | 0.02418 | 1.355 | 0.229 |
| lnc-GPR157-6:1 | SEQ0924 | 0.0449 | 0.827 | 0.743 |
| lnc-GPR161-4:1 | SEQ0070 | 0.00291 | 0.726 | 0.847 |
| lnc-GPR27-18:1 | SEQ0925 | 0.0449 | 0.774 | 0.743 |
| lnc-GPR33-14:1 | SEQ0236 | 0.01004 | 0.828 | 0.806 |
| lnc-GPR37-1:1 | SEQ0926 | 0.0449 | 0.793 | 0.743 |
| lnc-GPR39-10:2 | SEQ0154 | 0.00681 | 1.393 | 0.181 |
| lnc-GPRC5A-4:1 | SEQ0613 | 0.02842 | 0.717 | 0.764 |
| lnc-GPRC6A-2:1 | SEQ0927 | 0.0449 | 0.865 | 0.743 |
| lnc-GPSM1-3:3 | SEQ0928 | 0.0449 | 0.64 | 0.743 |
| lnc-GRAMD2B-4:1 | SEQ0801 | 0.03872 | 0.879 | 0.75 |
| lnc-GRIP1-1:2 | SEQ0429 | 0.02049 | 1.564 | 0.222 |
| lnc-GRIP1-5:2 | SEQ0519 | 0.02418 | 0.914 | 0.771 |
| lnc-GRIP1-8:1 | SEQ0802 | 0.03872 | 1.339 | 0.25 |
| lnc-GRM1-1:19 | SEQ0929 | 0.0449 | 1.338 | 0.257 |
| lnc-GRM1-1:31 | SEQ0155 | 0.00681 | 0.864 | 0.819 |
| lnc-GRM1-1:32 | SEQ0156 | 0.00681 | 0.864 | 0.819 |
| lnc-GRM8-2:2 | SEQ0430 | 0.02049 | 0.902 | 0.778 |
| lnc-GSN-2:4 | SEQ0930 | 0.0449 | 0.94 | 0.743 |
| lnc-GSN-2:5 | SEQ0803 | 0.03872 | 0.955 | 0.75 |
| lnc-GTDC1-28:5 | SEQ0157 | 0.00681 | 0.725 | 0.819 |
| lnc-GUCY1A3-1:1 | SEQ0520 | 0.02418 | 0.724 | 0.771 |
| lnc-GUSB-1:1 | SEQ0931 | 0.0449 | 0.829 | 0.743 |
| lnc-HECA-3:13 | SEQ0237 | 0.01004 | 0.8 | 0.806 |
| lnc-HECA-6:1 | SEQ0007 | 0.00037 | 0.723 | 0.903 |
| lnc-HELT-6:1 | SEQ0932 | 0.0449 | 0.784 | 0.743 |
| lnc-HHATL-2:1 | SEQ0933 | 0.0449 | 1.127 | 0.257 |
| lnc-HHLA2-2:1 | SEQ0696 | 0.03324 | 1.238 | 0.243 |
| lnc-HJURP-7:1 | SEQ0431 | 0.02049 | 0.776 | 0.778 |
| lnc-HLCS-5:1 | SEQ0238 | 0.01004 | 0.866 | 0.806 |
| lnc-HMG20A-1:2 | SEQ0432 | 0.02049 | 0.513 | 0.778 |
| lnc-HMGA1-2:3 | SEQ0804 | 0.03872 | 1.288 | 0.25 |
| lnc-HMGN1-2:1 | SEQ0433 | 0.02049 | 1.424 | 0.222 |
| lnc-HOMEZ-4:1 | SEQ0434 | 0.02049 | 0.848 | 0.778 |
| lnc-HOXC4-1:3 | SEQ0805 | 0.03872 | 0.845 | 0.75 |
| lnc-HS3ST3A1-1:1 | SEQ0239 | 0.01004 | 0.75 | 0.806 |
| lnc-HS6ST1-8:1 | SEQ0697 | 0.03324 | 1.344 | 0.243 |
| lnc-HSCB-2:1 | SEQ0614 | 0.02842 | 0.742 | 0.764 |
| lnc-HSD17B11-2:1 | SEQ0276 | 0.01209 | 0.792 | 0.799 |
| lnc-IFRD2-6:1 | SEQ0806 | 0.03872 | 1.31 | 0.25 |
| lnc-IFT80-8:1 | SEQ0934 | 0.0449 | 0.916 | 0.743 |
| lnc-IL6-8:4 | SEQ0318 | 0.01449 | 0.77 | 0.792 |
| lnc-IPO5-7:1 | SEQ0521 | 0.02418 | 0.869 | 0.771 |
| lnc-IQCF6-2:3 | SEQ0807 | 0.03872 | 2.026 | 0.25 |
| lnc-IRF2BP2-11:3 | SEQ0103 | 0.00451 | 1.403 | 0.167 |
| lnc-IRF6-1:1 | SEQ0808 | 0.03872 | 0.894 | 0.75 |
| lnc-IRS1-2:5 | SEQ0615 | 0.02842 | 1.878 | 0.236 |

TABLE 5-continued

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| lnc-IRS1-6:1 | SEQ0037 | 0.00143 | 0.804 | 0.868 |
| lnc-IRS1-7:3 | SEQ0522 | 0.02418 | 1.153 | 0.229 |
| lnc-IRX2-10:1 | SEQ0698 | 0.03324 | 0.744 | 0.757 |
| lnc-ITGB8-2:8 | SEQ0616 | 0.02842 | 0.805 | 0.764 |
| lnc-JMJD4-2:1 | SEQ0435 | 0.02049 | 0.736 | 0.778 |
| lnc-JRK-2:1 | SEQ0935 | 0.0449 | 1.162 | 0.257 |
| lnc-JRK-2:2 | SEQ0699 | 0.03324 | 0.764 | 0.757 |
| lnc-KAT5-2:1 | SEQ0936 | 0.0449 | 0.769 | 0.743 |
| lnc-KBTBD7-1:1 | SEQ0523 | 0.02418 | 0.742 | 0.771 |
| lnc-KBTBD8-4:3 | SEQ0366 | 0.01727 | 1.457 | 0.215 |
| lnc-KCNA1-1:23 | SEQ0122 | 0.00556 | 0.633 | 0.826 |
| lnc-KCND3-1:1 | SEQ0085 | 0.00364 | 0.808 | 0.84 |
| lnc-KCNE1B-15:1 | SEQ0319 | 0.01449 | 0.823 | 0.792 |
| lnc-KCNS3-9:1 | SEQ0320 | 0.01449 | 1.265 | 0.208 |
| lnc-KCTD13-3:1 | SEQ0700 | 0.03324 | 0.709 | 0.757 |
| lnc-KCTD19-1:1 | SEQ0701 | 0.03324 | 0.761 | 0.757 |
| lnc-KDM3A-1:4 | SEQ0104 | 0.00451 | 0.731 | 0.833 |
| lnc-KDM8-3:1 | SEQ0436 | 0.02049 | 0.758 | 0.778 |
| lnc-KIAA0141-3:1 | SEQ0702 | 0.03324 | 1.15 | 0.243 |
| lnc-KIF21B-2:1 | SEQ0937 | 0.0449 | 0.873 | 0.743 |
| lnc-KIN-5:1 | SEQ0703 | 0.03324 | 0.835 | 0.757 |
| lnc-KLF11-1:8 | SEQ0704 | 0.03324 | 0.286 | 0.757 |
| lnc-KLF12-4:1 | SEQ0938 | 0.0449 | 0.806 | 0.743 |
| lnc-KLF12-7:1 | SEQ0240 | 0.01004 | 0.88 | 0.806 |
| lnc-KLHL24-2:1 | SEQ0321 | 0.01449 | 1.206 | 0.208 |
| lnc-KLK2-4:3 | SEQ0524 | 0.02418 | 0.881 | 0.771 |
| lnc-KLRG1-8:1 | SEQ0809 | 0.03872 | 1.222 | 0.25 |
| lnc-KREMEN2-1:1 | SEQ0705 | 0.03324 | 1.279 | 0.243 |
| lnc-KRR1-4:7 | SEQ0706 | 0.03324 | 0.801 | 0.757 |
| lnc-KY-4:1 | SEQ0123 | 0.00556 | 0.708 | 0.826 |
| lnc-L3MBTL2-1:1 | SEQ0367 | 0.01727 | 1.259 | 0.215 |
| lnc-LARP1B-1:15 | SEQ0277 | 0.01209 | 0.786 | 0.799 |
| lnc-LARP1B-1:17 | SEQ0278 | 0.01209 | 0.786 | 0.799 |
| lnc-LARP1B-1:18 | SEQ0279 | 0.01209 | 1.214 | 0.201 |
| lnc-LARP4-6:1 | SEQ0368 | 0.01727 | 0.803 | 0.785 |
| lnc-LBH-4:1 | SEQ0707 | 0.03324 | 1.312 | 0.243 |
| lnc-LBX1-1:1 | SEQ0241 | 0.01004 | 0.788 | 0.806 |
| lnc-LEPROTL1-12:1 | SEQ0011 | 0.0005 | 0.749 | 0.896 |
| lnc-LIMS3-1:10 | SEQ0086 | 0.00364 | 2.27 | 0.16 |
| lnc-LINC00675-1:3 | SEQ0810 | 0.03872 | 0.669 | 0.75 |
| lnc-LINS1-2:1 | SEQ0811 | 0.03872 | 0.81 | 0.75 |
| lnc-LMBRD1-5:17 | SEQ0812 | 0.03872 | 0.574 | 0.75 |
| lnc-LMX1A-2:1 | SEQ0708 | 0.03324 | 0.786 | 0.757 |
| lnc-LONP2-6:10 | SEQ0280 | 0.01209 | 0.912 | 0.799 |
| lnc-LRCH1-1:1 | SEQ0437 | 0.02049 | 0.793 | 0.778 |
| lnc-LRP12-4:3 | SEQ0939 | 0.0449 | 1.165 | 0.257 |
| lnc-LRP5L-2:14 | SEQ0940 | 0.0449 | 1.203 | 0.257 |
| lnc-LRR1-1:2 | SEQ0813 | 0.03872 | 0.729 | 0.75 |
| lnc-LRR1-1:3 | SEQ0814 | 0.03872 | 0.725 | 0.75 |
| lnc-LRRC1-5:2 | SEQ0087 | 0.00364 | 0.649 | 0.84 |
| lnc-LRRC3B-1:3 | SEQ0941 | 0.0449 | 0.463 | 0.743 |
| lnc-LRRC41-3:2 | SEQ0942 | 0.0449 | 1.272 | 0.257 |
| lnc-LRRC4C-7:1 | SEQ0815 | 0.03872 | 0.818 | 0.75 |
| lnc-LRRFIP2-3:4 | SEQ0617 | 0.02842 | 0.74 | 0.764 |
| lnc-LRRK1-3:4 | SEQ0242 | 0.01004 | 0.79 | 0.806 |
| lnc-LRRK2-1:10 | SEQ0369 | 0.01727 | 0.86 | 0.785 |
| lnc-LRRK2-1:9 | SEQ0370 | 0.01727 | 0.86 | 0.785 |
| lnc-LRRTM4-3:2 | SEQ0618 | 0.02842 | 0.865 | 0.764 |
| lnc-LY9-3:1 | SEQ0207 | 0.00829 | 1.317 | 0.188 |
| lnc-LYN-8:1 | SEQ0619 | 0.02842 | 1.516 | 0.236 |
| lnc-MAFB-1:4 | SEQ0525 | 0.02418 | 0.839 | 0.771 |
| lnc-MAMDC2-1:1 | SEQ0526 | 0.02418 | 0.828 | 0.771 |
| lnc-MAML3-2:1 | SEQ0438 | 0.02049 | 0.768 | 0.778 |
| lnc-MAN1A1-1:3 | SEQ0158 | 0.00681 | 0.722 | 0.819 |
| lnc-MAP9-6:1 | SEQ0281 | 0.01209 | 0.741 | 0.799 |
| lnc-MARCH4-2:7 | SEQ0088 | 0.00364 | 2 | 0.16 |
| lnc-MARCKS-1:9 | SEQ0527 | 0.02418 | 0.717 | 0.771 |
| lnc-MASTL-2:1 | SEQ0943 | 0.0449 | 0.756 | 0.743 |
| lnc-MB-3:1 | SEQ0944 | 0.0449 | 1.302 | 0.257 |
| lnc-MBP-16:2 | SEQ0208 | 0.00829 | 1.204 | 0.188 |
| lnc-MC5R-5:1 | SEQ0945 | 0.0449 | 0.742 | 0.743 |
| lnc-MC5R-6:2 | SEQ0243 | 0.01004 | 0.626 | 0.806 |
| lnc-MDM4-8:1 | SEQ0816 | 0.03872 | 0.791 | 0.75 |
| lnc-ME3-1:1 | SEQ0946 | 0.0449 | 1.353 | 0.257 |
| lnc-MED10-23:1 | SEQ0209 | 0.00829 | 1.295 | 0.188 |
| lnc-MED15-1:2 | SEQ0620 | 0.02842 | 1.191 | 0.236 |
| lnc-MESD-6:1 | SEQ0947 | 0.0449 | 0.762 | 0.743 |
| lnc-MEST-6:1 | SEQ0124 | 0.00556 | 0.817 | 0.826 |
| lnc-METTL22-11:1 | SEQ0709 | 0.03324 | 0.747 | 0.757 |
| lnc-MFSD8-6:3 | SEQ0528 | 0.02418 | 0.845 | 0.771 |
| lnc-MFSD8-6:8 | SEQ0371 | 0.01727 | 0.794 | 0.785 |
| lnc-MGST3-1:3 | SEQ0043 | 0.00183 | 1.664 | 0.139 |
| lnc-MIB1-1:1 | SEQ0159 | 0.00681 | 0.68 | 0.819 |
| lnc-MNX1-10:1 | SEQ0322 | 0.01449 | 1.204 | 0.208 |
| lnc-MOGAT1-3:2 | SEQ0948 | 0.0449 | 0.703 | 0.743 |
| lnc-MPLKIP-3:1 | SEQ0710 | 0.03324 | 0.867 | 0.757 |
| lnc-MPP4-3:1 | SEQ0817 | 0.03872 | 0.813 | 0.75 |
| lnc-MRC2-2:1 | SEQ0818 | 0.03872 | 0.835 | 0.75 |
| lnc-MRGPRD-2:1 | SEQ0244 | 0.01004 | 0.79 | 0.806 |
| lnc-MRGPRF-4:4 | SEQ0105 | 0.00451 | 0.604 | 0.833 |
| lnc-MROH7-2:1 | SEQ0529 | 0.02418 | 0.844 | 0.771 |
| lnc-MRPL57-5:8 | SEQ0621 | 0.02842 | 0.855 | 0.764 |
| lnc-MRPS30-13:1 | SEQ0819 | 0.03872 | 0.814 | 0.75 |
| lnc-MSH2-3:2 | SEQ0711 | 0.03324 | 1.401 | 0.243 |
| lnc-MTRNR2L1-3:1 | SEQ0530 | 0.02418 | 1.325 | 0.229 |
| lnc-MVB12B-6:1 | SEQ0531 | 0.02418 | 0.811 | 0.771 |
| lnc-MYC-12:1 | SEQ0622 | 0.02842 | 1.418 | 0.236 |
| lnc-MYO18B-2:3 | SEQ0323 | 0.01449 | 0.833 | 0.792 |
| lnc-MYO18B-3:3 | SEQ0160 | 0.00681 | 0.762 | 0.819 |
| lnc-MYOCOS-2:1 | SEQ0439 | 0.02049 | 0.891 | 0.778 |
| lnc-NAA38-3:1 | SEQ0532 | 0.02418 | 0.854 | 0.771 |
| lnc-NAALADL2-8:1 | SEQ0324 | 0.01449 | 0.864 | 0.792 |
| lnc-NANOS1-3:1 | SEQ0712 | 0.03324 | 1.277 | 0.243 |
| lnc-NAXD-6:5 | SEQ0125 | 0.00556 | 0.479 | 0.826 |
| lnc-NBPF14-1:2 | SEQ0089 | 0.00364 | 0.815 | 0.84 |
| lnc-NBPF14-3:1 | SEQ0623 | 0.02842 | 0.889 | 0.764 |
| lnc-NCR3LG1-3:1 | SEQ0018 | 0.00066 | 0.837 | 0.889 |
| lnc-NDFIP2-7:13 | SEQ0820 | 0.03872 | 0.775 | 0.75 |
| lnc-NDFIP2-7:14 | SEQ0440 | 0.02049 | 0.77 | 0.778 |
| lnc-NDRG2-5:1 | SEQ0949 | 0.0449 | 0.773 | 0.743 |
| lnc-NDUFA10-6:1 | SEQ0161 | 0.00681 | 0.712 | 0.819 |
| lnc-NDUFB9-2:2 | SEQ0713 | 0.03324 | 1.345 | 0.243 |
| lnc-NDUFS6-15:1 | SEQ0950 | 0.0449 | 0.805 | 0.743 |
| lnc-NEUROD2-4:1 | SEQ0071 | 0.00291 | 0.772 | 0.847 |
| lnc-NKAIN2-5:1 | SEQ0821 | 0.03872 | 0.794 | 0.75 |
| lnc-NKX6-1-2:1 | SEQ0282 | 0.01209 | 0.773 | 0.799 |
| lnc-NOC2L-1:21 | SEQ0245 | 0.01004 | 1.382 | 0.194 |
| lnc-NOC2L-12:1 | SEQ0372 | 0.01727 | 1.479 | 0.215 |
| lnc-NOS2-7:1 | SEQ0951 | 0.0449 | 1.203 | 0.257 |
| lnc-NPBWR1-2:2 | SEQ0952 | 0.0449 | 1.517 | 0.257 |
| lnc-NPIPB12-1:1 | SEQ0822 | 0.03872 | 1.13 | 0.25 |
| lnc-PAPPA-1:3 | SEQ0720 | 0.03324 | 2.192 | 0.243 |
| lnc-PAPPA-1:4 | SEQ0721 | 0.03324 | 0.814 | 0.757 |
| lnc-PAPPA2-1:10 | SEQ0246 | 0.01004 | 0.753 | 0.806 |
| lnc-PAPPA2-7:1 | SEQ0165 | 0.00681 | 0.839 | 0.819 |
| lnc-PATE2-1:1 | SEQ0247 | 0.01004 | 0.728 | 0.806 |
| lnc-PAX8-6:2 | SEQ0538 | 0.02418 | 1.413 | 0.229 |
| lnc-PAXIP1-8:1 | SEQ0957 | 0.0449 | 0.731 | 0.743 |
| lnc-PCDH10-11:1 | SEQ0958 | 0.0449 | 0.719 | 0.743 |
| lnc-PCDH8-12:1 | SEQ0166 | 0.00681 | 0.742 | 0.819 |
| lnc-PCOLCE2-1:1 | SEQ0959 | 0.0449 | 0.909 | 0.743 |
| lnc-PCSK9-4:6 | SEQ0327 | 0.01449 | 1.154 | 0.208 |
| lnc-PCSK9-4:9 | SEQ0328 | 0.01449 | 1.154 | 0.208 |
| lnc-PDLIM1-3:1 | SEQ0960 | 0.0449 | 0.837 | 0.743 |
| lnc-PFKP-16:15 | SEQ0628 | 0.02842 | 0.662 | 0.764 |
| lnc-PFKP-17:1 | SEQ0445 | 0.02049 | 0.834 | 0.778 |
| lnc-PHF14-14:19 | SEQ0825 | 0.03872 | 0.678 | 0.75 |
| lnc-PIGB-1:5 | SEQ0539 | 0.02418 | 0.691 | 0.771 |
| lnc-PIGM-4:1 | SEQ0248 | 0.01004 | 0.715 | 0.806 |
| lnc-PINX1-7:1 | SEQ0329 | 0.01449 | 1.307 | 0.208 |
| lnc-PLA2G2F-1:2 | SEQ0285 | 0.01209 | 1.224 | 0.201 |
| lnc-PLA2G4A-7:5 | SEQ0446 | 0.02049 | 0.865 | 0.778 |
| lnc-PLA2G4A-7:8 | SEQ0826 | 0.03872 | 0.74 | 0.75 |
| lnc-PLAT-1:3 | SEQ0961 | 0.0449 | 0.738 | 0.743 |
| lnc-PLCB1-7:2 | SEQ0827 | 0.03872 | 0.854 | 0.75 |
| lnc-PLEKHA8-3:5 | SEQ0962 | 0.0449 | 0.793 | 0.743 |
| lnc-PLK1-1:6 | SEQ0963 | 0.0449 | 0.663 | 0.743 |
| lnc-PLN-2:1 | SEQ0722 | 0.03324 | 0.781 | 0.757 |

TABLE 5-continued

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| lnc-PLSCR2-2:1 | SEQ0964 | 0.0449 | 0.813 | 0.743 |
| lnc-POC5-3:1 | SEQ0629 | 0.02842 | 0.747 | 0.764 |
| lnc-POLE4-3:1 | SEQ0330 | 0.01449 | 0.798 | 0.792 |
| lnc-POU2AF1-1:2 | SEQ0447 | 0.02049 | 0.874 | 0.778 |
| lnc-PPIAL4F-3:2 | SEQ0828 | 0.03872 | 1.302 | 0.25 |
| lnc-PPM1D-1:8 | SEQ0540 | 0.02418 | 0.8 | 0.771 |
| lnc-PPP2R3C-4:1 | SEQ0025 | 0.00086 | 0.879 | 0.882 |
| lnc-PPP5C-4:1 | SEQ0723 | 0.03324 | 0.757 | 0.757 |
| lnc-PRDM9-19:2 | SEQ0829 | 0.03872 | 0.709 | 0.75 |
| lnc-PRDM9-20:1 | SEQ0376 | 0.01727 | 0.678 | 0.785 |
| lnc-PRELID2-1:2 | SEQ0541 | 0.02418 | 1.232 | 0.229 |
| lnc-PRKACG-1:2 | SEQ0724 | 0.03324 | 0.738 | 0.757 |
| lnc-PRKACG-2:1 | SEQ0630 | 0.02842 | 1.186 | 0.236 |
| lnc-PRKCH-1:1 | SEQ0286 | 0.01209 | 0.904 | 0.799 |
| lnc-PRKN-8:1 | SEQ0212 | 0.00829 | 1.368 | 0.188 |
| lnc-PRND-2:1 | SEQ0287 | 0.01209 | 0.798 | 0.799 |
| lnc-PRR11-1:4 | SEQ0288 | 0.01209 | 0.862 | 0.799 |
| lnc-PRR5-5:1 | SEQ0167 | 0.00681 | 0.703 | 0.819 |
| lnc-PRSS54-2:2 | SEQ0168 | 0.00681 | 0.769 | 0.819 |
| lnc-PSMB1-6:4 | SEQ0331 | 0.01449 | 2.134 | 0.208 |
| lnc-PTDSS1-1:2 | SEQ0448 | 0.02049 | 1.246 | 0.222 |
| lnc-PTP4A2-1:2 | SEQ0725 | 0.03324 | 1.223 | 0.243 |
| lnc-PTPN14-11:1 | SEQ0449 | 0.02049 | 1.341 | 0.222 |
| lnc-PTPN4-1:1 | SEQ0631 | 0.02842 | 0.755 | 0.764 |
| lnc-QRFP-5:1 | SEQ0019 | 0.00066 | 2.17 | 0.111 |
| lnc-RAB3B-1:1 | SEQ0965 | 0.0449 | 0.843 | 0.743 |
| lnc-RAB6C-3:1 | SEQ0966 | 0.0449 | 0.836 | 0.743 |
| lnc-RAI14-3:1 | SEQ0542 | 0.02418 | 0.835 | 0.771 |
| lnc-RALGAPA1-1:2 | SEQ0726 | 0.03324 | 0.86 | 0.757 |
| lnc-RALGAPA2-2:4 | SEQ0967 | 0.0449 | 0.805 | 0.743 |
| lnc-RARRES1-3:2 | SEQ0632 | 0.02842 | 0.84 | 0.764 |
| lnc-RASGRP1-3:3 | SEQ0968 | 0.0449 | 0.796 | 0.743 |
| lnc-RBFOX1-2:1 | SEQ0377 | 0.01727 | 1.269 | 0.215 |
| lnc-RBKS-6:1 | SEQ0128 | 0.00556 | 0.802 | 0.826 |
| lnc-RBM11-11:1 | SEQ0450 | 0.02049 | 0.714 | 0.778 |
| lnc-RBM25-1:1 | SEQ0969 | 0.0449 | 0.89 | 0.743 |
| lnc-RBM33-3:1 | SEQ0727 | 0.03324 | 0.762 | 0.757 |
| lnc-RBM45-7:1 | SEQ0830 | 0.03872 | 0.792 | 0.75 |
| lnc-RBMS1-7:1 | SEQ0249 | 0.01004 | 0.778 | 0.806 |
| lnc-RCSD1-4:1 | SEQ0831 | 0.03872 | 0.831 | 0.75 |
| lnc-RDH13-1:2 | SEQ0250 | 0.01004 | 0.635 | 0.806 |
| lnc-RGMA-28:2 | SEQ0378 | 0.01727 | 0.875 | 0.785 |
| lnc-RGS9-15:6 | SEQ0970 | 0.0449 | 0.705 | 0.743 |
| lnc-RHNO1-1:1 | SEQ0026 | 0.00086 | 1.248 | 0.118 |
| lnc-RHOB-1:3 | SEQ0451 | 0.02049 | 0.612 | 0.778 |
| lnc-RHOB-21:1 | SEQ0971 | 0.0449 | 0.817 | 0.743 |
| lnc-RHOBTB2-4:1 | SEQ0213 | 0.00829 | 0.839 | 0.813 |
| lnc-RIPPLY3-1:3 | SEQ0832 | 0.03872 | 0.889 | 0.75 |
| lnc-RIT2-5:1 | SEQ0289 | 0.01209 | 1.302 | 0.201 |
| lnc-RNF6-2:1 | SEQ0059 | 0.00232 | 0.692 | 0.854 |
| lnc-RNFT2-1:5 | SEQ0379 | 0.01727 | 0.8 | 0.785 |
| lnc-RNLS-1:1 | SEQ0972 | 0.0449 | 0.829 | 0.743 |
| lnc-ROBO2-16:1 | SEQ0251 | 0.01004 | 0.799 | 0.806 |
| lnc-RPE65-4:2 | SEQ0129 | 0.00556 | 0.857 | 0.826 |
| lnc-RPIA-25:1 | SEQ0130 | 0.00556 | 0.866 | 0.826 |
| lnc-RPL10L-5:1 | SEQ0452 | 0.02049 | 0.77 | 0.778 |
| lnc-RPL24-6:1 | SEQ0728 | 0.03324 | 1.245 | 0.243 |
| lnc-RPL35-2:1 | SEQ0543 | 0.02418 | 0.812 | 0.771 |
| lnc-RPL37-2:1 | SEQ0214 | 0.00829 | 1.309 | 0.188 |
| lnc-RPRM-7:1 | SEQ0380 | 0.01727 | 0.679 | 0.785 |
| lnc-RPS12-4:1 | SEQ0633 | 0.02842 | 0.806 | 0.764 |
| lnc-RPS21-4:2 | SEQ0027 | 0.00086 | 0.664 | 0.882 |
| lnc-RRM1-2:5 | SEQ0973 | 0.0449 | 0.934 | 0.743 |
| lnc-RSL1D1-2:1 | SEQ0215 | 0.00829 | 0.762 | 0.813 |
| lnc-RTL1-3:9 | SEQ0544 | 0.02418 | 0.848 | 0.771 |
| lnc-RUBCN-1:1 | SEQ0833 | 0.03872 | 0.788 | 0.75 |
| lnc-S1PR1-13:1 | SEQ0381 | 0.01727 | 0.686 | 0.785 |
| lnc-SAMD11-1:1 | SEQ0729 | 0.03324 | 1.247 | 0.243 |
| lnc-SAMD5-1:10 | SEQ0090 | 0.00364 | 0.708 | 0.84 |
| lnc-SC5D-4:1 | SEQ0730 | 0.03324 | 1.249 | 0.243 |
| lnc-SCD-7:1 | SEQ0974 | 0.0449 | 0.731 | 0.743 |
| lnc-SCGB1C2-8:1 | SEQ0975 | 0.0449 | 0.776 | 0.743 |
| lnc-SCNN1B-3:1 | SEQ0976 | 0.0449 | 1.155 | 0.257 |
| lnc-SCTR-2:4 | SEQ0634 | 0.02842 | 0.852 | 0.764 |
| lnc-SEPT14-6:1 | SEQ0545 | 0.02418 | 0.878 | 0.771 |
| lnc-SERHL2-1:8 | SEQ0546 | 0.02418 | 1.483 | 0.229 |
| lnc-SERINC1-8:3 | SEQ0731 | 0.03324 | 0.827 | 0.757 |
| lnc-SERP1-4:6 | SEQ0072 | 0.00291 | 0.719 | 0.847 |
| lnc-SERP1-4:8 | SEQ0977 | 0.0449 | 0.831 | 0.743 |
| lnc-SERPINI1-14:1 | SEQ0978 | 0.0449 | 0.85 | 0.743 |
| lnc-SERTM1-1:1 | SEQ0290 | 0.01209 | 0.817 | 0.799 |
| lnc-SFPQ-2:1 | SEQ0169 | 0.00681 | 0.72 | 0.819 |
| lnc-SGCG-7:2 | SEQ0453 | 0.02049 | 0.733 | 0.778 |
| lnc-SGK1-3:14 | SEQ0979 | 0.0449 | 1.836 | 0.257 |
| lnc-SGMS1-4:1 | SEQ0834 | 0.03872 | 0.793 | 0.75 |
| lnc-SH3BGRL2-4:1 | SEQ0980 | 0.0449 | 1.174 | 0.257 |
| lnc-SKIL-2:3 | SEQ0981 | 0.0449 | 1.222 | 0.257 |
| lnc-SLC1A3-1:1 | SEQ0547 | 0.02418 | 0.791 | 0.771 |
| lnc-SLC22A23-11:2 | SEQ0732 | 0.03324 | 1.239 | 0.243 |
| lnc-SLC25A21-1:1 | SEQ0733 | 0.03324 | 0.77 | 0.757 |
| lnc-SLC25A24-2:1 | SEQ0548 | 0.02418 | 0.883 | 0.771 |
| lnc-SLC25A30-2:4 | SEQ0291 | 0.01209 | 1.539 | 0.201 |
| lnc-SLC2A10-1:1 | SEQ0549 | 0.02418 | 0.788 | 0.771 |
| lnc-SLC38A2-1:11 | SEQ0252 | 0.01004 | 0.892 | 0.806 |
| lnc-SLC38A2-1:15 | SEQ0332 | 0.01449 | 1.425 | 0.208 |
| lnc-SLC39A11-10:11 | SEQ0292 | 0.01209 | 4.38 | 0.201 |
| lnc-SLC46A3-7:1 | SEQ0550 | 0.02418 | 0.858 | 0.771 |
| lnc-SLCO6A1-2:1 | SEQ0635 | 0.02842 | 0.775 | 0.764 |
| lnc-SLITRK5-17:1 | SEQ0293 | 0.01209 | 0.636 | 0.799 |
| lnc-SLTM-1:2 | SEQ0982 | 0.0449 | 0.9 | 0.743 |
| lnc-SMARCA5-4:18 | SEQ0253 | 0.01004 | 0.825 | 0.806 |
| lnc-SMIM14-4:1 | SEQ0454 | 0.02049 | 0.788 | 0.778 |
| lnc-SMIM17-5:4 | SEQ0734 | 0.03324 | 0.715 | 0.757 |
| lnc-SNAPC3-12:5 | SEQ0455 | 0.02049 | 1.387 | 0.222 |
| lnc-SNCA-3:1 | SEQ0551 | 0.02418 | 0.498 | 0.771 |
| lnc-SNRPB2-2:4 | SEQ0254 | 0.01004 | 1.727 | 0.194 |
| lnc-SNX10-6:1 | SEQ0636 | 0.02842 | 0.764 | 0.764 |
| lnc-SNX13-2:6 | SEQ0456 | 0.02049 | 1.576 | 0.222 |
| lnc-SNX16-6:1 | SEQ0983 | 0.0449 | 0.83 | 0.743 |
| lnc-SNX17-1:13 | SEQ0333 | 0.01449 | 1.985 | 0.208 |
| lnc-SNX17-1:8 | SEQ0984 | 0.0449 | 0.754 | 0.743 |
| lnc-SNX19-6:1 | SEQ0835 | 0.03872 | 1.249 | 0.25 |
| lnc-SNX19-9:1 | SEQ0836 | 0.03872 | 0.837 | 0.75 |
| lnc-SNX20-8:5 | SEQ0985 | 0.0449 | 0.933 | 0.743 |
| lnc-SOX11-5:1 | SEQ0382 | 0.01727 | 1.216 | 0.215 |
| lnc-SOX14-2:1 | SEQ0045 | 0.00183 | 0.837 | 0.861 |
| lnc-SPAG9-2:1 | SEQ0383 | 0.01727 | 0.851 | 0.785 |
| lnc-SPAG9-2:2 | SEQ0384 | 0.01727 | 0.851 | 0.785 |
| lnc-SPATA31A6-10:1 | SEQ0837 | 0.03872 | 0.804 | 0.75 |
| lnc-SPATA31D4-1:6 | SEQ0838 | 0.03872 | 0.718 | 0.75 |
| lnc-SPP1-1:1 | SEQ0046 | 0.00183 | 0.846 | 0.861 |
| lnc-SPRY1-9:1 | SEQ0839 | 0.03872 | 0.767 | 0.75 |
| lnc-SPTSSA-5:2 | SEQ0552 | 0.02418 | 1.31 | 0.229 |
| lnc-SRCIN1-1:18 | SEQ0553 | 0.02418 | 0.798 | 0.771 |
| lnc-SRSF2-2:5 | SEQ0735 | 0.03324 | 0.633 | 0.757 |
| lnc-ST8SIA4-3:5 | SEQ0457 | 0.02049 | 1.584 | 0.222 |
| lnc-STARD10-1:6 | SEQ0840 | 0.03872 | 1.156 | 0.25 |
| lnc-STAT1-2:3 | SEQ0986 | 0.0449 | 0.832 | 0.743 |
| lnc-STK32B-2:1 | SEQ0170 | 0.00681 | 0.807 | 0.819 |
| lnc-STOML3-6:1 | SEQ0038 | 0.00143 | 0.731 | 0.868 |
| lnc-STPG1-1:1 | SEQ0637 | 0.02842 | 0.82 | 0.764 |
| lnc-STRADB-6:2 | SEQ0987 | 0.0449 | 0.723 | 0.743 |
| lnc-SUCLA2-13:2 | SEQ0736 | 0.03324 | 1.22 | 0.243 |
| lnc-SUCLA2-13:3 | SEQ0737 | 0.03324 | 1.22 | 0.243 |
| lnc-SUGT1-3:1 | SEQ0131 | 0.00556 | 2.047 | 0.174 |
| lnc-SULT1A4-1:27 | SEQ0841 | 0.03872 | 1.274 | 0.25 |
| lnc-SULT1C2-3:1 | SEQ0842 | 0.03872 | 1.396 | 0.25 |
| lnc-SUSD1-1:5 | SEQ0638 | 0.02842 | 0.798 | 0.764 |
| lnc-SYCP1-4:1 | SEQ0843 | 0.03872 | 1.204 | 0.25 |
| lnc-TAAR9-3:2 | SEQ0738 | 0.03324 | 0.806 | 0.757 |
| lnc-TAB2-1:4 | SEQ0988 | 0.0449 | 0.846 | 0.743 |
| lnc-TACC2-8:6 | SEQ0171 | 0.00681 | 0.869 | 0.819 |
| lnc-TACSTD2-2:4 | SEQ0020 | 0.00066 | 0.757 | 0.889 |
| lnc-TADA2B-6:1 | SEQ0554 | 0.02418 | 1.467 | 0.229 |
| lnc-TAF9-10:1 | SEQ0639 | 0.02842 | 0.825 | 0.764 |
| lnc-TASP1-11:1 | SEQ0989 | 0.0449 | 1.217 | 0.257 |
| lnc-TBC1D22A-4:12 | SEQ0739 | 0.03324 | 0.969 | 0.757 |
| lnc-TBC1D3H-1:1 | SEQ0334 | 0.01449 | 0.729 | 0.792 |

TABLE 5-continued

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| lnc-TBC1D3H-3:1 | SEQ0294 | 0.01209 | 0.72 | 0.799 |
| lnc-TBL1XR1-7:1 | SEQ0458 | 0.02049 | 0.754 | 0.778 |
| lnc-TCEANC2-3:1 | SEQ0106 | 0.00451 | 0.549 | 0.833 |
| lnc-TCEANC2-3:2 | SEQ0385 | 0.01727 | 1.882 | 0.215 |
| lnc-TCF19-1:80 | SEQ0740 | 0.03324 | 1.351 | 0.243 |
| lnc-TCF7-1:3 | SEQ0990 | 0.0449 | 0.866 | 0.743 |
| lnc-TCP10-2:1 | SEQ0991 | 0.0449 | 0.876 | 0.743 |
| lnc-TCP11-2:3 | SEQ0640 | 0.02842 | 0.67 | 0.764 |
| lnc-TCP11L2-1:4 | SEQ0741 | 0.03324 | 0.74 | 0.757 |
| lnc-TDO2-6:1 | SEQ0641 | 0.02842 | 0.758 | 0.764 |
| lnc-TDP2-1:1 | SEQ0335 | 0.01449 | 1.29 | 0.208 |
| lnc-TEAD4-1:1 | SEQ0992 | 0.0449 | 1.868 | 0.257 |
| lnc-TEFM-10:2 | SEQ0993 | 0.0449 | 0.736 | 0.743 |
| lnc-TEKT3-3:1 | SEQ0844 | 0.03872 | 0.744 | 0.75 |
| lnc-TEKT4-4:1 | SEQ0132 | 0.00556 | 1.332 | 0.174 |
| lnc-TENM3-3:3 | SEQ0001 | 0.00007 | 0.717 | 0.938 |
| lnc-TENM3-3:4 | SEQ0008 | 0.00037 | 1.947 | 0.097 |
| lnc-TENM3-3:5 | SEQ0009 | 0.00037 | 1.993 | 0.097 |
| lnc-TENM4-4:1 | SEQ0742 | 0.03324 | 2.209 | 0.243 |
| lnc-TEX10-1:1 | SEQ0459 | 0.02049 | 0.814 | 0.778 |
| lnc-TEX29-3:1 | SEQ0172 | 0.00681 | 0.767 | 0.819 |
| lnc-TEX49-4:1 | SEQ0994 | 0.0449 | 0.789 | 0.743 |
| lnc-TF-4:1 | SEQ0743 | 0.03324 | 0.898 | 0.757 |
| lnc-TFCP2L1-6:1 | SEQ0460 | 0.02049 | 0.743 | 0.778 |
| lnc-TGM6-2:1 | SEQ0216 | 0.00829 | 0.741 | 0.813 |
| lnc-THAP12-1:5 | SEQ0642 | 0.02842 | 1.427 | 0.236 |
| lnc-THOC5-3:1 | SEQ0133 | 0.00556 | 0.717 | 0.826 |
| lnc-THY1-3:1 | SEQ0995 | 0.0449 | 0.788 | 0.743 |
| lnc-THYN1-1:1 | SEQ0461 | 0.02049 | 1.173 | 0.222 |
| lnc-TLDC2-4:1 | SEQ0555 | 0.02418 | 1.214 | 0.229 |
| lnc-TLE4-7:1 | SEQ0255 | 0.01004 | 1.184 | 0.194 |
| lnc-TLK1-1:2 | SEQ0556 | 0.02418 | 0.76 | 0.771 |
| lnc-TLNRD1-3:1 | SEQ0462 | 0.02049 | 0.829 | 0.778 |
| lnc-TMEM126B-2:3 | SEQ0336 | 0.01449 | 0.508 | 0.792 |
| lnc-TMEM126B-2:4 | SEQ0643 | 0.02842 | 1.964 | 0.236 |
| lnc-TMEM132C-6:5 | SEQ0996 | 0.0449 | 1.222 | 0.257 |
| lnc-TMEM168-1:1 | SEQ0073 | 0.00291 | 0.761 | 0.847 |
| lnc-TMEM185B-12:1 | SEQ0173 | 0.00681 | 0.549 | 0.819 |
| lnc-TMEM185B-12:7 | SEQ0060 | 0.00232 | 1.694 | 0.146 |
| lnc-TMEM185B-2:3 | SEQ0386 | 0.01727 | 1.212 | 0.215 |
| lnc-TMEM211-2:8 | SEQ0644 | 0.02842 | 1.278 | 0.236 |
| lnc-TMEM242-6:1 | SEQ0463 | 0.02049 | 0.879 | 0.778 |
| lnc-TMEM248-4:11 | SEQ0845 | 0.03872 | 0.842 | 0.75 |
| lnc-TMEM70-7:1 | SEQ0217 | 0.00829 | 1.404 | 0.188 |
| lnc-TMX4-3:1 | SEQ0464 | 0.02049 | 0.776 | 0.778 |
| lnc-TNFRSF19-2:1 | SEQ0744 | 0.03324 | 1.177 | 0.243 |
| lnc-TNFSF4-3:3 | SEQ0337 | 0.01449 | 1.714 | 0.208 |
| lnc-TOGARAM2-1:5 | SEQ0645 | 0.02842 | 0.81 | 0.764 |
| lnc-TOGARAM2-1:6 | SEQ0646 | 0.02842 | 0.81 | 0.764 |
| lnc-TP53TG3-65:1 | SEQ0465 | 0.02049 | 1.227 | 0.222 |
| lnc-TP53TG3D-2:1 | SEQ0846 | 0.03872 | 0.9 | 0.75 |
| lnc-TP53TG3F-8:1 | SEQ0647 | 0.02842 | 1.33 | 0.236 |
| lnc-TPPP-1:2 | SEQ0002 | 0.00014 | 0.158 | 0.924 |
| lnc-TPPP-1:3 | SEQ0134 | 0.00556 | 1.834 | 0.174 |
| lnc-TRAM1-1:1 | SEQ0074 | 0.00291 | 0.59 | 0.847 |
| lnc-TRIB2-14:1 | SEQ0021 | 0.00066 | 0.788 | 0.889 |
| lnc-TRIM13-2:1 | SEQ0174 | 0.00681 | 0.739 | 0.819 |
| lnc-TRIM26-2:33 | SEQ0745 | 0.03324 | 0.782 | 0.757 |
| lnc-TRIM26-2:74 | SEQ0338 | 0.01449 | 1.231 | 0.208 |
| lnc-TRIM27-10:2 | SEQ0107 | 0.00451 | 1.227 | 0.167 |
| lnc-TRIM37-2:1 | SEQ0997 | 0.0449 | 1.221 | 0.257 |
| lnc-TRIM43B-1:2 | SEQ0387 | 0.01727 | 0.8 | 0.785 |
| lnc-TRIM49D1-4:1 | SEQ0175 | 0.00681 | 1.36 | 0.181 |
| lnc-TRIM77-7:1 | SEQ0847 | 0.03872 | 0.741 | 0.75 |
| lnc-TRIML2-11:1 | SEQ0557 | 0.02418 | 1.296 | 0.229 |
| lnc-TRMT11-4:1 | SEQ0218 | 0.00829 | 0.773 | 0.813 |
| lnc-TRPM1-3:1 | SEQ0388 | 0.01727 | 0.83 | 0.785 |
| lnc-TSC22D2-1:4 | SEQ0466 | 0.02049 | 0.633 | 0.778 |
| lnc-TSHB-2:3 | SEQ0295 | 0.01209 | 0.564 | 0.799 |
| lnc-TSHB-2:4 | SEQ0467 | 0.02049 | 1.766 | 0.222 |
| lnc-TSHB-2:5 | SEQ0468 | 0.02049 | 1.766 | 0.222 |
| lnc-TSHB-2:6 | SEQ0296 | 0.01209 | 0.564 | 0.799 |
| lnc-TSR3-1:2 | SEQ0339 | 0.01449 | 0.784 | 0.792 |
| lnc-TSTD2-4:3 | SEQ0848 | 0.03872 | 1.229 | 0.25 |
| lnc-TTC26-9:1 | SEQ0558 | 0.02418 | 0.686 | 0.771 |
| lnc-TTC38-7:1 | SEQ0849 | 0.03872 | 1.169 | 0.25 |
| lnc-TTF2-4:1 | SEQ0998 | 0.0449 | 0.848 | 0.743 |
| lnc-TUBA1C-1:12 | SEQ0999 | 0.0449 | 0.731 | 0.743 |
| lnc-TUBE1-6:1 | SEQ0850 | 0.03872 | 1.141 | 0.25 |
| lnc-TUBGCP3-11:1 | SEQ0469 | 0.02049 | 0.885 | 0.778 |
| lnc-TUSC5-3:1 | SEQ1000 | 0.0449 | 1.345 | 0.257 |
| lnc-TWSG1-2:1 | SEQ0047 | 0.00183 | 0.673 | 0.861 |
| lnc-UBE2QL1-4:1 | SEQ0648 | 0.02842 | 0.864 | 0.764 |
| lnc-UBE3C-10:1 | SEQ0075 | 0.00291 | 1.627 | 0.153 |
| lnc-UBLCP1-2:6 | SEQ0048 | 0.00183 | 0.755 | 0.861 |
| lnc-UCK1-2:1 | SEQ0851 | 0.03872 | 0.774 | 0.75 |
| lnc-UGCG-1:1 | SEQ0219 | 0.00829 | 0.802 | 0.813 |
| lnc-UGT1A8-3:1 | SEQ0649 | 0.02842 | 1.428 | 0.236 |
| lnc-UGT2B28-1:2 | SEQ1001 | 0.0449 | 0.818 | 0.743 |
| lnc-UGT2B28-2:1 | SEQ0559 | 0.02418 | 0.764 | 0.771 |
| lnc-UGT3A2-3:1 | SEQ0389 | 0.01727 | 0.855 | 0.785 |
| lnc-UNC93B1-1:5 | SEQ1002 | 0.0449 | 0.806 | 0.743 |
| lnc-UNCX-3:26 | SEQ0470 | 0.02049 | 0.493 | 0.778 |
| lnc-UPK3B-7:1 | SEQ0297 | 0.01209 | 0.607 | 0.799 |
| lnc-USP16-15:1 | SEQ0650 | 0.02842 | 0.811 | 0.764 |
| lnc-USP16-9:3 | SEQ0091 | 0.00364 | 0.834 | 0.84 |
| lnc-USP17L7-1:1 | SEQ0746 | 0.03324 | 1.48 | 0.243 |
| lnc-USP24-2:3 | SEQ0747 | 0.03324 | 0.694 | 0.757 |
| lnc-USP31-2:3 | SEQ0022 | 0.00066 | 0.685 | 0.889 |
| lnc-USP53-1:1 | SEQ0390 | 0.01727 | 0.824 | 0.785 |
| lnc-USP6NL-13:1 | SEQ0748 | 0.03324 | 1.209 | 0.243 |
| lnc-VGLL3-11:1 | SEQ0220 | 0.00829 | 0.81 | 0.813 |
| lnc-VPS8-2:4 | SEQ0852 | 0.03872 | 0.742 | 0.75 |
| lnc-VSTM2B-5:12 | SEQ0560 | 0.02418 | 0.771 | 0.771 |
| lnc-VWA5B1-2:1 | SEQ0391 | 0.01727 | 1.479 | 0.215 |
| lnc-WDR4-2:6 | SEQ1003 | 0.0449 | 0.929 | 0.743 |
| lnc-WDR63-6:2 | SEQ0471 | 0.02049 | 0.655 | 0.778 |
| lnc-WDR70-7:6 | SEQ1004 | 0.0449 | 0.929 | 0.743 |
| lnc-WDR7-11:1 | SEQ0749 | 0.03324 | 1.151 | 0.243 |
| lnc-WDYHV1-1:2 | SEQ0561 | 0.02418 | 0.912 | 0.771 |
| lnc-WISP1-17:2 | SEQ0135 | 0.00556 | 0.715 | 0.826 |
| lnc-WSB1-2:1 | SEQ0256 | 0.01004 | 1.293 | 0.194 |
| lnc-XCL2-4:1 | SEQ1005 | 0.0449 | 0.714 | 0.743 |
| lnc-XXYLT1-5:1 | SEQ0221 | 0.00829 | 0.681 | 0.813 |
| lnc-YPEL5-5:1 | SEQ0750 | 0.03324 | 1.357 | 0.243 |
| lnc-ZC3H12D-2:3 | SEQ0392 | 0.01727 | 0.831 | 0.785 |
| lnc-ZC3H15-2:1 | SEQ0012 | 0.0005 | 0.765 | 0.896 |
| lnc-ZFAT-1:3 | SEQ0562 | 0.02418 | 0.907 | 0.771 |
| lnc-ZFAT-1:8 | SEQ0393 | 0.01727 | 0.841 | 0.785 |
| lnc-ZFC3H1-16:2 | SEQ0651 | 0.02842 | 0.789 | 0.764 |
| lnc-ZFP57-15:1 | SEQ0177 | 0.00701 | 0.402 | 0.826 |
| lnc-ZFP90-3:6 | SEQ0563 | 0.02418 | 0.739 | 0.771 |
| lnc-ZMYM2-7:1 | SEQ0853 | 0.03872 | 1.335 | 0.25 |
| lnc-ZNF107-7:1 | SEQ0652 | 0.02842 | 0.735 | 0.764 |
| lnc-ZNF124-1:2 | SEQ0564 | 0.02418 | 0.827 | 0.771 |
| lnc-ZNF189-2:1 | SEQ0751 | 0.03324 | 0.903 | 0.757 |
| lnc-ZNF25-7:1 | SEQ0257 | 0.01004 | 1.37 | 0.194 |
| lnc-ZNF25-9:4 | SEQ0298 | 0.01209 | 0.663 | 0.799 |
| lnc-ZNF273-4:4 | SEQ0092 | 0.00364 | 0.742 | 0.84 |
| lnc-ZNF330-2:1 | SEQ0854 | 0.03872 | 0.833 | 0.75 |
| lnc-ZNF33A-14:1 | SEQ0049 | 0.00183 | 1.499 | 0.139 |
| lnc-ZNF33A-8:1 | SEQ1006 | 0.0449 | 1.115 | 0.257 |
| lnc-ZNF33B-3:11 | SEQ1007 | 0.0449 | 0.846 | 0.743 |
| lnc-ZNF33B-6:1 | SEQ0394 | 0.01727 | 2.524 | 0.215 |
| lnc-ZNF33B-6:3 | SEQ0299 | 0.01209 | 0.825 | 0.799 |
| lnc-ZNF385C-4:1 | SEQ0472 | 0.02049 | 1.311 | 0.222 |
| lnc-ZNF423-3:3 | SEQ1008 | 0.0449 | 1.258 | 0.257 |
| lnc-ZNF430-3:1 | SEQ0855 | 0.03872 | 0.797 | 0.75 |
| lnc-ZNF430-3:4 | SEQ0258 | 0.01004 | 0.788 | 0.806 |
| lnc-ZNF442-1:2 | SEQ0061 | 0.00232 | 0.683 | 0.854 |
| lnc-ZNF460-2:1 | SEQ0473 | 0.02049 | 0.842 | 0.778 |
| lnc-ZNF506-5:2 | SEQ0108 | 0.00451 | 0.684 | 0.833 |
| lnc-ZNF544-2:1 | SEQ0474 | 0.02049 | 0.805 | 0.778 |
| lnc-ZNF573-2:2 | SEQ0856 | 0.03872 | 0.823 | 0.75 |
| lnc-ZNF624-4:3 | SEQ0395 | 0.01727 | 1.241 | 0.215 |
| lnc-ZNF654-3:1 | SEQ0857 | 0.03872 | 0.869 | 0.75 |
| lnc-ZNF720-5:3 | SEQ0222 | 0.00829 | 1.313 | 0.188 |
| lnc-ZNF724-6:1 | SEQ0176 | 0.00681 | 0.729 | 0.819 |

TABLE 5-continued

The Sequence number, p value, mean +/− SD, fold change and AUC of the 1008 lncRNAs with differential expression in AD group versus healthy control group (p value < 0.05, Wilcoxon test)

| lncRNA | SEQ | p value | Fold change | AUC |
|---|---|---|---|---|
| lnc-ZNF726-1:3 | SEQ0259 | 0.01004 | 2.115 | 0.194 |
| lnc-ZNF827-2:1 | SEQ0653 | 0.02842 | 0.924 | 0.764 |
| lnc-ZNF99-3:2 | SEQ0396 | 0.01727 | 0.751 | 0.785 |
| lnc-ZRANB2-2:1 | SEQ0654 | 0.02842 | 0.801 | 0.764 |
| lnc-ZSWIM2-15:1 | SEQ0655 | 0.02842 | 0.696 | 0.764 |
| lnc-ZWINT-2:4 | SEQ0565 | 0.02418 | 0.637 | 0.771 |
| LRP4-AS1:5 | SEQ0766 | 0.03872 | 1.288 | 0.25 |
| LYRM4-AS1:17 | SEQ0485 | 0.02418 | 0.893 | 0.771 |
| MAPT-AS1:1 | SEQ0767 | 0.03872 | 0.785 | 0.75 |
| MCPH1-AS1:2 | SEQ0308 | 0.01449 | 1.321 | 0.208 |
| MDC1-AS1:5 | SEQ0486 | 0.02418 | 1.248 | 0.229 |
| MEF2C-AS1:25 | SEQ0582 | 0.02842 | 0.907 | 0.764 |
| MIR155HG:7 | SEQ0876 | 0.0449 | 0.606 | 0.743 |
| MIR29B2CHG:33 | SEQ0583 | 0.02842 | 0.624 | 0.764 |
| MIR29B2CHG:46 | SEQ0181 | 0.00829 | 1.522 | 0.188 |
| MIR31HG:9 | SEQ0768 | 0.03872 | 0.835 | 0.75 |
| MIR4290HG:1 | SEQ0405 | 0.02049 | 0.773 | 0.778 |
| MIR9-3HG:29 | SEQ0769 | 0.03872 | 0.557 | 0.75 |
| MIR99AHG:104 | SEQ0096 | 0.00451 | 0.871 | 0.833 |
| MIR99AHG:37 | SEQ0584 | 0.02842 | 0.879 | 0.764 |
| MIR99AHG:46 | SEQ0877 | 0.0449 | 2.516 | 0.257 |
| NAV2-AS5:1 | SEQ0051 | 0.00232 | 1.302 | 0.146 |
| NAV2-AS5:2 | SEQ0052 | 0.00232 | 1.302 | 0.146 |
| NBAT1:11 | SEQ0347 | 0.01727 | 1.738 | 0.215 |
| NIFK-AS1:25 | SEQ0487 | 0.02418 | 0.846 | 0.771 |
| NUTM2A-AS1:49 | SEQ0182 | 0.00829 | 0.633 | 0.813 |
| NUTM2B-AS1:40 | SEQ0348 | 0.01727 | 0.74 | 0.785 |
| NUTM2B-AS1:53 | SEQ0004 | 0.00027 | 0.655 | 0.91 |
| PACRG-AS3:1 | SEQ0666 | 0.03324 | 1.162 | 0.243 |
| PCBP1-AS1:250 | SEQ0770 | 0.03872 | 1.266 | 0.25 |
| PITRM1-AS1:10 | SEQ0488 | 0.02418 | 1.274 | 0.229 |
| PTPRG-AS1:14 | SEQ0183 | 0.00829 | 0.625 | 0.813 |
| PURPL:13 | SEQ0585 | 0.02842 | 1.386 | 0.236 |
| RAPGEF4-AS1:1 | SEQ0878 | 0.0449 | 0.824 | 0.743 |
| RFX3-AS1:22 | SEQ0586 | 0.02842 | 0.819 | 0.764 |
| RORB-AS1:6 | SEQ0116 | 0.00556 | 0.845 | 0.826 |
| SCHLAP1:9 | SEQ0144 | 0.00681 | 0.8 | 0.819 |
| SEC24B-AS1:19 | SEQ0406 | 0.02049 | 1.852 | 0.222 |
| SLC16A12-AS1:1 | SEQ0771 | 0.03872 | 0.773 | 0.75 |
| SMILR:3 | SEQ0040 | 0.00183 | 1.306 | 0.139 |
| SNCA-AS1:3 | SEQ0041 | 0.00183 | 0.777 | 0.861 |
| SPATA41:13 | SEQ0879 | 0.0449 | 1.607 | 0.257 |
| SRGAP3-AS2:10 | SEQ0349 | 0.01727 | 0.674 | 0.785 |
| SUCLG2-AS1:14 | SEQ0489 | 0.02418 | 0.92 | 0.771 |
| SUCLG2-AS1:9 | SEQ0490 | 0.02418 | 0.92 | 0.771 |
| TCL6:24 | SEQ0066 | 0.00291 | 1.448 | 0.153 |
| TM4SF19-AS1:10 | SEQ0184 | 0.00829 | 1.84 | 0.188 |
| TM4SF19-AS1:15 | SEQ0491 | 0.02418 | 0.853 | 0.771 |
| TMEM9B-AS1:11 | SEQ0185 | 0.00829 | 3.049 | 0.188 |
| TPT1-AS1:26 | SEQ0186 | 0.00829 | 0.763 | 0.813 |
| TRIM52-AS1:24 | SEQ0492 | 0.02418 | 1.183 | 0.229 |
| TRIM52-AS1:8 | SEQ0587 | 0.02842 | 1.272 | 0.236 |
| TTN-AS1:79 | SEQ0187 | 0.00829 | 0.829 | 0.813 |
| TTN-AS1:80 | SEQ0188 | 0.00829 | 0.829 | 0.813 |
| UCA1:7 | SEQ0078 | 0.00364 | 0.697 | 0.84 |
| UGDH-AS1:10 | SEQ0407 | 0.02049 | 0.541 | 0.778 |
| WDR86-AS1:15 | SEQ0588 | 0.02842 | 1.212 | 0.236 |
| WEE2-AS1:23 | SEQ0408 | 0.02049 | 0.704 | 0.778 |
| WT1-AS:9 | SEQ0117 | 0.00556 | 0.542 | 0.826 |
| YEATS2-AS1:3 | SEQ0772 | 0.03872 | 0.806 | 0.75 |
| ZNF528-AS1:1 | SEQ0773 | 0.03872 | 0.636 | 0.75 |
| ZNF529-AS1:21 | SEQ0880 | 0.0449 | 0.819 | 0.743 |

Out of the 1008 lncRNAs differentially expressed with a statistical significance (p value <0.05), 33 lncRNAs showed a fold change of >2 or <0.5 and are shown in the Table 6.

TABLE 6

Mean +/− SD of the 33 lncRNAs that shows a differential expression with both a statistically significance (p < 0.05, Wilcoxon test) and a fold change >2 or <0.5

| lncRNA | p value | Fold change | lncRNA | p value | Fold change |
|---|---|---|---|---|---|
| lnc-QRFP-5:1 | 0.00066 | 2.170 | MIR99AHG:46 | 0.04490 | 2.516 |
| lnc-C21orf58-1:2 | 0.00143 | 2.231 | lnc-CPM-2:11 | 0.04490 | 0.424 |
| ARRDC3-AS1:7 | 0.00232 | 0.441 | lnc-ERFE-1:1 | 0.04490 | 0.489 |
| lnc-CRYBB1-1:1 | 0.00232 | 0.487 | lnc-LRRC3B-1:3 | 0.04490 | 0.463 |
| lnc-LIMS3-1:10 | 0.00364 | 2.270 | LINC02177:8 | 0.03872 | 0.494 |
| lnc-MARCH4-2:7 | 0.00364 | 2.000 | lnc-KLF11-1:8 | 0.03324 | 0.286 |
| lnc-SUGT1-3:1 | 0.00556 | 2.047 | lnc-SNCA-3:1 | 0.02418 | 0.498 |
| DARS-AS1:47 | 0.00829 | 2.015 | lnc-UNCX-3:26 | 0.02049 | 0.493 |
| TMEM9B-AS1:11 | 0.00829 | 3.049 | BLACAT1:5 | 0.01727 | 0.424 |
| lnc-ZNF726-1:3 | 0.01004 | 2.115 | lnc-CHD1L-5:13 | 0.01449 | 0.370 |
| lnc-SLC39A11-10:11 | 0.01209 | 4.380 | lnc-EDDM13-5:11 | 0.01004 | 0.372 |
| lnc-PSMB1-6:4 | 0.01449 | 2.134 | lnc-EEF1AKMT1-3:6 | 0.00829 | 0.423 |
| DPH6-AS1:3 | 0.01727 | 2.004 | FLVCR1-AS1:13 | 0.00681 | 0.413 |
| lnc-ZNF33B-6:1 | 0.01727 | 2.524 | lnc-NAXD-6:5 | 0.00556 | 0.479 |
| lnc-PAPPA-1:3 | 0.03324 | 2.192 | lnc-ZFP57-15:1 | 0.00701 | 0.402 |
| lnc-TENM4-4:1 | 0.03324 | 2.209 | lnc-TPPP-1:2 | 0.00014 | 0.158 |
| lnc-IQCF6-2:3 | 0.03872 | 2.026 | | | |

Out of the 1008 lncRNAs differentially expressed with a statistical significance (p value <0.05), 60 lncRNAs showed an AUC of ≥0.85 and are shown in Table 7.

TABLE 7

60 lncRNAs with a p value < 0.05 and an individual AUC value AUC ≥0.85

| lncRNA | AUC |
| --- | --- |
| ARRDC3-AS1:7 | 0.854 |
| HAND2-AS1:70 | 0.861 |
| LINC00882:70 | 0.875 |
| LINC00882:71 | 0.875 |
| LINC01410:11 | 0.882 |
| LINC02345:11 | 0.111 |
| NAV2-AS5:1 | 0.146 |
| NAV2-AS5:2 | 0.146 |
| NUTM2B-AS1:53 | 0.910 |
| SMILR:3 | 0.139 |
| SNCA-AS1:3 | 0.861 |
| lnc-ABCA5-7:1 | 0.111 |
| lnc-ACOT12-9:1 | 0.854 |
| lnc-APLP2-4:1 | 0.854 |
| lnc-C21orf58-1:2 | 0.132 |
| lnc-CEP170-9:2 | 0.861 |
| lnc-CNDP1-7:1 | 0.882 |
| lnc-CRYBB1-1:1 | 0.854 |
| lnc-CSNK1A1-6:1 | 0.875 |
| lnc-DAZAP2-3:1 | 0.854 |
| lnc-DKK1-5:3 | 0.910 |
| lnc-DLG5-1:1 | 0.868 |
| lnc-DOCK7-7:1 | 0.889 |
| lnc-DUSP10-6:1 | 0.854 |
| lnc-DUSP26-3:2 | 0.875 |
| lnc-EBLN1-1:4 | 0.889 |
| lnc-EDDM13-5:3 | 0.132 |
| lnc-FAM133B-2:1 | 0.868 |
| lnc-FAM217A-1:2 | 0.875 |
| lnc-FAM49B-8:1 | 0.104 |
| lnc-FAT1-7:2 | 0.111 |
| lnc-FILIP1L-3:1 | 0.854 |
| lnc-FNBP1L-1:11 | 0.910 |
| lnc-GHR-1:1 | 0.917 |
| lnc-HECA-6:1 | 0.903 |
| lnc-IRS1-6:1 | 0.868 |
| lnc-LEPROTL1-12:1 | 0.896 |
| lnc-MGST3-1:3 | 0.139 |
| lnc-NCR3LG1-3:1 | 0.889 |
| lnc-OR4F29-3:11 | 0.861 |
| lnc-PPP2R3C-4:1 | 0.882 |
| lnc-QRFP-5:1 | 0.111 |
| lnc-RHNO1-1:1 | 0.118 |
| lnc-RNF6-2:1 | 0.854 |
| lnc-RPS21-4:2 | 0.882 |
| lnc-SOX14-2:1 | 0.861 |
| lnc-SPP1-1:1 | 0.861 |
| lnc-STOML3-6:1 | 0.868 |
| lnc-TACSTD2-2:4 | 0.889 |
| lnc-TENM3-3:3 | 0.938 |
| lnc-TENM3-3:4 | 0.097 |
| lnc-TENM3-3:5 | 0.097 |
| lnc-TMEM185B-12:7 | 0.146 |
| lnc-TPPP-1:2 | 0.924 |
| lnc-TRIB2-14:1 | 0.889 |
| lnc-TWSG1-2:1 | 0.861 |
| lnc-UBLCP1-2:6 | 0.861 |
| lnc-USP31-2:3 | 0.889 |
| lnc-ZC3H15-2:1 | 0.896 |
| lnc-ZNF33A-14:1 | 0.139 |
| lnc-ZNF442-1:2 | 0.854 |

The results from the predictive modelling based on the random forest algorithm to discriminate between AD patient and healthy control populations when using the selected miRNAs with a p value <0.05 comprising signatures of 2 or more miRNAs showed a good accuracy. For example, the signature comprising three miRNAs, miR1220.3p, miR378d and miR99a.5p, enabled a good AUC of 0.839 and an accuracy of 81.8%.

The predictive modelling based on the random forest algorithm to discriminate between AD patient and healthy control populations when using the total of the 19867 lncRNAs analyzed, enabled to show that the AUC in function of the number of lncRNA reached a plateau with the following 13 lncRNAs. These 13 lncRNAs were used to construct the model. The results show that this lncRNA signature enabled a discrimination between the 2 populations (mild AD patient and healthy control populations) with an AUC value=0.993, an accuracy=95.8%, sensitivity=100% and specificity=91.7%.

| lncRNA | Rank |
| --- | --- |
| lnc-DLG5-1:1 | 1 |
| lnc-EBLN1-1:4 | 2 |
| lnc-FAT1-7:2 | 3 |
| lnc-PRR5-5:1 | 4 |
| lnc-RBKS-6:1 | 5 |
| lnc-FOXD4L5-35:1 | 6 |
| lnc-TENM3-3:3 | 7 |
| lnc-FAM133B-2:1 | 8 |
| lnc-ZNF726-1:3 | 9 |
| lnc-AP3M1-1:1 | 10 |
| lnc-DUSP10-6:1 | 11 |
| lnc-TPPP-1:2 | 12 |
| LINC01206:20 | 13 |

Out of the 1008 lncRNAs differentially expressed with a statistical significance (p value <0.05), the 90 lncRNAs with a fold change of >2 (or <0.5) or an AUC of ≥0.85 (or ≤0.15) were used for the predictive modelling based on the random forest algorithm. The results show that with the following 7 top ranked candidates enabled a full discrimination between AD and HV groups, with an AUC value of 100% as well as 100% accuracy, 100% sensitivity and 100% specificity.

| lncRNA | Rank |
| --- | --- |
| LINC02345:11 | 1 |
| lnc-EBLN1-1:4 | 2 |
| lnc-TPPP-1:2 | 3 |
| lnc-TENM3-3:3 | 4 |
| lnc-FAT1-7:2 | 5 |
| lnc-DKK1-5:3 | 6 |
| lnc-TACSTD2-2:4 | 7 |

When applying another filter considering a list of the lncRNAs which have a fold change of >1.6 and an AUC of ≥0.85, the use of random forest algorithm enabled to select the following 12-top ranked lncRNAs to construct the model and this enabled to discriminate between the AD and HV populations with still an excellent AUC=0.979, excellent accuracy of 95.8% sensitivity of 91.7% and specificity of 100%.

| lncRNA | Rank |
| --- | --- |
| lnc-TPPP-1:2 | 1 |
| ARRDC3-AS1:7 | 2 |
| lnc-TENM3-3:5 | 3 |
| lnc-TENM3-3:4 | 4 |
| lnc-QRFP-5:1 | 5 |

-continued

| lncRNA | Rank |
| --- | --- |
| lnc-CRYBB1-1:1 | 6 |
| lnc-MGST3-1:3 | 7 |
| lnc-FAM49B-8:1 | 8 |
| HAND2-AS1:70 | 9 |
| lnc-TMEM185B-12:7 | 10 |
| lnc-CNDP1-7:1 | 11 |
| lnc-C21orf58-1:2 | 12 |

Further to select the best lncRNA candidates, modeling using Random Forest algorithm was applied to a specific set of lncRNA candidates having both a statistically significant differential expression in AD patients versus healthy control populations and a good correlation (Pearson R coefficient) with scores of neurocognitive tests including MMSE and/or MOCA out of 7 neuropsychological tests performed (Table 8): The results show that the signature of the following 3 top ranked lncRNAs enabled an excellent discrimination between AD patients and healthy control populations with AUC=0.953, accuracy, sensitivity and specificity of 91.7%, 91.7% and 91.7%.

| lncRNA | Rank |
| --- | --- |
| lnc-TENM3-3:3 | 1 |
| lnc-MARCH4-2:7 | 2 |
| lnc-LRRC1-5:2 | 3 |

Modeling using Random Forest algorithm was also applied to a specific set of lncRNA candidates from Table 9 having both a statistically significant differential expression in AD patients versus healthy control populations and a good correlation (Pearson) with neuroimaging scores (volume of brain structures of relevance for cognition and memory such as the mediotemporal area, left and right hippocampus, left and right amygdala, entorhinal cortex out of more than 120 structures measured): The results show that the signature of the following 7 top ranked lncRNAs enabled an excellent discrimination between AD patients and healthy control population with AUC=0.993, accuracy=95.8%, sensitivity=91.7% and specificity=100%.

| lncRNA | Rank |
| --- | --- |
| lnc-TPPP-1:2 | 1 |
| lnc-TENM3-3:3 | 2 |
| lnc-TMEM185B-12:7 | 3 |
| lnc-NAXD-6:5 | 4 |
| lnc-HECA-6:1 | 5 |
| lnc-COMMD6-10:1 | 6 |
| MIR29B2CHG:46 | 7 |

TABLE 8 lncRNAs of the present invention that correlate with neurocognitive tests, MoCA, MMSE. R: correlation coefficient (Pearson). HV: healthy control group, AD: mild to moderate AD group

| Cognitive test | lncRNA | R_HV + AD | R_HV | R_AD | p value | AUC |
| --- | --- | --- | --- | --- | --- | --- |
| MoCA | LINC00839:18 | −0.80 | 0.29 | −0.78 | 0.00556 | 0.83 |
| MoCA | LINC01087:1 | −0.74 | −0.13 | −0.89 | 0.00681 | 0.82 |
| MMSE | LINC01087:1 | −0.68 | 0.05 | −0.75 | 0.00681 | 0.82 |
| MMSE | lnc-ANAPC11-2:6 | 0.65 | 0.26 | 0.77 | 0.04490 | 0.26 |
| MoCA | lnc-ANAPC11-2:6 | 0.59 | −0.46 | 0.77 | 0.04490 | 0.26 |
| MoCA | lnc-ARHGAP26-4:33 | −0.64 | −0.66 | −0.72 | 0.03872 | 0.75 |
| MoCA | lnc-CCDC197-2:1 | −0.14 | −0.42 | 0.74 | 0.00291 | 0.85 |
| MMSE | lnc-CFAP36-3:2 | −0.62 | 0.05 | −0.75 | 0.03872 | 0.75 |
| MoCA | lnc-DHX38-25:1 | −0.69 | −0.60 | −0.77 | 0.01004 | 0.81 |
| MMSE | lnc-DHX38-25:1 | −0.65 | −0.57 | −0.71 | 0.01004 | 0.81 |
| MoCA | lnc-EZH2-3:1 | −0.69 | 0.18 | −0.78 | 0.01209 | 0.80 |
| MMSE | lnc-GNG5-8:1 | −0.72 | 0.32 | −0.71 | 0.03324 | 0.76 |
| MoCA | lnc-GPRC5A-4:1 | −0.65 | −0.02 | −0.74 | 0.02842 | 0.76 |
| MMSE | lnc-GRAMD2B-4:1 | −0.59 | 0.42 | −0.72 | 0.03872 | 0.75 |
| MMSE | lnc-GRIP1-8:1 | −0.03 | 0.30 | −0.73 | 0.03872 | 0.25 |
| MoCA | lnc-LYN-8:1 | 0.13 | 0.54 | −0.71 | 0.02842 | 0.24 |
| MMSE | lnc-MAP9-6:1 | −0.73 | −0.08 | −0.74 | 0.01209 | 0.80 |
| MMSE | lnc-NRP1-4:1 | −0.11 | 0.27 | −0.72 | 0.04490 | 0.26 |
| MoCA | lnc-RBFOX1-2:1 | 0.02 | 0.13 | −0.75 | 0.01727 | 0.22 |
| MoCA | lnc-RPL37-2:1 | 0.62 | −0.16 | 0.75 | 0.00829 | 0.19 |
| MMSE | lnc-RUBCN-1:1 | 0.11 | 0.33 | 0.72 | 0.03872 | 0.75 |
| MMSE | lnc-SNCA-3:1 | 0.08 | 0.12 | 0.76 | 0.02418 | 0.77 |
| MMSE | lnc-SRSF2-2:5 | 0.10 | 0.04 | 0.75 | 0.03324 | 0.76 |
| MoCA | lnc-SRSF2-2:5 | −0.05 | −0.32 | 0.73 | 0.03324 | 0.76 |
| MMSE | lnc-TMEM185B-12:7 | 0.06 | −0.14 | −0.73 | 0.00232 | 0.15 |
| MoCA | lnc-TRIB2-14:1 | −0.76 | −0.45 | −0.71 | 0.00066 | 0.89 |
| MMSE | lnc-TRIM43B-1:2 | −0.74 | −0.11 | −0.76 | 0.01727 | 0.78 |
| MoCA | lnc-TRIM43B-1:2 | −0.72 | −0.12 | −0.74 | 0.01727 | 0.78 |
| MMSE | lnc-ZNF189-2:1 | −0.70 | −0.35 | −0.74 | 0.03324 | 0.76 |
| MoCA | lnc-ZNF189-2:1 | −0.67 | 0.03 | −0.76 | 0.03324 | 0.76 |
| MMSE | lnc-ZRANB2-2:1 | −0.65 | −0.36 | −0.82 | 0.02842 | 0.76 |
| MoCA | lnc-ZRANB2-2:1 | −0.59 | 0.16 | −0.80 | 0.02842 | 0.76 |

TABLE 9 lncRNAs of the present invention that correlate with MRI (volumes
of the brain structures). R: correlation coefficient (Pearson).
HV: healthy control group, AD: mild to moderate AD group.

| MRI | lncRNA | R_HV + AD | R_HV | R_AD | p value | AUC |
|---|---|---|---|---|---|---|
| Left.Amygdala | CYTOR:18 | 0.71 | 0.30 | 0.69 | 0.00291 | 0.15 |
| Left.Hippocampus | DLGAP2-AS1:18 | −0.71 | −0.51 | −0.76 | 0.03324 | 0.76 |
| Left.Hippocampus | LINC00458:19 | −0.79 | −0.48 | −0.78 | 0.02842 | 0.76 |
| Mediotemporal | LINC00458:19 | −0.72 | −0.48 | −0.53 | 0.02842 | 0.76 |
| Left.Hippocampus | LINC00938:6 | −0.82 | −0.48 | −0.76 | 0.01209 | 0.80 |
| Mediotemporal | LINC00938:6 | −0.76 | −0.63 | −0.46 | 0.01209 | 0.80 |
| Right.Hippocampus | LINC00938:6 | −0.75 | −0.56 | −0.48 | 0.01209 | 0.80 |
| Left.Amygdala | LINC01629:11 | −0.78 | −0.53 | −0.83 | 0.02842 | 0.76 |
| Left.Hippocampus | lnc-AIG1-5:1 | −0.78 | −0.64 | −0.73 | 0.02418 | 0.77 |
| Left.Hippocampus | lnc-AKR1D1-5:2 | −0.74 | −0.47 | −0.69 | 0.00451 | 0.83 |
| Right.Hippocampus | lnc-AKR1D1-5:2 | −0.71 | −0.27 | −0.73 | 0.00451 | 0.83 |
| Mediotemporal | lnc-AKR1D1-5:2 | −0.71 | −0.26 | −0.72 | 0.00451 | 0.83 |
| Right.Amygdala | lnc-C3orf58-7:1 | −0.73 | −0.22 | −0.69 | 0.02842 | 0.76 |
| Left.Hippocampus | lnc-C5orf30-10:2 | −0.73 | −0.58 | −0.58 | 0.02842 | 0.76 |
| Right.Amygdala | lnc-CASP9-1:1 | 0.73 | 0.26 | 0.81 | 0.03872 | 0.25 |
| Right.Hippocampus | lnc-CHN1-5:11 | −0.72 | −0.44 | −0.67 | 0.02049 | 0.78 |
| Right.Amygdala | lnc-CLVS2-2:5 | −0.74 | −0.39 | −0.75 | 0.01727 | 0.78 |
| Left.Hippocampus | lnc-DAZAP2-3:1 | −0.72 | −0.53 | −0.58 | 0.00232 | 0.85 |
| Mediotemporal | lnc-DTWD2-14:1 | −0.75 | −0.49 | −0.79 | 0.01727 | 0.78 |
| Left.Amygdala | lnc-DTWD2-14:1 | −0.74 | −0.46 | −0.82 | 0.01727 | 0.78 |
| lh_entorhinal | lnc-DTWD2-14:1 | −0.74 | −0.59 | −0.61 | 0.01727 | 0.78 |
| Right.Hippocampus | lnc-ELFN2-1:3 | −0.77 | −0.26 | −0.76 | 0.00364 | 0.84 |
| Left.Amygdala | lnc-ELFN2-1:3 | −0.74 | −0.27 | −0.81 | 0.00364 | 0.84 |
| Mediotemporal | lnc-ELFN2-1:3 | −0.74 | −0.22 | −0.73 | 0.00364 | 0.84 |
| Right.Amygdala | lnc-ELFN2-1:3 | −0.74 | −0.37 | −0.61 | 0.00364 | 0.84 |
| Left.Hippocampus | lnc-FAM171B-1:6 | −0.72 | −0.28 | −0.62 | 0.00829 | 0.81 |
| Left.Hippocampus | lnc-FGD4-8:1 | −0.74 | −0.49 | −0.61 | 0.01004 | 0.81 |
| Left.Amygdala | lnc-FGD4-9:1 | −0.76 | −0.49 | −0.56 | 0.00364 | 0.84 |
| Right.Hippocampus | lnc-FGD4-9:1 | −0.74 | −0.19 | −0.64 | 0.00364 | 0.84 |
| Mediotemporal | lnc-FGD4-9:1 | −0.72 | −0.28 | −0.54 | 0.00364 | 0.84 |
| Left.Hippocampus | lnc-FGD4-9:1 | −0.71 | −0.33 | −0.52 | 0.00364 | 0.84 |
| lh_entorhinal | lnc-GPR39-10:2 | 0.77 | 0.68 | 0.49 | 0.00681 | 0.18 |
| Left.Amygdala | lnc-GPR39-10:2 | 0.72 | 0.54 | 0.37 | 0.00681 | 0.18 |
| Left.Hippocampus | lnc-GRM1-1:31 | −0.76 | −0.39 | −0.72 | 0.00681 | 0.82 |
| Right.Hippocampus | lnc-GRM1-1:31 | −0.71 | −0.38 | −0.56 | 0.00681 | 0.82 |
| Left.Hippocampus | lnc-GRM1-1:32 | −0.76 | −0.39 | −0.72 | 0.00681 | 0.82 |
| Right.Hippocampus | lnc-GRM1-1:32 | −0.71 | −0.38 | −0.56 | 0.00681 | 0.82 |
| Right.Hippocampus | lnc-HECA-3:13 | −0.72 | −0.31 | −0.67 | 0.01004 | 0.81 |
| Right.Amygdala | lnc-HJURP-7:1 | −0.77 | −0.46 | −0.77 | 0.02049 | 0.78 |
| Left.Hippocampus | lnc-HJURP-7:1 | −0.73 | −0.33 | −0.73 | 0.02049 | 0.78 |
| Right.Hippocampus | lnc-HJURP-7:1 | −0.73 | −0.02 | −0.93 | 0.02049 | 0.78 |
| Mediotemporal | lnc-HJURP-7:1 | −0.72 | −0.20 | −0.82 | 0.02049 | 0.78 |
| Left.Amygdala | lnc-IRS1-6:1 | −0.75 | −0.35 | −0.72 | 0.00143 | 0.87 |
| Right.Hippocampus | lnc-IRS1-6:1 | −0.73 | −0.36 | −0.56 | 0.00143 | 0.87 |
| Mediotemporal | lnc-IRS1-6:1 | −0.71 | −0.34 | −0.51 | 0.00143 | 0.87 |
| Right.Hippocampus | lnc-KDM3A-1:4 | −0.81 | −0.35 | −0.80 | 0.00451 | 0.83 |
| Mediotemporal | lnc-KDM3A-1:4 | −0.77 | −0.36 | −0.70 | 0.00451 | 0.83 |
| Left.Hippocampus | lnc-KDM3A-1:4 | −0.72 | −0.26 | −0.61 | 0.00451 | 0.83 |
| Left.Hippocampus | lnc-LARP1B-1:15 | −0.75 | −0.56 | −0.75 | 0.01209 | 0.80 |
| Right.Amygdala | lnc-LARP1B-1:15 | −0.75 | −0.63 | −0.71 | 0.01209 | 0.80 |
| Left.Hippocampus | lnc-LARP1B-1:17 | −0.75 | −0.56 | −0.75 | 0.01209 | 0.80 |
| Right.Amygdala | lnc-LARP1B-1:17 | −0.75 | −0.63 | −0.71 | 0.01209 | 0.80 |
| Right.Amygdala | lnc-MAMDC2-1:1 | −0.75 | −0.72 | −0.70 | 0.02418 | 0.77 |
| Left.Hippocampus | lnc-MAP9-6:1 | −0.79 | −0.43 | −0.87 | 0.01209 | 0.80 |
| Right.Hippocampus | lnc-NAALADL2-8:1 | −0.71 | −0.28 | −0.72 | 0.01449 | 0.79 |
| Right.Hippocampus | lnc-NBPF14-1:2 | −0.80 | −0.38 | −0.82 | 0.00364 | 0.84 |
| Mediotemporal | lnc-NBPF14-1:2 | −0.75 | −0.37 | −0.67 | 0.00364 | 0.84 |
| Right.Amygdala | lnc-NBPF14-1:2 | −0.73 | −0.40 | −0.60 | 0.00364 | 0.84 |
| Left.Hippocampus | lnc-NBPF14-1:2 | −0.72 | −0.48 | −0.52 | 0.00364 | 0.84 |
| Right.Hippocampus | lnc-PIGB-1:5 | −0.73 | −0.26 | −0.79 | 0.02418 | 0.77 |
| Right.Amygdala | lnc-PLN-2:1 | −0.77 | −0.66 | −0.72 | 0.03324 | 0.76 |
| Mediotemporal | lnc-PLN-2:1 | −0.76 | −0.66 | −0.67 | 0.03324 | 0.76 |
| Left.Hippocampus | lnc-PLN-2:1 | −0.75 | −0.67 | −0.64 | 0.03324 | 0.76 |
| Right.Hippocampus | lnc-PLN-2:1 | −0.73 | −0.54 | −0.68 | 0.03324 | 0.76 |
| Left.Hippocampus | lnc-PTPN4-1:1 | −0.74 | −0.59 | −0.69 | 0.02842 | 0.76 |
| Right.Amygdala | lnc-SLC38A2-1:11 | −0.76 | −0.73 | −0.57 | 0.01004 | 0.81 |
| Left.Amygdala | lnc-SLC38A2-1:11 | −0.73 | −0.57 | −0.38 | 0.01004 | 0.81 |
| Right.Amygdala | lnc-SMARCA5-4:18 | −0.72 | −0.35 | −0.78 | 0.01004 | 0.81 |
| Mediotemporal | lnc-SMARCA5-4:18 | −0.72 | −0.29 | −0.84 | 0.01004 | 0.81 |
| Left.Amygdala | lnc-SMARCA5-4:18 | −0.71 | −0.30 | −0.92 | 0.01004 | 0.81 |
| lh_entorhinal | lnc-TMEM242-6:1 | −0.77 | −0.64 | −0.78 | 0.02049 | 0.78 |
| Mediotemporal | lnc-TMEM242-6:1 | −0.72 | −0.62 | −0.63 | 0.02049 | 0.78 |
| Right.Hippocampus | lnc-TPPP-1:2 | −0.73 | −0.03 | −0.42 | 0.00014 | 0.92 |
| Left.Hippocampus | lnc-TRIM43B-1:2 | −0.75 | −0.47 | −0.72 | 0.01727 | 0.78 |

TABLE 9-continued lncRNAs of the present invention that correlate with MRI (volumes of the brain structures). R: correlation coefficient (Pearson). HV: healthy control group, AD: mild to moderate AD group.

| MRI | lncRNA | R_HV + AD | R_HV | R_AD | p value | AUC |
|---|---|---|---|---|---|---|
| lh_entorhinal | lnc-TRMT11-4:1 | −0.80 | −0.86 | −0.30 | 0.00829 | 0.81 |
| Mediotemporal | lnc-TRMT11-4:1 | −0.74 | −0.73 | −0.30 | 0.00829 | 0.81 |
| Left.Amygdala | lnc-TRMT11-4:1 | −0.73 | −0.58 | −0.35 | 0.00829 | 0.81 |
| Left.Hippocampus | lnc-USP53-1:1 | −0.75 | −0.24 | −0.84 | 0.01727 | 0.78 |
| Left.Hippocampus | lnc-ZNF33B-6:3 | −0.78 | −0.40 | −0.81 | 0.01209 | 0.80 |
| Right.Amygdala | lnc-ZNF33B-6:3 | −0.74 | −0.47 | −0.65 | 0.01209 | 0.80 |
| Right.Amygdala | MIR29B2CHG:46 | 0.74 | 0.35 | 0.82 | 0.00829 | 0.19 |
| rh_entorhinal | MIR29B2CHG:46 | 0.71 | 0.45 | 0.80 | 0.00829 | 0.19 |
| Right.Amygdala | PCBP1-AS1:250 | 0.73 | 0.20 | 0.71 | 0.03872 | 0.25 |
| Mediotemporal | PCBP1-AS1:250 | 0.71 | 0.19 | 0.70 | 0.03872 | 0.25 |

Modeling using Random Forest algorithm was also applied to a specific set of lncRNA candidates from Table 10 having both a statistically significant differential expression in AD patients versus healthy control populations and a good correlation (Pearson) with level of the CSF biomarkers of high relevance to AD pathology: Aβ42, tau or phosphorylated-tau: The results show that the signature of the following 18 top ranked lncRNAs enabled an excellent discrimination between AD patients and healthy control population with AUC=0.972 accuracy=0,917 sensitivity=0.83 and specificity=1.

| lncRNA | Rank |
|---|---|
| lnc-TPPP-1:2 | 1 |
| LINC02345:11 | 2 |
| lnc-ZNF273-4:4 | 3 |
| lnc-TACC2-8:6 | 4 |
| LINC01206:20 | 5 |
| lnc-C5orf67-3:1 | 6 |
| HAND2-AS1:58 | 7 |
| lnc-PRDM9-20:1 | 8 |
| lnc-CLK1-1:7 | 9 |
| lnc-DNALI1-5:4 | 10 |
| RORB-AS1:6 | 11 |
| lnc-TPPP-1:3 | 12 |
| lnc-BMS1-2:1 | 13 |
| lnc-ADRB1-4:1 | 14 |
| lnc-XXYLT1-5:1 | 15 |
| MIR99AHG:104 | 16 |
| LINC01748:17 | 17 |
| lnc-AKR1E2-15:1 | 18 |

TABLE 10 lncRNAs of the present invention that correlate with CSF biomarkers

| CSF BM | lncRNA | R_AD | PValue | AUC |
|---|---|---|---|---|
| Aβ42 | LINC01748:17 | −0.73 | 0.0242 | 0.77 |
| Aβ42 | lnc-C5orf67-3:1 | 0.72 | 0.0068 | 0.82 |
| Aβ42 | lnc-CYP2E1-1:1 | −0.74 | 0.0332 | 0.24 |
| Aβ42 | lnc-FAP-3:1 | −0.72 | 0.0083 | 0.81 |
| Aβ42 | lnc-FGD4-9:1 | −0.73 | 0.0036 | 0.84 |
| Aβ42 | lnc-GLIPR1L1-2:3 | 0.72 | 0.0205 | 0.22 |
| Aβ42 | lnc-KDM3A-1:4 | −0.77 | 0.0045 | 0.83 |
| Aβ42 | lnc-LRCH1-1:1 | −0.75 | 0.0205 | 0.78 |
| Aβ42 | lnc-NPBWR1-2:2 | 0.81 | 0.0449 | 0.26 |
| Aβ42 | lnc-PLA2G2F-1:2 | −0.74 | 0.0121 | 0.20 |
| Aβ42 | lnc-POU2AF1-1:2 | −0.84 | 0.0205 | 0.78 |
| Aβ42 | lnc-RCSD1-4:1 | −0.72 | 0.0387 | 0.75 |
| Aβ42 | lnc-SERPINI1-14:1 | −0.74 | 0.0449 | 0.74 |
| Aβ42 | lnc-TAF9-10:1 | −0.75 | 0.0284 | 0.76 |
| Aβ42 | lnc-TNFRSF19-2:1 | 0.71 | 0.0332 | 0.24 |

TABLE 10-continued lncRNAs of the present invention that correlate with CSF biomarkers

| CSF BM | lncRNA | R_AD | PValue | AUC |
|---|---|---|---|---|
| Aβ42 | lnc-TPPP-1:2 | −0.86 | 0.0001 | 0.92 |
| Aβ42 | lnc-TPPP-1:3 | 0.8 | 0.0056 | 0.17 |
| Aβ42 | lnc-ZNF273-4:4 | −0.87 | 0.0036 | 0.84 |
| T-tau | HAND2-AS1:58 | 0.92 | 0.0045 | 0.83 |
| T-tau | HAND2-AS1:59 | 0.9 | 0.0056 | 0.83 |
| T-tau | HAND2-AS1:70 | 0.8 | 0.0018 | 0.86 |
| T-tau | HAND2-AS1:71 | 0.8 | 0.0036 | 0.84 |
| T-tau | LINC00200:6 | 0.71 | 0.0029 | 0.15 |
| T-tau | LINC00649:23 | −0.74 | 0.0036 | 0.84 |
| T-tau | LINC01206:11 | −0.74 | 0.0332 | 0.76 |
| T-tau | LINC01355:9 | 0.83 | 0.0332 | 0.76 |
| T-tau | lnc-ADRB1-4:1 | 0.8 | 0.0056 | 0.83 |
| T-tau | lnc-AKR1E2-15:1 | 0.75 | 0.0205 | 0.22 |
| T-tau | lnc-APBA1-5:1 | 0.8 | 0.0284 | 0.76 |
| T-tau | lnc-BMS1-2:1 | 0.76 | 0.0332 | 0.24 |
| T-tau | lnc-CA7-2:2 | −0.73 | 0.0332 | 0.76 |
| T-tau | lnc-CLK1-1:7 | −0.83 | 0.0083 | 0.81 |
| T-tau | lnc-DAPP1-2:11 | 0.8 | 0.0242 | 0.77 |
| T-tau | lnc-DNALI1-5:4 | −0.76 | 0.0045 | 0.83 |
| T-tau | lnc-ELF1-5:1 | 0.86 | 0.0242 | 0.77 |
| T-tau | lnc-LBH-4:1 | −0.79 | 0.0332 | 0.24 |
| T-tau | lnc-MVB12B-6:1 | 0.89 | 0.0242 | 0.77 |
| T-tau | lnc-MYO18B-2:3 | −0.72 | 0.0145 | 0.79 |
| T-tau | lnc-OR8G5-7:2 | −0.81 | 0.0284 | 0.76 |
| T-tau | lnc-PAX8-6:2 | 0.71 | 0.0242 | 0.23 |
| T-tau | lnc-POLE4-3:1 | 0.71 | 0.0145 | 0.79 |
| T-tau | lnc-SERTM1-1:1 | −0.72 | 0.0121 | 0.80 |
| T-tau | lnc-SOX14-2:1 | 0.71 | 0.0018 | 0.86 |
| T-tau | lnc-SYCP1-4:1 | −0.83 | 0.0387 | 0.25 |
| T-tau | lnc-TACC2-8:6 | −0.78 | 0.0068 | 0.82 |
| T-tau | lnc-TEAD4-1:1 | −0.71 | 0.0449 | 0.26 |
| T-tau | lnc-TF-4:1 | 0.82 | 0.0332 | 0.76 |
| T-tau | lnc-TTF2-4:1 | −0.8 | 0.0449 | 0.74 |
| T-tau | lnc-XXYLT1-5:1 | −0.71 | 0.0083 | 0.81 |
| T-tau | lnc-ZC3H12D-2:3 | −0.72 | 0.0173 | 0.78 |
| T-tau | lnc-ZNF430-3:4 | −0.79 | 0.01 | 0.81 |
| T-tau | MIR99AHG:104 | 0.9 | 0.0045 | 0.83 |
| T-tau | PITRM1-AS1:10 | 0.91 | 0.0242 | 0.23 |
| T-tau | RORB-AS1:6 | 0.73 | 0.0056 | 0.83 |
| T-tau | SEC24B-AS1:19 | −0.93 | 0.0205 | 0.22 |
| T-tau | ZNF528-AS1:1 | −0.74 | 0.0387 | 0.75 |
| p-tau | BLACAT1:3 | −0.71 | 0.0145 | 0.21 |
| p-tau | HAND2-AS1:58 | 0.71 | 0.0045 | 0.83 |
| p-tau | KAZN-AS1:4 | −0.73 | 0.0205 | 0.78 |
| p-tau | LINC00649:23 | −0.71 | 0.0036 | 0.84 |
| p-tau | LINC01206:11 | −0.77 | 0.0332 | 0.76 |
| p-tau | LINC01206:20 | 0.84 | 0.0205 | 0.22 |
| p-tau | LINC01684:16 | 0.71 | 0.0242 | 0.77 |
| p-tau | LINC02246:11 | 0.74 | 0.0173 | 0.78 |
| p-tau | LINC02345:11 | −0.75 | 0.0007 | 0.11 |
| p-tau | lnc-AQP8-2:7 | −0.82 | 0.0173 | 0.22 |
| p-tau | lnc-AUH-2:9 | −0.78 | 0.0332 | 0.24 |
| p-tau | lnc-CA7-2:2 | −0.79 | 0.0332 | 0.76 |

TABLE 10-continued lncRNAs of the present invention that correlate with CSF biomarkers

| CSF BM | lncRNA | R_AD | PValue | AUC |
|---|---|---|---|---|
| p-tau | lnc-CLK1-1:7 | −0.73 | 0.0083 | 0.81 |
| p-tau | lnc-ELF1-5:1 | 0.74 | 0.0242 | 0.77 |
| p-tau | lnc-FER1L6-2:1 | 0.83 | 0.0242 | 0.77 |
| p-tau | lnc-HS3ST3A1-1:1 | 0.77 | 0.01 | 0.81 |
| p-tau | lnc-KCTD19-1:1 | 0.78 | 0.0332 | 0.76 |
| p-tau | lnc-LMBRD1-5:17 | −0.73 | 0.0387 | 0.75 |
| p-tau | lnc-MVB12B-6:1 | 0.72 | 0.0242 | 0.77 |
| p-tau | lnc-NKX6-1-2:1 | 0.79 | 0.0121 | 0.80 |
| p-tau | lnc-OR8G5-7:2 | −0.85 | 0.0284 | 0.76 |
| p-tau | lnc-PACRGL-5:1 | 0.71 | 0.0332 | 0.76 |
| p-tau | lnc-PRDM9-20:1 | 0.73 | 0.0173 | 0.78 |
| p-tau | lnc-RHOB-1:3 | −0.76 | 0.0205 | 0.78 |
| p-tau | lnc-RPE65-4:2 | −0.79 | 0.0056 | 0.83 |
| p-tau | lnc-SERTM1-1:1 | −0.82 | 0.0121 | 0.80 |
| p-tau | lnc-SOX14-2:1 | 0.76 | 0.0018 | 0.86 |
| p-tau | lnc-SPAG9-2:1 | 0.71 | 0.0173 | 0.78 |
| p-tau | lnc-SPAG9-2:2 | 0.71 | 0.0173 | 0.78 |
| p-tau | lnc-SYCP1-4:1 | −0.76 | 0.0387 | 0.25 |
| p-tau | lnc-TACC2-8:6 | −0.75 | 0.0068 | 0.82 |
| p-tau | lnc-TEKT3-3:1 | −0.84 | 0.0387 | 0.75 |
| p-tau | lnc-TF-4:1 | 0.73 | 0.0332 | 0.76 |
| p-tau | lnc-TP53TG3D-2:1 | 0.71 | 0.0387 | 0.75 |
| p-tau | MIR99AHG:104 | 0.92 | 0.0045 | 0.83 |
| p-tau | RORB-AS1:6 | 0.81 | 0.0056 | 0.83 |
| p-tau | SEC24B-AS1:19 | −0.75 | 0.0205 | 0.22 |
| p-tau | TM4SF19-AS1:10 | 0.76 | 0.0083 | 0.19 |

MATERIALS AND METHODS

To identify miRNA in plasma or serum or whole blood samples of human subjects, miRNA profiling of 2083 miRNAs was performed using HTG EdgeSeq miRNA whole transcriptome V2 targeted sequencing assay (HTG WTA V2, HTG Molecular, Tucson, United States). This technology is based on nuclease protection targeted RNA sequencing assay that uses an extraction free lysis process followed by a nuclease protection assay (NPA) to prepare a stoichiometric library of nuclease protection probes (NPP) for measurement.

To identify lncRNAs in serum, plasma or whole blood samples of human subjects, circulating total RNA was first extracted and sequencing libraries were prepared by removal of ribosomic RNA (RiboZero TruSeq library preparation kit, Illumina Inc. San Diego, USA) and sequenced on Illumina NextSeq500 with 2×75 bp read length.

ncRNA (miRNA and lncRNA) were also measured by qPCR using specific primers. For this, circulating total RNA was first extracted, reverse transcription and real time PCR using specific primers were performed. Using FiMAP, a proprietary platform based on hybridization of PCR products on coated microdiscs with complementary oligonucleotide coupled to detection probes. Total RNA was extracted followed by reverse transcription and PCR step allowing multiplexing of several targets using specific primers to the ncRNAs. Quantification was therefore performed on the FiMAP platform using coded microdiscs specific of each ncRNA.

Patient population and samples Serum or plasma samples were prepared from blood samples collected in lithium-heparin tubes and whole blood samples were collected in Paxgene RNA tubes. Samples were from healthy volunteers (HV), donors at the "Etablissement Français du Sang" (EFS) of Mulhouse, France, and from cognitively intact healthy control subjects and patients with mild cognitive impairment or with different stages of Alzheimer's disease (AD) recruited according to the protocols of the Amoneta Diagnostics sponsored prospective studies registered to the Agence Nationale de Sécurité du Médicament et des Produits de Santé (ANSM) including ADKIT study under the ID RCB: 2015-A00118-41 on Jan. 22, 2015, the chronobiological study under the ID RCB: 2016-A200227-44 on Feb. 4, 2016.

Method for miRNAs

HTG EdgeSeq Run

HTG whole transcriptome miRNA (WTA) kit was used (HTG WTA V2, HTG Molecular, Tucson, United States). Samples were prepared accordingly to the following protocol: 15 µl of plasma lysis buffer and 15 µl of plasma sample and 3 µl of Proteinase K are mixed and incubated at 50° C. for 60 min with orbital shaking. 25 µl of the mix is transferred to the HTG sample plate and loaded into the HTG processor to perform the nuclease protection assay and prepare the stoichiometric NPP.

Molecular Barcoding and Adapter Addition

For plasma samples, barcoding is performed using Hemo KlenTaq (M0332S, NEB, Evry, France) enzyme. For each sample, we mix 2.4 µl of Hemo KlenTaq, 0.6 µl of dNTPs (10 nM) (NEB, N0447S), 6 µl of OneTaq PCR GC Buffer 5× (B9023S, NEB, Evry, France), 3 µl of Forward and Reverse Primers (HTG WTA, HTG Molecular, Tucson, United States), 3 µl of sample preparation and 12 µl of H20. PCR step was performed on ABI 2720 Thermocycler using the following cycling profile: 95° C. for 4 min followed by 16 cycles of 95° C. for 15 sec, 55° C. for 45 sec and 68° C. for 45 sec. Protocol is ended with 68° C. for 10 min.

PCR Clean Up

In order to remove excess of primer from the library, Agentcour AMPure XP beads (A63880, Beckmancoulter, Villepinte, France) were used. For each sample, 37.5 µl of AMPure XP beads are used in combination with 15 µl of the PCR product. After mixing 10 times with pipette, the solution is incubated for 5 min at room temperature and then placed on the magnetic stand. After 2 minutes to separate beads, the cleared solution is carefully removed without disturbing the beads. Beads are washed 2 times with 200 µl of Ethanol 80%. Elution of PCR product link to the beads is performed with 25 µl of H20. The purified solution of PCR product is place in a new tube while the plate is on the magnetic stand to separate PCR products and beads.

Determination of Library Concentration:

To determine concentration of library for each sample, Kapa Biosystems qPCR Kit (KK4824, Cliniscience, Nanterre, France) is used. For each reaction, the mix is composed of 12 µl of Mastermix, 0.4 µl of ROX dye, 3.6 µl of H20 and 4 µl of template (standards or library diluted at 1/10000). The samples were run on a ABI PRISM 7900HT (High ROX) will the following cycles: 95° C. for 5 min, 35 cycles of 95° C. for 30 sec and 65° C. for 45° C. with data collection followed by a dissociation curve. Standards are corresponding to an amplicon of 452 bp whereas the amplicon of NPP with barcode correspond to 115 bp. The ratio is applied to determine the concentration of each library.

Sample Pooling and Sequencing

Each sample are pooled in order to generate a pooled library at 4 nM. From this pooled library, 5 µl where mixed with 0.2N NaOH freshly prepared and incubated for 2 min. The solution was vortexed briefly and centrifuged at 280 g for 1 minute and mixed with 990 µl of pre-chiller HT1 buffer (Illumina NextSeq Reagent v2 kit, Illumina, Paris, France). 15% PhiX (PhiX control v3, Illumina, Paris, France) at 20 pM was prepared. 260 µl of prepared denatured library at 20 pM was mix with 39 µl of 20 pM PhiX and 1001 µl of HT1

Buffer was loaded into Illumina NextSeq500 Mid Output V2 150 cycles kit and sequenced.

Sequence Analysis

Data reconstruction and analysis was performed using directly FASTQ files from the Illumina Sequencer and processed by the HTG Parser software.

Statistics

The data are normalized using the method recommended by the supplier. This normalization is based on total count of sequences after filtering out all values below 70 (threshold recommended by the supplier). After normalization, all miRNAs with 75th percentile of this threshold are considered as noise and have been deleted.

In order to determine miRNAs that discriminate Alzheimer disease patients from healthy control subjects, the following statistical methods are applied to the normalized data: two-tailed Welch t test and computation fold change were performed on normalized data. Individual ROC Curve was performed for each miRNA detected in the samples. The random Forest algorithm with the best miRNA in term of AUROC was performed to establish a predictive model for the diagnosis of Alzheimer disease.

The final list of miRNAs of interest was chosen with p value <0.05 or fold change >1.49 or <0.75 in Log 2 and/or individual AUC determined by the selection of all the miRNAs that are at least in one of the three lists of selected biomarkers (tables 1, 2 and 3).

Method for lncRNA

Samples Sequencing

Ribonucleic acid (RNA) extraction is performed starting from 1.5 ml of serum, using Norgen Serum/plasma extraction and RNA Clean-Up and Concentration Micro-Elute Kits according to the manufacturer's instructions.

Sequencing libraries are prepared from the total amount of extracted RNA, using the Illumina TruSeq stranded total RNA library preparation kit combined with the human/mouse/rat RiboZero rRNA removal kit (Illumina Inc. San Diego, USA, C). All steps are performed with the low-throughput protocol and according to the manufacturer's instructions, with no fragmentation step. Briefly, cytoplasmic ribosomal RNA (rRNA) are hybridized to biotinylated target-specific oligos and removed using streptavidin coated magnetic beads. rRNA depleted RNA samples are then reverse transcribed into complementary deoxyribonucleic acid (cDNA). To ensure strand specificity, single stranded cDNA is first synthetized using Super-Script II reverse transcriptase (Invitrogen) and random primers in the presence of Actinomycin D, and then converted to double stranded cDNA with the second strand marking mix that incorporates dUTP in place of dTTP. Resulting blunt ended cDNA are purified using AMPure XP magnetic beads. After a 3'end adenylation step, Illumina's adapters ligation is performed. So, obtained singled indexed libraries are washed twice using AMPure XP beads to remove excess adapters and enriched by PCR (15 cycles). PCR products are purified with a final AM Pure XP beads wash and sequencing ready libraries are eluted in 30 µl of resuspension buffer. For quality control, 1 µl of each library is run on the Agilent Technologies 2100 Bioanalyzer using a DNA 1000 chip according to the manufacturer's recommendations. Absence of adapter dimers is checked and the average library size is determined by a region table.

Libraries are quantified on Qubit 2.0 using Qubit dsDNA High Sensitivity assay kit (Invitrogen). Library size previously determined on the Bioanalyzer is used to calculate molar concentrations from mass concentrations.

All libraries are sequenced with the Illumina NextSeq500 (2×75 bp).

Bioinformatic Analysis

RNA-seq data analysis is performed using Partek Flow (Partek Inc., St Louis, Mo., USA build 6). The pre-alignment QA/QC module of Partek Flow is used to visualize the read quality of the FASTQ files. All reads are examined. The raw FASTQ files are trimmed at the 3' end in function of their quality score (Phred score). The parameters used are an end minimum quality level of 30 and a minimum trimmed read length of 50. Unaligned reads are mapped using the *Homo sapiens* hg19 genome. This mapping is done using the software STAR version 2.5.3 (Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinforma. Oxf. Engl. 29, 15-21). The default parameters are used. The post-alignment QC module of Partek Flow was used to visualize the average base quality score per position as well as the mapping quality per alignment. The mapped reads were quantified using the GTF file with the patented lncRNA annotation for quantification using the Partek Expectation/Maximization (E/M) algorithm (Xing, Y., Yu, T., Wu, Y. N., Roy, M., Kim, J., and Lee, C. (2006). An expectation-maximization algorithm for probabilistic reconstructions of full-length isoforms from splice graphs. Nucleic Acids Res. 34, 3150-3160). The default parameters are used. The transcripts where their medians are under the median read density in intergenic regions are discarded for the next steps of the analysis. The transcript counts were normalized by CPM (counts per million). Only transcripts showing high expression (CPM 10) in at least half the samples of one group are considered.

Statistical Analysis and Predictive Modelling

To determine differentially expressed lncRNA, a statistical analysis is performed using Wilcoxon Mann-Whitney parametric test. A lncRNA with a p value 0.05 is considered as differentially expressed. In order to build classification models for the 2 classifications, the Classification for MicroArrays (CMA) package of R (Slawski M, Daumer M, Boulesteix A L. CMA: a comprehensive Bioconductor package for supervised classification with high dimensional data. BMC Bioinformatics 2008, 9:439) with a leave-one-out cross-validation has been used. The algorithms used for this predictive modelling are (a) random forest, (b) linear discriminant analysis and (c) naïve Bayes (Breiman L. Random forests. Machine Learning, 45(1): 5-32, 2001).

The rank of the RNA candidate in a model was calculated by the mean rank of 10 candidates selections (per CV-fold). Per model (and RNA selection method) the AUC was plotted as a function of the number of RNAs in the model. The optimal number of RNAs per model was determined graphically. ROC curves and confusion matrices were generated to assess the predictive performance of our models. The values of AUC, accuracy, sensitivity, specificity, positive and negative predictive values are reported.

Additional Method for Quantification of miRNA and lncRNA

Total RNA Extraction

Total RNA was extracted using Paxgene Blood RNA kit (Qiagen, France) and Serum/Plasma mini kit (Norgen Biotek, Canada) respectively, according to manufacturer's instructions. RNA quality was examined on an Agilent 2100 Bioanalyzer with the RNA 6000 Nano Kits (Agilent, France). RNA quantity was measured on Qubit 3.0 fluorometer using RNA High sensitivity kit (Fisher Scientific, France).

cDNA Synthesis

Total RNA was used for miRNA and lncRNA cDNA synthesis as follows. For miRNA, 100 ng of RNA was reverse transcribed in a final volume of 10 µl including 1 µl of 10× poly(A) polymerase buffer, 0.1 mM of ATP, 1 µM of universal miRNA RT-primer, 0.1 mM of each deoxynucleotide (dATP, dCTP, dGTP and dTTP), 100 units of MuLV reverse transcriptase (New England Biolabs, USA) and 1 unit of poly(A) polymerase (New England Biolabs, USA) was incubated at 42° C. for 1 hour followed by enzyme inactivation at 95° C. for 5 minutes. The sequence of the RT-primer was 5'-CAGGTCCAGTTTT TTTTTTT-TTTTVN, where V is A, C and G and N is A, C, G and T. The primer was purchased from IDT (Integrated DNA Technologies, Belgium).

For lncRNAs, Reverse transcription was performed using high capacity cDNA reverse transcription kit (Fisher scientific, France) according to the manufacturer instructions.

qPCR Quantification

For lncRNA, preamplification reactions were prepared using Applied Biosystems preamplification master mix with 0.1× (100 nM) of each of the primers pairs corresponding to the lncRNAs. 16 preamplification cycles were performed as preconized by the furnisher (50° C. 2 minutes, 96° C. 10 minutes, 40 cycles at 95° C. for 15 seconds and 60° C. for 1 minute). For miRNA amplification, primers were designed using miR primer tool (PMID: 24472427). Quantitative PCR of biological samples was done in 10 µl total volume with 1 µl of cDNA or preamplification product diluted 1/20 in TE buffer (for miRNA and lncRNA respectively), 5 µl of 2× Soadvanced SYBR green PCR master mix (Biorad, USA) and 250 nM of each primer. Cycling conditions were 95° C. for 5-10 min followed by 40 cycles of 95° C. for 10-30 sec and 60° C. 30-60 sec. A melting curve analysis (60° C. to 99° C.) was performed after the thermal profile to ensure specificity in the amplification. Relative expression level was determined against a standard curve realized on a 5 log scale using CFX maestro Software (Biorad, USA).

FIMAP Quantification lncRNA and miRNAs of interest were also quantified using the FIMAP/QMAP platform developed by Quantamatrix (South Korea). Briefly, lncRNAs and miRNAs were amplified by PCR using primers with the same sequences as for qPCR that were chemically modified. Forward primers were phosphorylated in 5' and Reverse primers biotinylated in 5'. Multiplexed PCR reactions were performed on Biorad T100 thermocycler in 20 µl reactions containing 2 µl of miRNA or lncRNA cDNA, 250 nM of each primers and 10 µl of 2× One Taq Hot Start 2× master Mix (New England Biolabs, USA) with the following conditions: 30 seconds at 94° C., 25 cycles of 30s at 94° C., 1 min at 60° C. and 1 min at 68° C., followed by a final extension at 68° C. for 5 minutes. PCR products were then digested with 25U of lambda exonuclease for 30 minutes at 37° C. to eliminate the phosphorylated strand and keep only the biotinylated ones. So digested products were quantified on QMAP using coded silica microdisks coated with oligos complementary to the RNAs of interest (one code per target oligo). Briefly, biotinylated PCR products were incubated with the coated microdisks in a 96 well plate, and hybridized products revealed by addition of a fluorescent streptavidin conjugate, SAPE (Prozyme, Denmark) after washing steps. Plates were imaged on QMAP that takes 2 images per spot: one dark image to quantify the fluorescence and 1 white light image to read the microdisks codes. Each target relative expression is then calculated by QMAP software by assigning fluorescence signal to each target according to the associated microdisk code.

RESULTS

Profiling of 2083 miRNAs based on the miRbase v20 was performed on plasma samples from patients suffering of mild impairment or moderate Alzheimer disease and cognitively intact healthy subjects. After normalization of the results generated with HTG EdgeSeq technology, averages of 406 miRNAs par sample were positively identified. From these 406 miRNAs identified, statistical analysis was performed in order to identify miRNAs with predictive value of Alzheimer disease.

Figure 2:
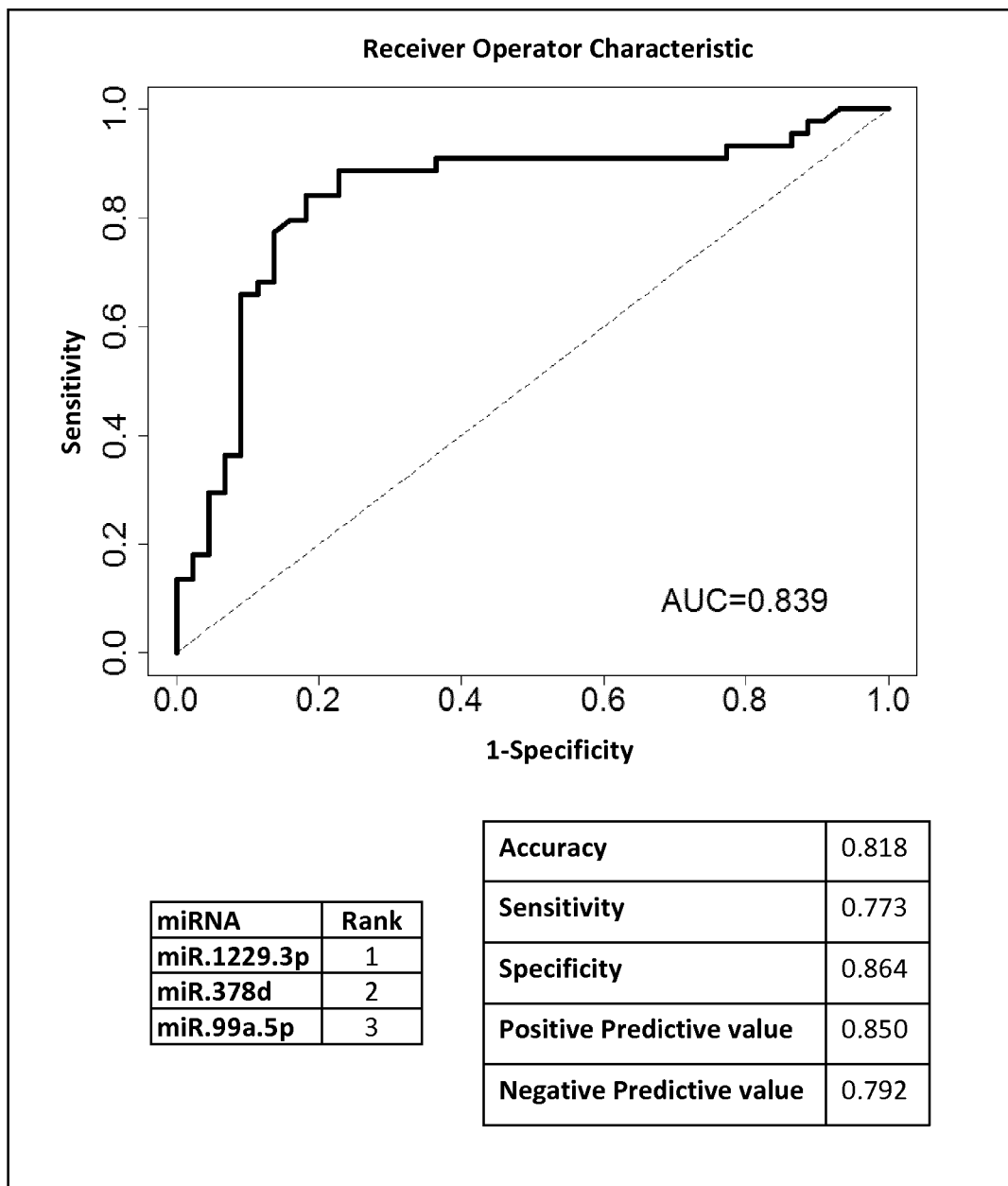
FIG. 2 shows a predictive model using random forest for the diagnosis of AD patients. Three miRNAs were used in this example of results and show a good AUC of 0.839 and an accuracy of 0.818.
Figure 3:
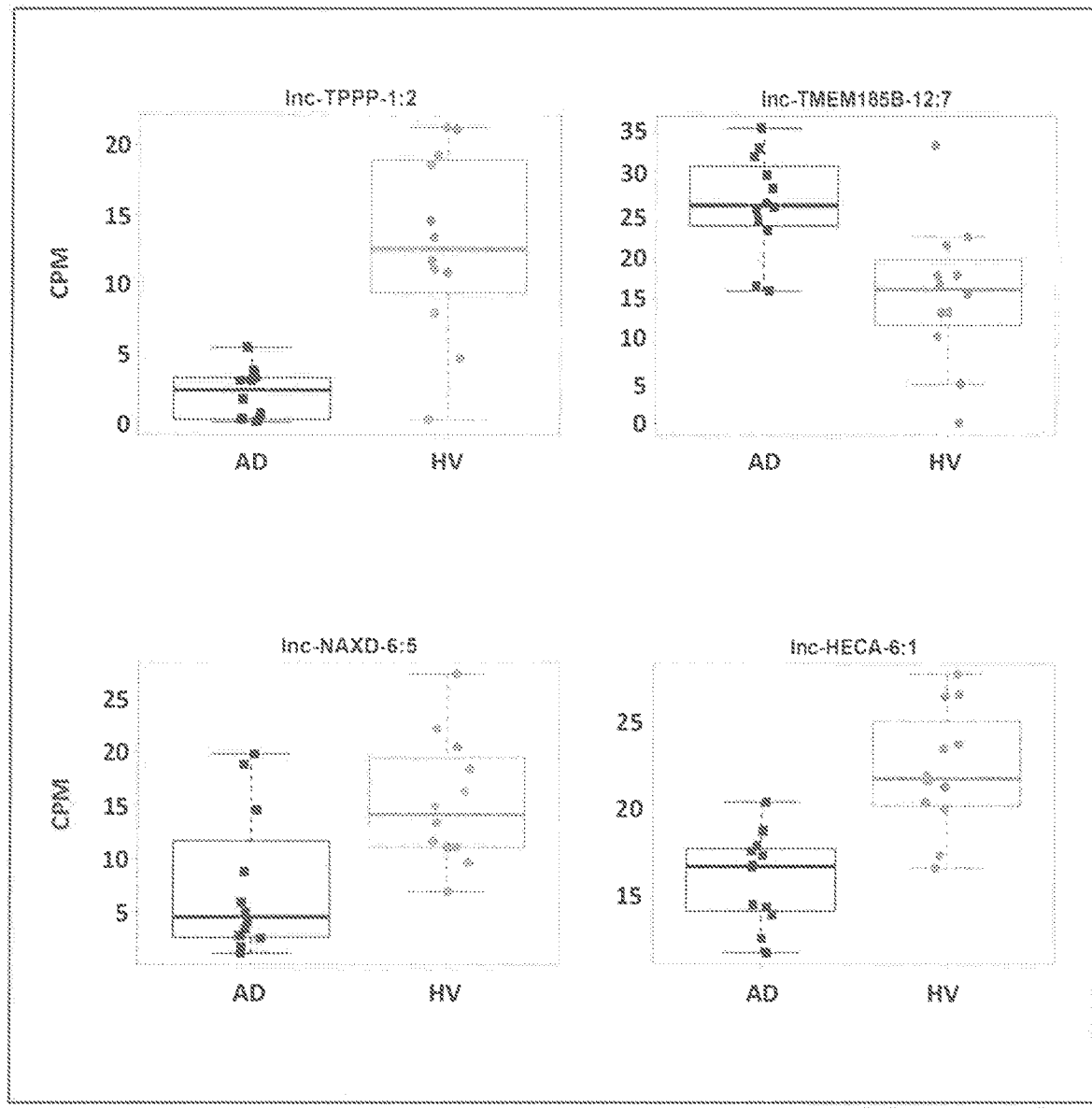
FIG. 3 shows the expression level of lncRNA candidates lnc-TPPP-1:2, lnc-TMEM185B-12:7, lnc-NAXD-6:5 and lnc-HECA-6:1 on human serum samples from patients with early to moderate Alzheimer (AD) and age-matched healthy controls. Y axis: mean+/−standard error of the mean of concentration of the lncRNAs in CPM (count per million). X axis: AD: Alzheimer patient group, HV: Healthy control group.
Figure 4:
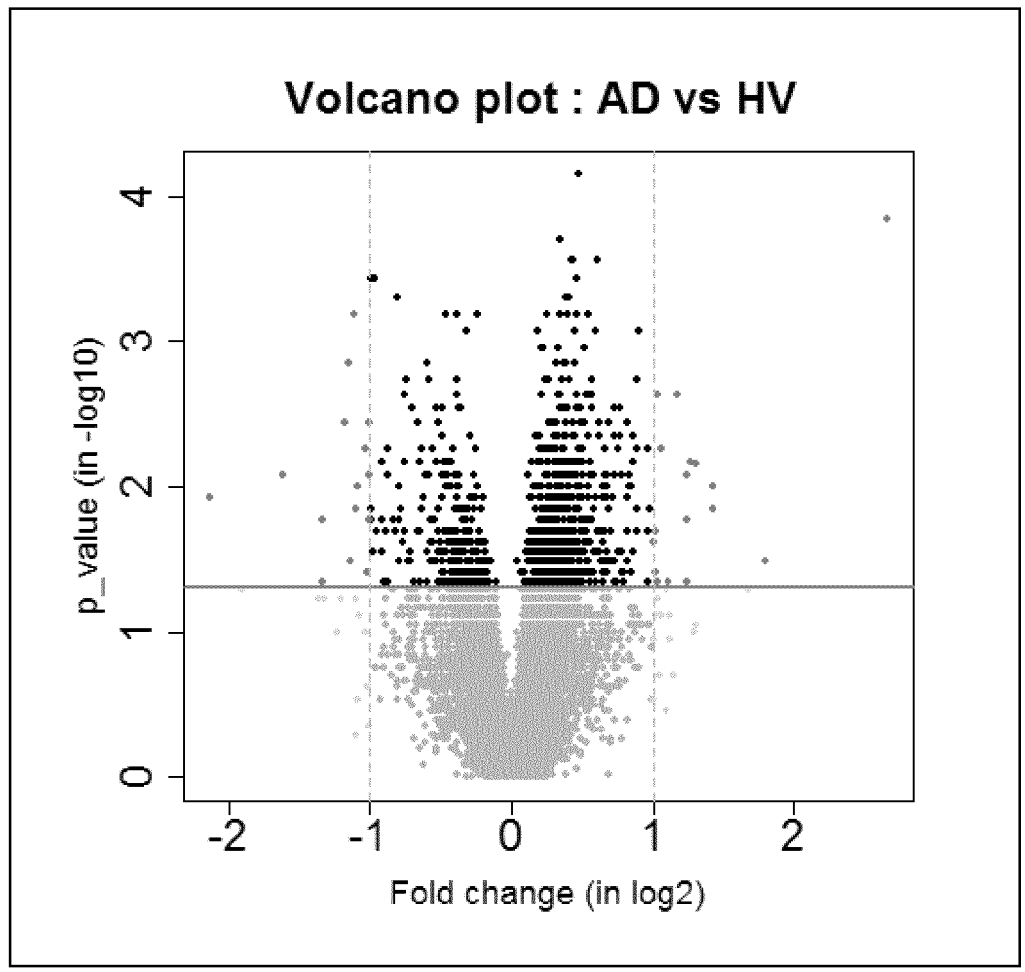
FIG. 4 shows Volcano plot of the comparison. The volcano plot shows the 1008 lncRNAs that are differentially expressed in AD group versus HV (healthy control) group with statistical significance (p<0.05) above the line. 33 lncRNAs show both p value of <0.05 and fold change of ≥2 or ≤0.5. The lncRNAs that are differentially expressed but do not reach a statistical significance are shown below the line.
Figure 5:
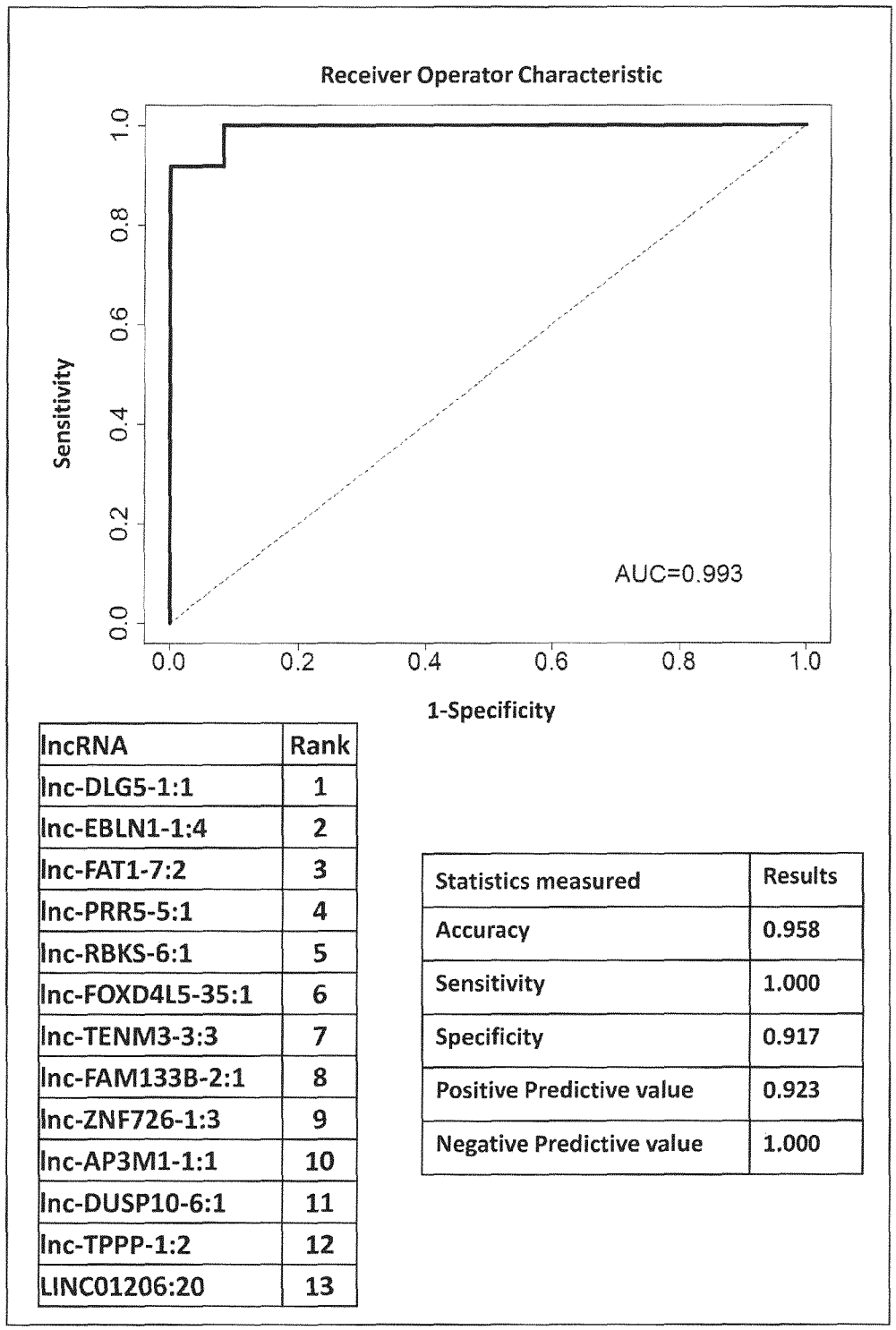
FIG. 5 shows a predictive modelling based on the random forest algorithm enabling the identification of the signature of the 13-top ranked lncRNAs candidates selected out of 19867 lncRNAs.
Figure 6:
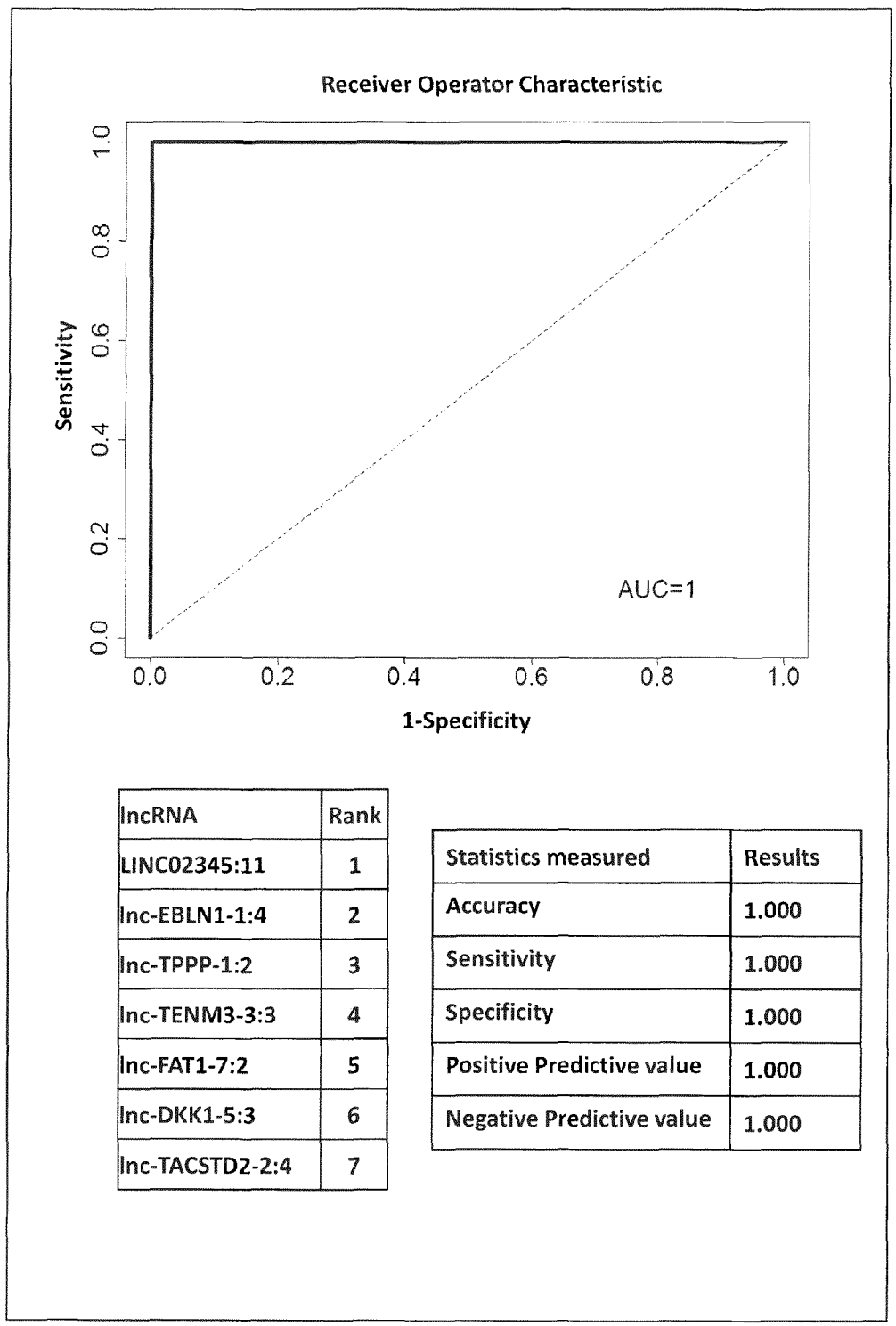
FIG. 6 shows a predictive modelling based on the random forest algorithm enabling the identification of the signature of the 7-top ranked lncRNAs candidates out of 90 lncRNAs with a p value of <0.05 and fold change of ≥2 or ≤0.5 or an AUC of ≥0.85 or ≤0.15.
Figure 7:
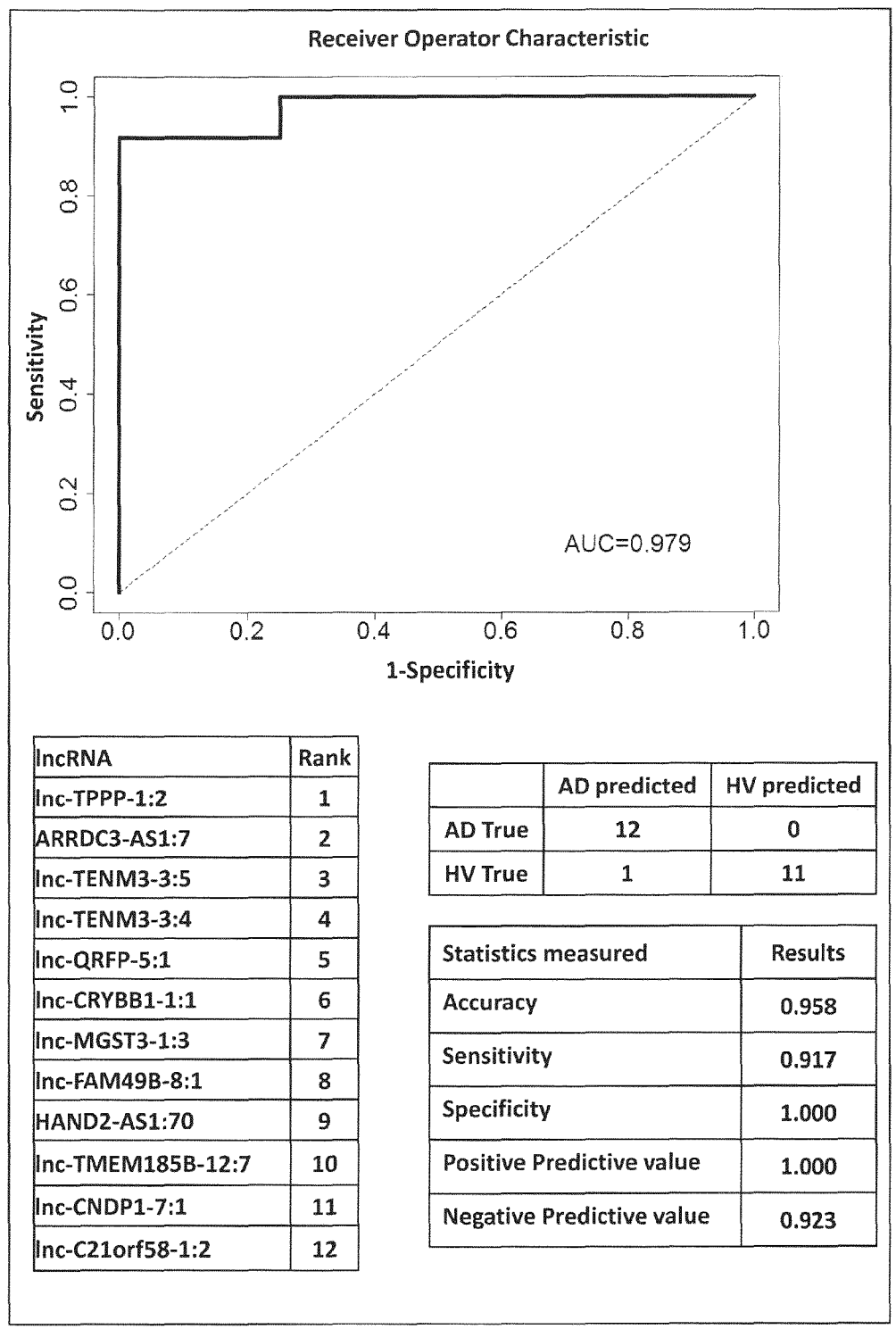
FIG. 7 shows a predictive modelling based on the random forest algorithm enabling identification of the signature of the 12 top lncRNAs candidates selected out of the 90 lncRNAs (with a p value of <0.05 and fold change of ≥1.6 or ≤0.6 and an AUC of ≥0.85 or ≤0.15.
Figure 8:
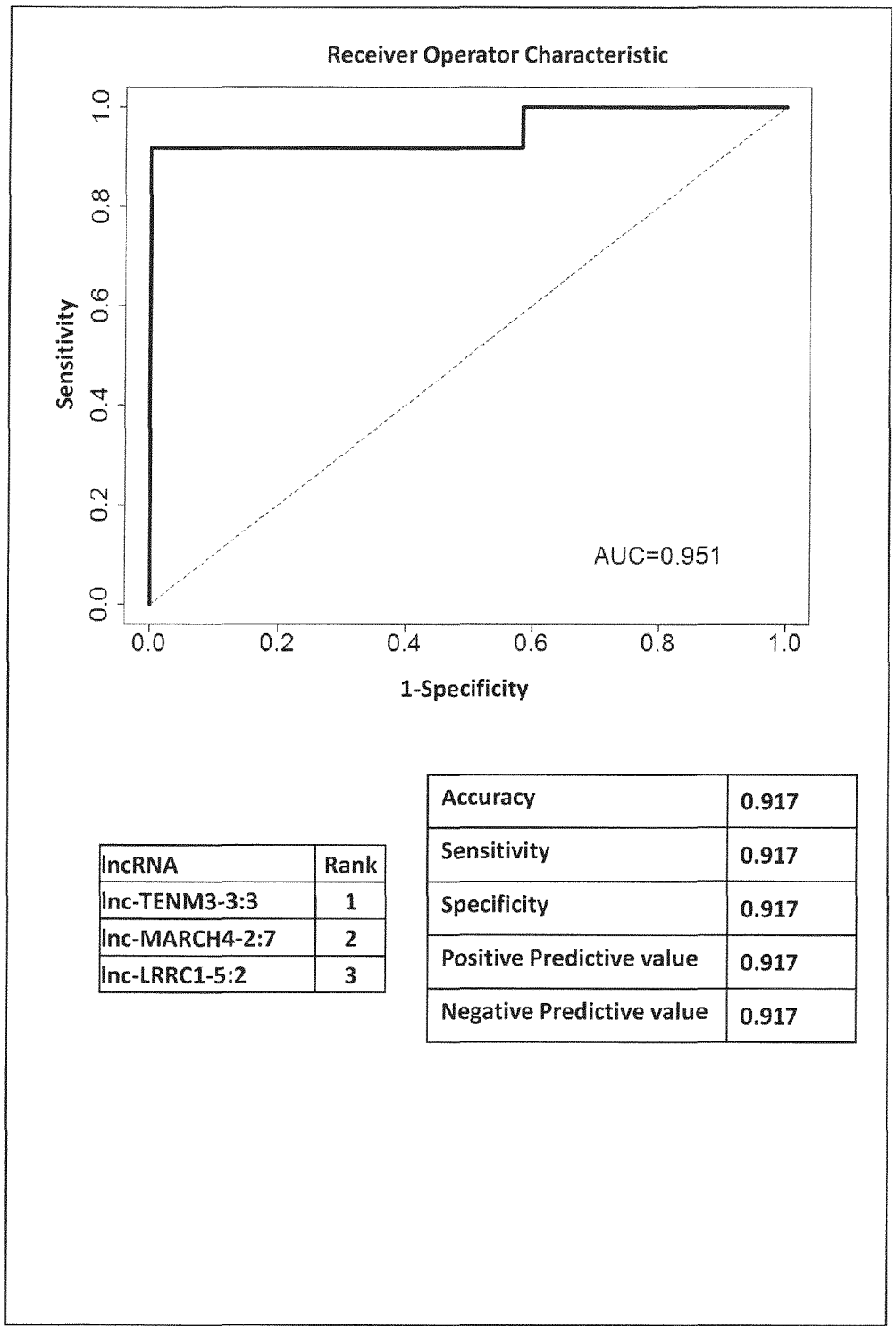
FIG. 8 shows a predictive modelling based on the random forest algorithm enabling identification of the signature of the 3 top lncRNA candidates selected out of the lncRNAs with a p value of <0.05 and a good correlation (Pearson) with scores of neurocognitive tests including MMSE and/or MoCA out of 7 neuropsychological tests performed.
Figure 9:
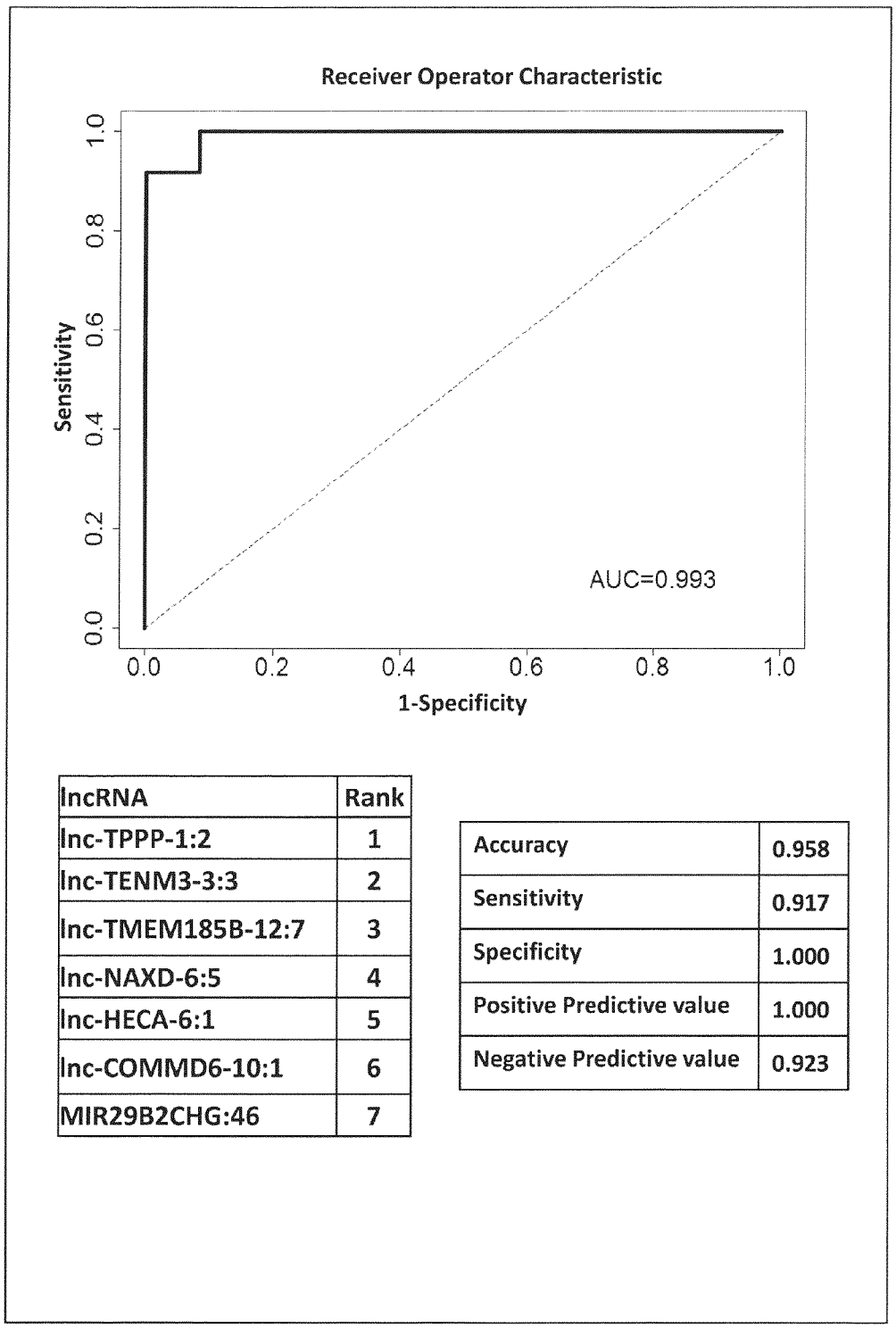
FIG. 9 shows a predictive modelling based on the random forest algorithm enabling the identification of the signature of the 7 top lncRNA candidates selected out of lncRNAs with a p value of <0.05 and a good correlation (Pearson) with neuroimaging scores (volume of brain structures of relevance for cognition and memory such as the mediotemporal area, left and right hippocampus, left and right amygdala, entorhinal cortex out of more than 120 structures measured.
Figure 10:
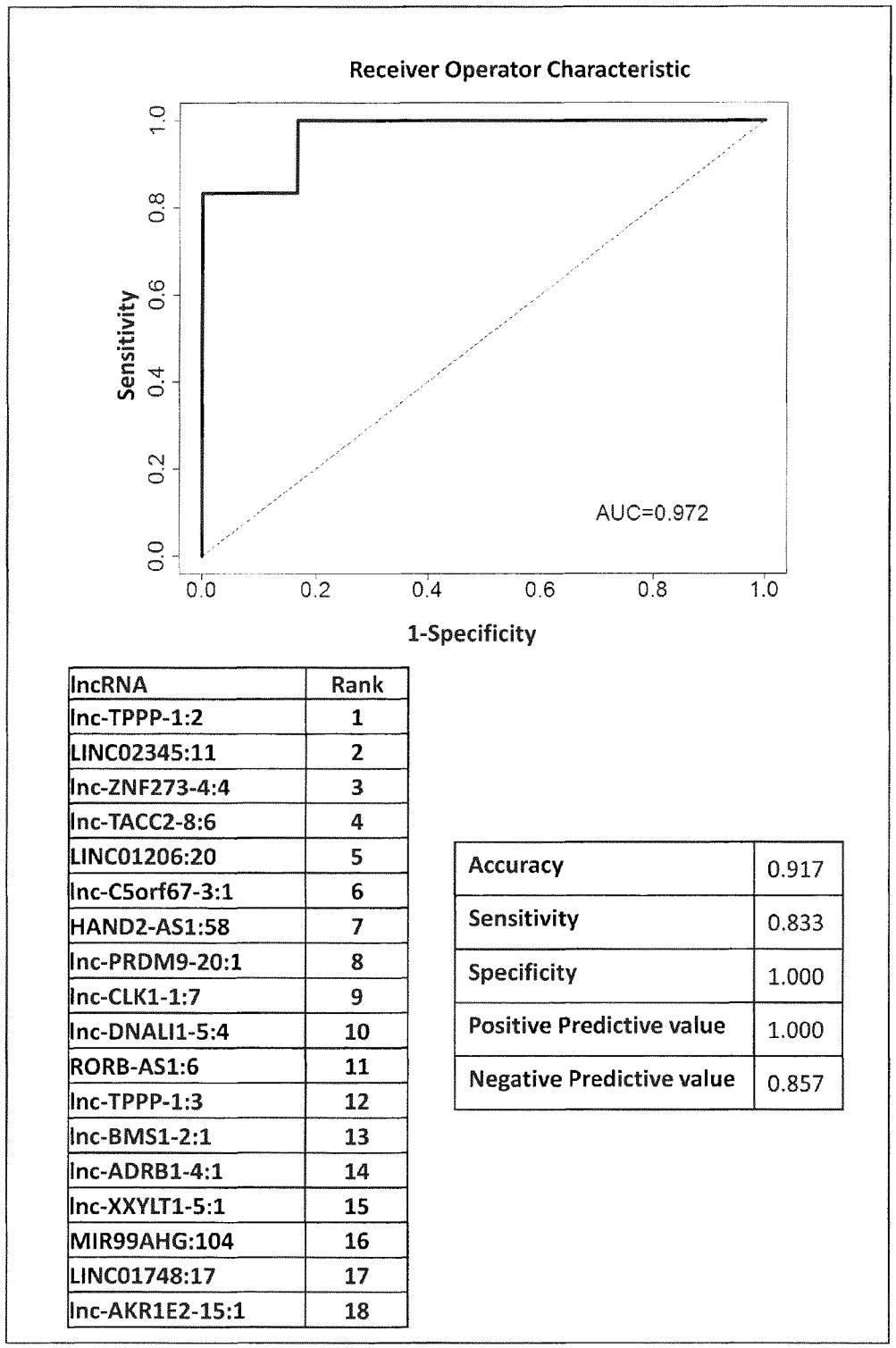
FIG. 10 shows a predictive modelling based on the random forest algorithm enabling the identification of the signature of the 18 top lncRNA candidates selected out of lncRNAs that show a p value of <0.05 and a good correlation (Pearson) with CSF biomarkers Aβ42 and tau (total tau or phosphorylated tau).

Random Forest algorithm was used for the classification model. From this, several sets of 2 to 20 miRNAs with high predictive value were identified and provide an AUC ranged from 0.839 to 0.793 with an accuracy over 0.77, specificity over 0.77 and sensitivity superior to 0.74. FIG. 2 shows a predictive model combining 3 miRNAs with an AUC of 0.839. A list of miRNAs useful for diagnosis of Alzheimer disease was generated. This list was determined using multiple statistical analyses: individual AUC, fold change and t-test for p value (Tables 2, 3 and 4). 74 miRNAs were selected from plasma lithium heparin samples, from the data set with a p value under 0.05. They were further analyzed based on fold change ≥1.49 or <0.75 and individual AUC >0.6 or <0.4. See Tables 2, 3 and 4.

Profiling 127,802 transcripts based on LNCipedia v5.2 was performed on serum samples from patients suffering of Alzheimer disease and cognitively intact healthy subjects using total-RNAseq technology. Above 127,802 transcripts, 19867 lncRNAs were identified with expression level of over 10 CPM in at least half the samples of one group.

Out of 19867 lncRNAs, 1008 lncRNAs useful for diagnosis of Alzheimer disease was selected based on the statistical significance (p value <0.05, Wilcoxon test). Random Forest algorithm was used for the classification model. From this, several sets of 2-20 lncRNAs with high predictive value were identified. The sets of selected 2-20 lncRNAs provide an AUC ranged from 0.7 and up to 1 with an accuracy, sensitivity and specificity ranged from 0.7 to 1.

Figure 11:
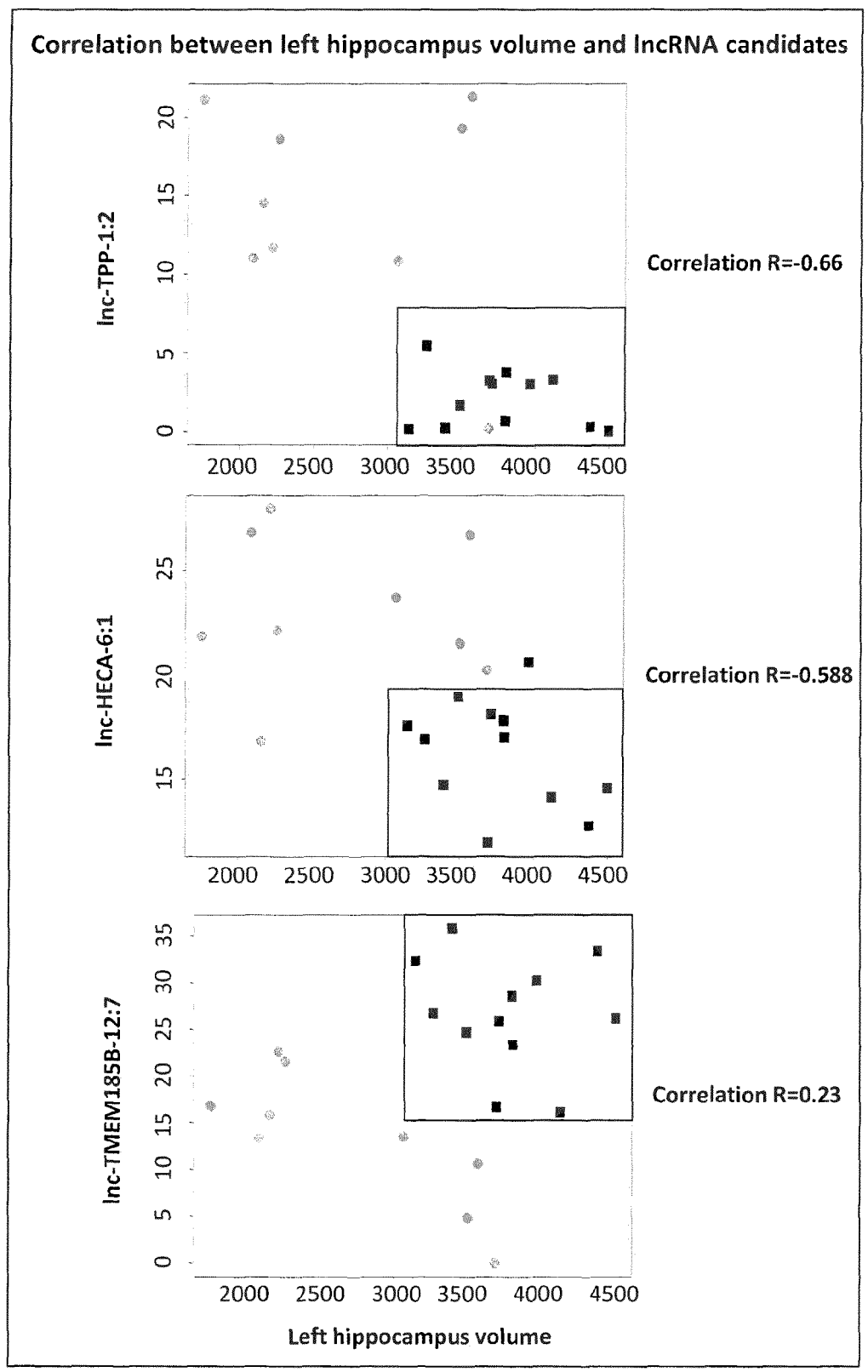
FIG. 11 shows examples of results on correlation between the level of lncRNAs and the volumetric neuroimaging score of brain structures implicated in cognition such as the mediotemporal area and the hippocampus.
Figure 12:
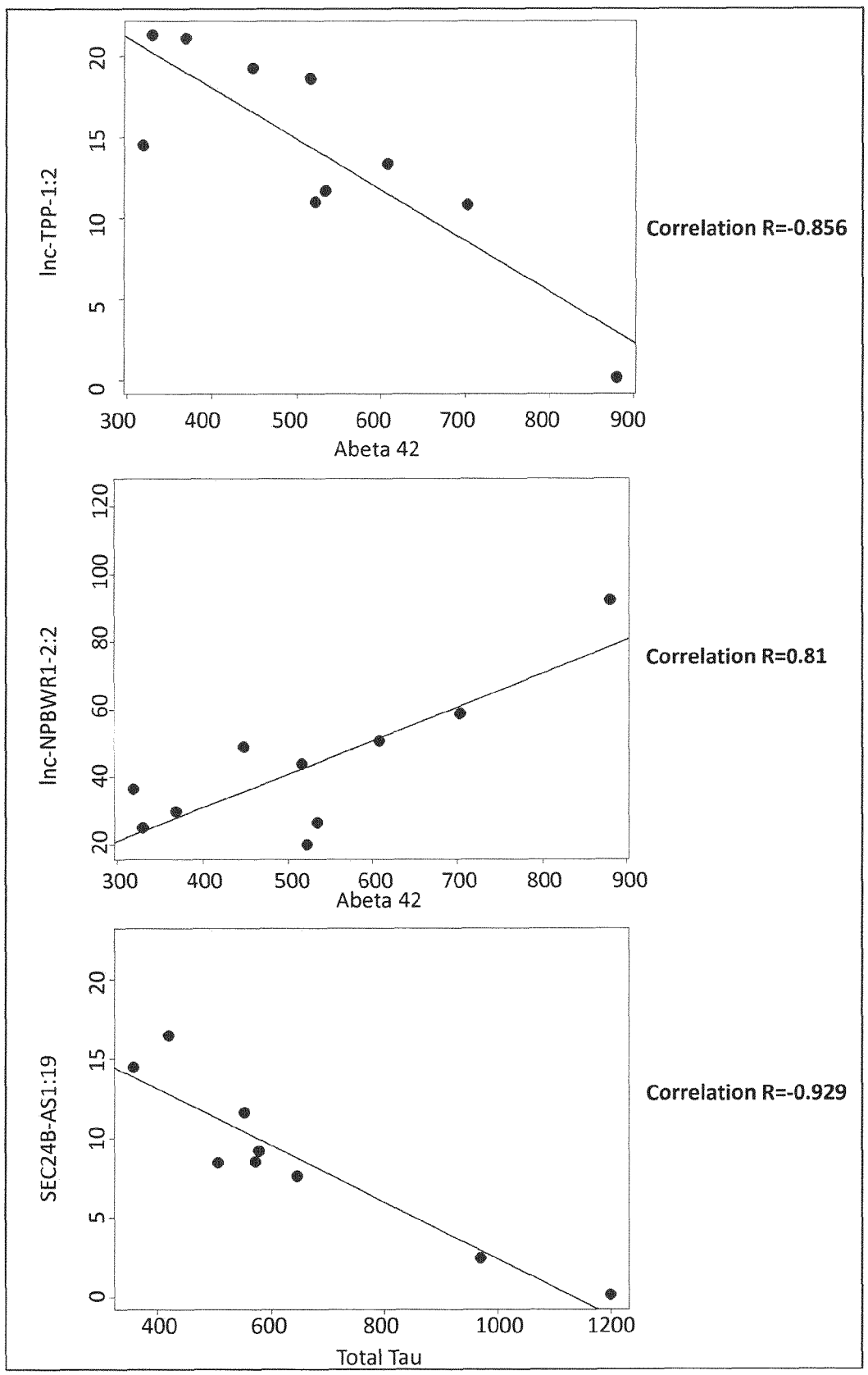
FIG. 12 shows examples of results on correlation between lncRNAs and CSF biomarkers Aβ42 or Tau.

FIGS. 3 to 12 show examples of results on a) the level of expression of individual lncRNA (FIG. 3), b) the statistical significance (p value) to differentiate the 2 populations, schematized as a Volcano plot (FIG. 4), c) predictive modelling using the Random Forest algorithm enabling identification of several sets of lncRNA signatures for diagnosis of Alzheimer (FIGS. 5-10) and d) correlation of the lncRNA level with neuroimaging or CSF biomarkers (FIGS. 11, 12).

SEQUENCE LISTING

The patent contains a lengthy sequence listing. A copy of the sequence listing is available in electronic form from the USPTO web site (https://seqdata.uspto.gov/?pageRequest=docDetail&DocID=US11718879B2). An electronic copy of the sequence listing will also be available from the USPTO upon request and payment of the fee set forth in 37 CFR 1.19(b)(3).

The invention claimed is:

1. A method of detecting levels of expression of lncRNAs in a lncRNA signature, comprising:
    (a) isolating a biological sample from a subject, wherein the biological sample is selected from blood, plasma, and serum, and the subject is human;
    (b) detecting levels of expression of lncRNAs in a LncRNA signature in the biological sample from said subject, wherein the lncRNA signature comprises 13 lncRNAs of lnc-DLGS5-1:1, lnc-EBLN1-1:4, lnc-FAT1-7:2, lnc-PRR5-5:1, lnc-RBKS-6:1, lnc-FOXD4L5-35:1, lnc-TENM3-3:3, lnc-FAM133B-2:1, lnc-ZNF726-1:3, lnc-AP3M1-1:1, lnc-DUSP10-6:1, lnc-TPPP-1:2, and LINC01206:20.

2. A method for treating Alzheimer's disease, said method comprising:
    (i) performing the method of claim 1;
    (ii) diagnosing the human subject with Alzheimer's disease when the expression levels of each of the lncRNAs in the lncRNA signature are increased or decreased in comparison to reference expression levels of the lncRNAs in control samples obtained from healthy subjects; and
    (iii) administering a treatment to the human subject diagnosed with Alzheimer's disease, wherein the treatment is selected from cholinesterase inhibitors, NMDA receptor antagonists, beta-secretase inhibitors, anti-beta-amyloid monoclonal antibodies, modulators of kinases or phosphatases that regulate tau phosphorylation status and anti-tau antibodies.

3. The method of claim 2, wherein the treatment is selected from rivastigmine, galantamine, donepezil, and memantine.

\* \* \* \* \*